United States Patent
Stock et al.

(10) Patent No.: US 10,568,871 B2
(45) Date of Patent: *Feb. 25, 2020

(54) TRIAZOLONE COMPOUNDS AND USES THEREOF

(71) Applicant: Tempest Therapeutics, Inc., San Francisco, CA (US)

(72) Inventors: Nicholas Simon Stock, Encinitas, CA (US); Austin Chih-Yu Chen, San Marcos, CA (US); Yalda Mostofi Bravo, San Diego, CA (US); Jason Duarte Jacintho, San Diego, CA (US); Jill Melissa Baccei, Poway, CA (US); Brian Andrew Stearns, Encinitas, CA (US); Ryan Christopher Clark, San Diego, CA (US)

(73) Assignee: TEMPEST THERAPEUTICS, INC., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/590,766

(22) Filed: May 9, 2017

(65) Prior Publication Data
US 2017/0239223 A1    Aug. 24, 2017

Related U.S. Application Data

(63) Continuation of application No. 14/654,225, filed as application No. PCT/US2013/074197 on Dec. 10, 2013, now Pat. No. 9,676,754.

(60) Provisional application No. 61/739,906, filed on Dec. 20, 2012.

(51) Int. Cl.
| | |
|---|---|
| A61K 31/4196 | (2006.01) |
| C07D 401/10 | (2006.01) |
| C07D 403/10 | (2006.01) |
| C07D 401/06 | (2006.01) |
| C07D 249/12 | (2006.01) |
| C07D 403/06 | (2006.01) |
| A61K 31/4439 | (2006.01) |
| A61K 31/506 | (2006.01) |

(52) U.S. Cl.
CPC ...... *A61K 31/4196* (2013.01); *A61K 31/4439* (2013.01); *A61K 31/506* (2013.01); *C07D 249/12* (2013.01); *C07D 401/06* (2013.01); *C07D 401/10* (2013.01); *C07D 403/06* (2013.01); *C07D 403/10* (2013.01)

(58) Field of Classification Search
CPC .................................................. A61K 31/4196
See application file for complete search history.

(56) References Cited

U.S. PATENT DOCUMENTS

| | | | |
|---|---|---|---|
| 4,487,773 | A | 12/1984 | Temple, Jr. et al. |
| 5,284,957 | A | 2/1994 | Huff |
| 5,294,596 | A | 3/1994 | Haas et al. |
| 5,550,244 | A | 8/1996 | Kluth et al. |
| 5,629,311 | A | 5/1997 | Hemmerle et al. |
| 5,856,495 | A | 1/1999 | Weckbecker et al. |
| 7,816,522 | B2 | 10/2010 | Clark et al. |
| 7,915,267 | B2 | 3/2011 | Nara et al. |
| 9,505,728 | B2 | 11/2016 | Stock et al. |
| 9,676,754 | B2 | 6/2017 | Stock et al. |
| 9,776,976 | B2 | 10/2017 | Stock et al. |

(Continued)

FOREIGN PATENT DOCUMENTS

| | | |
|---|---|---|
| AT | 455547 T | 2/2010 |
| AU | 2003300031 A1 | 5/2004 |

(Continued)

OTHER PUBLICATIONS

Golub, Science, 1999, vol. 286, p. 531-537. (Year: 1999).*
Target Cancer Therapies Fact Sheet, retrieved from http://www.cancer.gov/about-cancer/treatment/types/targeted-therapies/targeted-therapies-fact-sheet on Dec. 8, 2015. (Year: 2015).*
Abd El-Samii et al. Synthesis of some new 3-mercapto-5-substituted-1,2,4-triazine-s-triazoles for evaluation as antimicrobial agents. J Chem Technol Biotechnol 63(2)135-140 (1995).

(Continued)

*Primary Examiner* — Karen Cheng
(74) *Attorney, Agent, or Firm* — Wilson Sonsini Goodrich & Rosati

(57) ABSTRACT

The invention disclosed herein is directed to compounds of Formula I

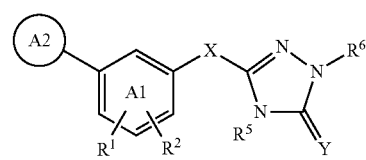

and pharmaceutically acceptable salts thereof, which are useful in the treatment of prostate, breast, colon, pancreatic, human chronic lymphocytic leukemia, melanoma and other cancers. The invention also comprises pharmaceutical compositions comprising a therapeutically effective amount of compound of Formula I, or a pharmaceutically acceptable salt thereof. The invention disclosed herein is also directed to methods of treating prostate, breast, ovarian, liver, kidney, colon, pancreatic, human chronic lymphocytic leukemia, melanoma and other cancers. The invention disclosed herein is further directed to methods of treating prostate, breast, colon, pancreatic, chronic lymphocytic leukemia, melanoma and other cancers comprising administration of a therapeutically effective amount of a selective PPARα antagonist. The compounds and pharmaceutical compositions of the invention are also useful in the treatment of viral infections, such as HCV infections and HIV infections.

20 Claims, 1 Drawing Sheet

(56) References Cited

U.S. PATENT DOCUMENTS

| | | |
|---|---|---|
| 2002/0052510 A1 | 5/2002 | Hamilton et al. |
| 2004/0116491 A1 | 6/2004 | King et al. |
| 2005/0043181 A1 | 2/2005 | Feucht et al. |
| 2007/0032488 A1 | 2/2007 | Botyanszki et al. |
| 2009/0306397 A1 | 12/2009 | Bruns et al. |
| 2010/0022540 A1 | 1/2010 | Eggenweiler et al. |
| 2010/0331397 A1 | 12/2010 | Beigelman et al. |
| 2011/0195993 A1 | 8/2011 | Masson et al. |
| 2011/0319458 A1 | 12/2011 | Jin et al. |
| 2012/0208852 A1 | 8/2012 | Fuerstner et al. |

FOREIGN PATENT DOCUMENTS

| | | |
|---|---|---|
| BE | 894856 A | 2/1983 |
| CA | 1263114 A | 11/1989 |
| CN | 1629142 A | 6/2005 |
| CN | 1993332 A | 7/2007 |
| DE | 160447 A1 | 8/1983 |
| DE | 3238590 A1 | 4/1984 |
| DE | 19521162 A1 | 12/1996 |
| DE | 19601189 A1 | 7/1997 |
| EP | 0060697 A1 | 9/1982 |
| EP | 0067508 A1 | 12/1982 |
| EP | 0273310 A2 | 7/1988 |
| EP | 0422469 A2 | 4/1991 |
| EP | 0513766 A2 | 11/1992 |
| EP | 0540318 A1 | 5/1993 |
| EP | 0665227 A1 | 8/1995 |
| EP | 1834953 A1 | 9/2007 |
| EP | 2330098 A1 | 6/2011 |
| FR | 2535168 A1 | 5/1984 |
| GB | 2293169 A | 3/1996 |
| GB | 2435827 A | 9/2007 |
| GB | 2435828 A | 9/2007 |
| GB | 2435829 A | 9/2007 |
| IN | 183333 B | 11/1995 |
| JP | S60215675 A | 10/1985 |
| JP | 2003513091 A | 4/2003 |
| JP | 2012106996 A | 6/2012 |
| KR | 20110088737 A | 8/2011 |
| NL | 8204109 A | 5/1984 |
| WO | WO-9204346 A1 | 3/1992 |
| WO | WO-9321181 A1 | 10/1993 |
| WO | WO-9411357 A1 | 5/1994 |
| WO | WO-9525443 A1 | 9/1995 |
| WO | WO-9611196 A1 | 4/1996 |
| WO | WO-9613264 A1 | 5/1996 |
| WO | WO-9634851 A1 | 11/1996 |
| WO | WO-9637492 A1 | 11/1996 |
| WO | WO-9701553 A1 | 1/1997 |
| WO | WO-9701554 A1 | 1/1997 |
| WO | WO-9740017 A2 | 10/1997 |
| WO | WO-9804135 A1 | 2/1998 |
| WO | WO-9815277 A2 | 4/1998 |
| WO | WO-9818496 A2 | 5/1998 |
| WO | WO-9843962 A1 | 10/1998 |
| WO | WO-9903835 A1 | 1/1999 |
| WO | WO-9926945 A1 | 6/1999 |
| WO | WO-9962880 A1 | 12/1999 |
| WO | WO-9962888 A1 | 12/1999 |
| WO | WO-0009102 A2 | 2/2000 |
| WO | WO-0009103 A2 | 2/2000 |
| WO | WO-0009125 A1 | 2/2000 |
| WO | WO-0012489 A1 | 3/2000 |
| WO | WO-0029386 A1 | 5/2000 |
| WO | WO-0032588 A2 | 6/2000 |
| WO | WO-0071118 A1 | 11/2000 |
| WO | WO-0146167 A1 | 6/2001 |
| WO | WO-0190102 A2 | 11/2001 |
| WO | WO-0202555 A1 | 1/2002 |
| WO | WO-0220489 A2 | 3/2002 |
| WO | WO-0220501 A2 | 3/2002 |
| WO | WO-0238553 A2 | 5/2002 |
| WO | WO-03000682 A1 | 1/2003 |
| WO | WO-03051315 A2 | 6/2003 |
| WO | WO-03066050 A1 | 8/2003 |
| WO | WO-03084948 A1 | 10/2003 |
| WO | WO-03106448 A2 | 12/2003 |
| WO | WO-2004032840 A2 | 4/2004 |
| WO | WO-2004074257 A1 | 9/2004 |
| WO | WO-2004089306 A2 | 10/2004 |
| WO | WO-2004089380 A2 | 10/2004 |
| WO | WO-2005054179 A2 | 6/2005 |
| WO | WO-2005058848 A1 | 6/2005 |
| WO | WO-2005077178 A2 | 8/2005 |
| WO | WO-2005077345 A1 | 8/2005 |
| WO | WO-2005080379 A1 | 9/2005 |
| WO | WO-2005095362 A1 | 10/2005 |
| WO | WO-2006044732 A2 | 4/2006 |
| WO | WO-2006047195 A2 | 5/2006 |
| WO | WO-2006068199 A1 | 6/2006 |
| WO | WO-2006074984 A1 | 7/2006 |
| WO | WO-2006078698 A1 | 7/2006 |
| WO | WO-2006083645 A2 | 8/2006 |
| WO | WO-2006109056 A1 | 10/2006 |
| WO | WO-2007064797 A2 | 6/2007 |
| WO | WO-2007085349 A1 | 8/2007 |
| WO | WO-2007107758 A1 | 9/2007 |
| WO | WO-2007139955 A2 | 12/2007 |
| WO | WO-2008006499 A2 | 1/2008 |
| WO | WO-2008017594 A1 | 2/2008 |
| WO | WO-2008103574 A2 | 8/2008 |
| WO | WO-2008119662 A1 | 10/2008 |
| WO | WO-2008127349 A2 | 10/2008 |
| WO | WO-2008128335 A1 | 10/2008 |
| WO | WO-2009014910 A2 | 1/2009 |
| WO | WO-2009017863 A2 | 2/2009 |
| WO | WO-2009019472 A1 | 2/2009 |
| WO | WO-2009023402 A2 | 2/2009 |
| WO | WO-2009052078 A1 | 4/2009 |
| WO | WO-2009074782 A1 | 6/2009 |
| WO | WO-2009126863 A2 | 10/2009 |
| WO | WO-2009150240 A1 | 12/2009 |
| WO | WO-2009151529 A1 | 12/2009 |
| WO | WO-2010015212 A1 | 2/2010 |
| WO | WO-2010023946 A1 | 3/2010 |
| WO | WO-2010048207 A2 | 4/2010 |
| WO | WO-2010098600 A2 | 9/2010 |
| WO | WO-2010139966 A1 | 12/2010 |
| WO | WO-2011058478 A1 | 5/2011 |
| WO | WO-2011082400 A2 | 7/2011 |
| WO | WO-2011103546 A1 | 8/2011 |
| WO | WO-2011107530 A2 | 9/2011 |
| WO | WO-2011120926 A1 | 10/2011 |
| WO | WO-2011126903 A2 | 10/2011 |
| WO | WO-2011128316 A1 | 10/2011 |
| WO | WO-2012021455 A1 | 2/2012 |
| WO | WO-2012027482 A2 | 3/2012 |
| WO | WO-2012037299 A2 | 3/2012 |
| WO | WO-2012058531 A2 | 5/2012 |
| WO | WO-2013134562 A1 | 9/2013 |
| WO | WO-2014099503 A1 | 6/2014 |
| WO | WO-2015035059 A1 | 3/2015 |

OTHER PUBLICATIONS

Ammazzalorso et al. Benzothiazole-based N-(phenylsulfonyl)amides as a novel family of PPAR.alpha. antagonists. Bioorg Med Chem Lett 21:4869-4872 (2011).

Argentine et al. The Role of New Technologies in Defining a Manufacturing Process for PPAR.alpha. Agonist LY518674. Organic Process Research & Development 3(2):131-143 (2009).

Braden et al. A Convergent Kilogram-Scale Synthesis of the PPAR.alpha. Agonist LY518674: Discovery of a Novel Acid-Mediated Triazolone Synthesis. Organic Process Research & Development 11(3):431-440 (2007).

Bravo et al. Identification of the first potent, selective and bioavailable PPAR.alpha. antagonist. Bioorg Med Chem Let 24:2267-2272 (2014).

Deng et al. A novel and efficient synthesis of 2,5-substituted 1,2,4-triazol-3-ones. Tetrahedron Letters 46(46):7993-7996 (2005).

Etgen et al. PPAR ligands for metabolic disorders. Current Topics in Medicinal Chemistry 3:1649-1661 (2003).

(56) References Cited

OTHER PUBLICATIONS

Girard. Tautomeric oxotriazoles and hydroxytriazoles. A new method for the preparation of hydroxy-1,2,4-triazoles. Compt rend. 212:547-549 (1941) (English Abstract).
Gol 'Din et al. Synthesis of triazolones and c-aminotriazoles by thermal condensation of carbamidoamidrazones. Chemistry of Heterocyclic Compounds 10(4):489-490 (1974).
Hanif et al. 4-(3-Methoxyphenyl)-3-[2-(4-methoxyphenyl)ethyl]-1H-1,2,4-triazol-5(4H)-o- ne, Acta Crystallographica, Section E: Structure Reports Online, E65(2):o387, sup-1-sup-11 (2009).
Hanif et al. 4-(4-Methoxyphenyl)-3-[2-(2-methoxyphenyl)ethyl]-1H-1,2,4-triazol-5(4H)-o- ne, Acta Crystallographica, Section E: Structure Reports Online, E65(2):o429, sup-1-sup-8 (2009).
Hanif et al. 5-(3-Methoxyphenethyl)-4-(2-methoxyphenyl)-4H-1,2,4-triazol-3-ol, Acta Crystallographica, Section E: Structure Reports Online, E64(11):o2180, sup-1-sup-9 (2008).
Kucukguzel et al. Synthesis of some novel heterocyclic compounds derived from diflunisal hydrazide as potential anti-infective and anti-inflammatory agents. European Journal of Medicinal Chemistry 42:893-901 (2007).
Kuo et al. The synthesis of three isotopomers of 2-methyl-2-(4-[3-[1-(4-methylbenzyl)-5-oxo-4,5-dihydro-1H-[1,2,4]triazol—3-yl]propyl]phenoxy)propionic acid, a potent and selective peroxisome proliferator-activated receptor alpha agonist. Journal of Labelled Compounds and Radiopharmaceuticals 50(8):693-701 (2007).
Messmer et al. Abstract No. 3879 Inhibition of fatty acid oxidation leads to apoptosis of resting and proliferating chronic lymphocytic leukemia cells in vitro, 54th ASH Annual Meeting and Exposition, Atlanta, GA, Oral and Poster Abstracts. (Dec. 8-11, 2012) (1 pg.).
Millar et al. Potent and selective PPARα agonist LY518674 upregulates both ApoA-I production and catabolism in human subjects with the metabolic syndrome. Arterioscler Throm Vasc Biol 29(1):140-146 (2009).
Moenes et al. Synthesis and antimicrobial activity of certain pyradazines. Alex J Pharm Sci 10(1):35-38 (1996).

PCT/US2013/029713 International Preliminary Report on Patentability dated Sep. 9, 2014.
PCT/US2013/029713 International Search Report and Written Opinion dated Jun. 28, 2013.
PCT/US2013/074197 International Search Report and Written Opinion dated Mar. 31, 2014.
PCT/US2014/054108 International Search Report and Written Opinion dated Dec. 26, 2014.
Rao et al. Synthesis of substituted 2,4-dihydro[1,2,4,]-triazol-3-ones. Indian Journal of Heterocyclic Chemistry 20(1):9-12 (2010).
Rashad et al. Synthesis of new quinoline derivatives as inhibitors of human tumor cells growth. Archiv der Pharmazie 343(8):440-448 (2010).
Soliman et al. Heterocyclic synthesis with biologically active S-(6-aryl pyridazin 3-yl) thioglycollic acid hydrazides. Egypt J Chem 50(4):443-453 (2007).
Tumosiene et al. Synthesis of azole derivatives from 3-phenylaminopropanohydrazide and evaluation of their antimicrobial efficacy. Heterocycles 78(1):59-70 (2009).
Tumosiene et al. Synthesis of azoles from 3,3'-[(4-alkoxyphenyl)imino]bis(propanoic acid hydrazides). Monatsh Chem 140(12):1523-1528 (2009).
Tumosiene et al. Synthesis of azoles from 3,3'-(arylimino)bis[propanoyl hydrazides]. Chemistry of Heterocyclic Compounds 43(9):1148-1153 (2007).
Tutoveanu et al. New semi—and thiosemicarbazides and cyclization products. Revistade Chimie 24(3):155-158 (1973) (English Abstract).
U.S. Appl. No. 14/383,096 Office Action dated Dec. 17, 2015.
U.S. Appl. No. 14/383,096 Office Action dated May 3, 2016.
U.S. Appl. No. 14/654,225 Office Action dated Oct. 7, 2016.
U.S. Appl. No. 14/916,860 Office Action dated Dec. 29, 2016.
Xu et al. Design and synthesis of a potent and selective triazolone-based peroxisome proliferator-activated receptor alpha agonist. J Med Chem 46:5121-5124 (2003).

* cited by examiner

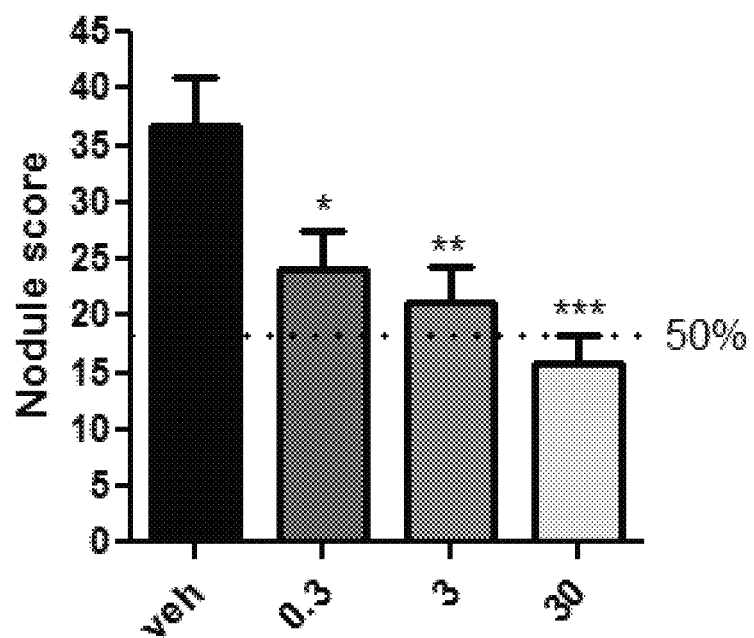

TRIAZOLONE COMPOUNDS AND USES THEREOF

RELATED APPLICATIONS

This application is a continuation of U.S. application Ser. No. 14/654,225, filed Jun. 19, 2015, which is the U.S. National Phase Application of PCT/US2013/074197, filed Dec. 10, 2013, which claims the benefit of U.S. Provisional Application No. 61/739,906, filed Dec. 20, 2012, the content of each of these applications is hereby incorporated by reference in their entirety, including any drawings.

FIELD OF THE INVENTION

This invention is directed to novel triazolones, or pharmaceutically acceptable salts thereof, useful in the treatment of prostate, breast, colon, pancreatic, human chronic lymphocytic leukemia, melanoma and other cancers. The invention disclosed herein is further directed to methods of treating prostate, breast, ovarian, liver, kidney, colon, pancreatic, human chronic lymphocytic leukemia, melanoma and other cancers comprising administration of selective PPARα antagonists. The compounds and pharmaceutical compositions of the invention are also useful in the treatment of viral infections, such as HCV infections and HIV infections.

BACKGROUND OF THE INVENTION

While tremendous strides have been made in the treatment of various cancers, in many cases, cancer treatment continues to be a matter of administering one or more anti-cancer agents that are marginally less chemotoxic to healthy cells than they are to the cancer in question. In recognition of this problem, there has been substantial research effort aimed at identifying, understanding and taking advantage of phenotypical behavior peculiar to certain cancer cells. It has long been observed that most cancer cell types generate energy for cellular processes through aerobic glycolysis rather than through oxidative phosphorylation as found in the normal cell. This process, which became known as the "Warburg effect", is highly energy inefficient and requires cancer cell mitochondria to resort to glucose fermentation to make up the energy deficit. Since perhaps the mid-1990's researchers have sought to identify methods of treating cancer that take advantage of the "Warburg effect" and associated aspects of cancer cell mitochondrial metabolism. See, for example, Wang, et al., Small mitochondrial-targeting molecules as anti-cancer agents, Mol. Aspects Med. 2010 February; 31(1): 75-92.

Samudio, et al., J. Clin. Invest. 120: 142-156 (2010), disclosed that in certain leukemia cell lines "mitochondrial uncoupling—the continuing reduction of oxygen without ATP synthesis—has recently been shown in leukemic cells to circumvent the ability of oxygen to inhibit glycolysis, and may promote the metabolic preference for glycolysis by shifting from pyruvate oxidation to fatty acid oxidation (FAO)." Samudio, et. al., also provided data indicating that inhibition of FAO could sensitize human leukemia cells to apoptosis, and further that inhibition of FAO may prove useful in the treatment of leukemia.

PPARα is known to be an important regulator of fatty acid oxidation. See Pyper, et al., Nucl. Recept. Signal. 8:e002, e002 (2010). It has been reported that the expression of the PPARα gene can be higher in human chronic lymphocyte leukemia (CLL) making this cancer type sensitive to therapies aimed at reducing FAO (Samudio et al., J. Clin. Invest. 120:142-156 (2010)). This effect may generalize to several cancer types. For example, ovarian cancer and breast cancer (Linher-Melville et al., 2011, BMC, 4; 11:56), thrive in an adipose rich environment and as a result can be negatively impacted by targeted therapies that reduce fatty acid metabolism (Nieman et al., 2011, Nat Med. 2011 Oct. 30; 17(11):1498-503). Still other cancers that rely on FAO include prostate cancer (Liu, Prostate Cancer Prostatic Dis. 2006; 9(3):230-4), colon cancer (Holla et al., 2011, JCB 286(34):30003-30009), pancreatic cancer (Khasawneh et al., 2009, PNAS 106(9):3354-3359) and lung cancer (Zaugg et al., 2011, Genes and Development, 25:1041-1051).

GW6471 (Xu et al., Nature 415, 813-817 (2002) and MK-866 (Kehrer et al., Biochem. J. 356, 899-906 (2001) have been identified as antagonists of PPARα. Moreover, MK-866, whose primary activity is as an inhibitor of FLAP, has been disclosed to induce apoptosis in a human chronic lymphocytic leukemia cell line in a FLAP-independent manner; and has also been disclosed to induce apoptosis in prostate and glioblastoma cell lines.

It is our belief that in cancers that rely heavily on FAO, antagonism of PPARα by small molecules provides a panoply of anti-cancer treatment opportunities to: reduce or halt proliferation; decrease or reverse immunosupression; enhance apoptosis; and increase susceptibility of cancerous cells to other anti-cancer agents. These cancers include prostate, breast, colon and pancreatic cancer, among others.

Chronic myeloid leukemia (CML) is model of hematopoietic stem cell (HSC) disease. In 2008, Ito et al. disclosed evidence linking the loss of promyelocytic leukemia (PML) gene expression with favorable outcomes in CML (Nature, 2008 Jun. 19; 453 (7198) 1072-1078). More recently Ito et al. disclosed that in the PML pathway, loss of PPARδ and accompanying inhibition of mitochondrial FAO induced loss of hematopoietic stem cell (HSC) maintenance (Nature Medicine, doi:10.1038/nm.2882). Moreover, Carracedo et al. disclosed that whereas PML expression allowed luminal filling in 3D basement membrane breast cancer, the effect was reversed by inhibition of FAO (J. Clin. Invest. 2012; 122(9):3088-3100). This and other evidence supports our view that inhibition of fatty acid oxidation, via antagonism of PPAR's (including PPARα), will prove effective in inhibiting asymmetric leukemia stem cell differentiation, and therefore, prove effective in preventing the onset of and/or recurrence of acute and chronic myeloid leukemia, as well as other cancers.

PPARα antagonists have also been shown to inhibit HCV replication and thereby prove useful in the treatment of HCV infection (Rakic et al., Chem. & Biol. 13, 23-30 (January 2006)). In some embodiments, PPAR modulators have been shown to inhibit viral transcription and replication and thereby prove useful in the treatment of viral diseases (Capeau et al., PPAR Research Volume 2009, Article ID 393408, 2 pages). In some embodiments, PPARα antagonists are useful in the treatment of HIV infection. PPARα antagonists have also been disclosed to be useful in the treatment of metabolic disorders (WO2012/027482A2). Metabolic disorders include, but are not limited to diabetes, obesity, metabolic syndrome, impaired glucose tolerance, syndrome X, and cardiovascular disease.

SUMMARY OF THE INVENTION

The invention disclosed herein is directed to compounds of Formula I

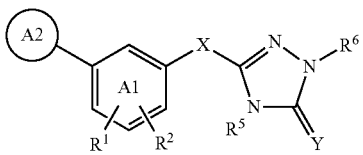

I and pharmaceutically acceptable salts thereof, which are useful in the treatment of prostate, breast, colon, pancreatic, human chronic lymphocytic leukemia, melanoma, and other cancers. The invention also includes pharmaceutical compositions comprising a therapeutically effective amount of compound of Formula I, or a pharmaceutically acceptable salt thereof. The invention disclosed herein is also directed to methods of treating prostate, breast, ovarian, liver, kidney, colon, pancreatic, human chronic lymphocytic leukemia, melanoma and other cancers. The invention disclosed herein is further directed to methods of treating prostate, breast, ovarian, liver, kidney, colon, pancreatic, human chronic lymphocytic leukemia, melanoma and other cancers through the administration of a therapeutically effective amount of a selective PPARα antagonist. The compounds and pharmaceutical compositions of the invention are also useful in the treatment of viral infections, such as HCV infections and HIV infections.

BRIEF DESCRIPTION OF THE DRAWINGS

FIG. 1 shows the ability of Example 6 to inhibit the metastasis of B16F10 melanoma cells to the lung.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE INVENTION

In one aspect the invention is directed to a compound of Formula I

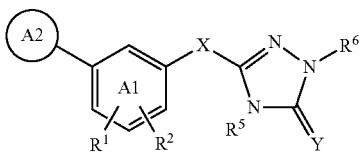

Formula I or a pharmaceutical acceptable salt thereof wherein:
A1 is phenyl or a 6-membered heteroaromatic ring having 1, 2 or 3 N in the heteroaromatic ring;
A2 is selected from A2a or A2b

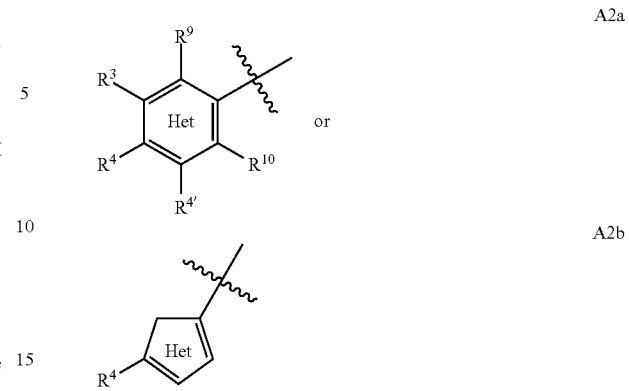

wherein A2a is phenyl or a 6 membered heteroaromatic ring having 1, 2 or 3 N in the heteroaromatic ring, and A2b is a 5 membered heteroaromatic ring having 1, 2 or 3 heteroatoms independently selected from O, S and N;
X is selected from the group consisting of $-(CH_2)_m-$, $-(CH_2)_m-O-(CH_2)_n-$, $-(CH_2)_m-NH-(CH_2)_n-$, $-(CH_2)_m-S(=O)_o-(CH_2)_n-$, optionally mono- or di-substituted with halogen, wherein m and n are independently 0, 1, 2, 3 or 4, and each o is independently 0, 1 or 2;
Y is O or S;
$R^1$ and $R^2$ are each independently selected from the group consisting of:
  (a) hydrogen,
  (b) halogen,
  (c) CN,
  (d) $CF_3$,
  (e) $-C_{1-6}$alkyl,
  (f) $-C_{1-6}$alkyl-C(=O)OH,
  (g) $-O-(R^7)$,
  (h) $-S(=O)_oR^7$,
  (i) $-N(R^7)(R^8)$,
  (j) $-N(R^7)-C(=O)-(R^8)$,
  (k) $-N(R^7)-C(=O)-O-(R^8)$,
  (l) $-N(R^7)S(=O)_2(R^8)$,
  (m) $-C_{3-6}$cycloalkyl,
  (n) $-C(=O)(R^7)$,
  (o) aryl,
  (p) heteroaryl,
  (q) $-OC(=O)N(R^7)(R^8)$,
  (r) $-S(=O)_2N(R^7)(R^8)$,
  (s) $-C(=O)N(R^7)(R^8)$, and
  (t) $-C(R^7)(R^8)OH$,
wherein the alkyl portion of choices (e) and (f), and the cycloalkyl portion of choice (m) are optionally substituted with halogen, and
wherein the aryl of choice (o) and the heteroaryl of choice (p) are optionally mono- or di-substituted with substituents selected from halogen, nitro, $C_{1-6}$alkyl, $C_{1-6}$alkoxy, halo $C_{1-6}$alkyl, $C_{3-6}$cycloalkyl, $C_{3-6}$cycloalkoxy, $-NH(C_{1-6}$alkyl), $-NH(C_{3-6}$cycloalkyl), $-N(C_{1-6}$alkyl)$_2$, $-N(C_{3-6}$cycloalkyl)$_2$, $-S(=O)_oC_{1-6}$alkyl, $-S(=O)_oC_{3-6}$cycloalkyl, and CN;
$R^3$ is selected from the group consisting of:
  (a) hydrogen,
  (b) halogen,
  (c) CN,
  (d) $CF_3$,
  (e) $-C_{1-6}$alkyl,
  (f) $-C_{1-6}$alkyl-C(=O)OH, (g) —O—($R^7$),
(h) —S(=O)$_o R^7$,
(i) —N($R^7$)($R^8$),
(j) —N($R^7$)—C(=O)—($R^8$),
(k) —N($R^7$)—C(=O)—O—($R^8$),
(l) —N($R^7$)S(=O)$_2$($R^8$),
(m) —C$_{3-6}$-cycloalkyl,
(n) —C(=O)($R^7$),
(o) aryl,
(p) heteroaryl,
(q) —OC(=O)N($R^7$)($R^8$),
(r) —S(=O)$_2$N($R^7$)($R^8$),
(s) —C(=O)N($R^7$)($R^8$),
(t) —C($R^7$)($R^8$)OH,
(u) —NHC(=O)—N($R^7$)($R^8$),
(v) —C$_{3-6}$cycloalkyl-COOH,
(w) heterocycle, and
(x) —C$_{1-6}$alkylC(=O)—N($R^7$)($R^8$),
wherein the alkyl portion of choices (e), (f) and (x), and the cycloalkyl portion of choices (m) and (v) are optionally substituted with halogen or hydroxyl, and
wherein the aryl of choice (o), the heteroaryl of choice (p), and the heterocycle of choice (w) are optionally mono- or di-substituted with substituents selected from halogen, nitro, C$_{1-6}$alkyl, C$_{1-6}$alkoxy, halo C$_{1-6}$alkyl, C$_{3-6}$cycloalkyl, C$_{3-6}$cycloalkoxy, —NH(C$_{1-6}$alkyl), —NH(C$_{3-6}$cycloalkyl), —N(C$_{1-6}$alkyl)$_2$, —N(C$_{3-6}$cycloalkyl)$_2$, —S(=O)$_o$C$_{1-6}$alkyl, —S(=O)$_o$C$_{3-6}$cycloalkyl, hydroxyl and CN;
$R^4$ and $R^{4'}$ are each independently selected from the group consisting of:
(a) hydrogen,
(b) —N($R^7$)($R^8$),
(c) —N($R^7$)S(=O)$_2 R^8$,
(d) —N($R^7$)—C(=O)$R^8$,
(e) —N(R')C(=O)O$R_8$,
(f) —S(=O)$_o R^7$,
(g) —S(=O)$_2$N($R^7$)($R^8$),
(h) —C(=O)$R^7$,
(i) —C(=O)N($R^7$)($R^8$),
(j) —OC(=O)N($R^7$)($R^8$),
(k) —O—$R^7$,
(l) —C($R^7$)($R^8$)OH,
(m) —C$_{1-4}$alkyl-C(=O)NHS(=O)$_2 R^7$,
(n) —C$_{1-4}$alkyl-S(=O)$_2$NHC(=O)$R^7$,
(o) —C$_{1-4}$alkyl-C(=O)—N($R^7$)($R^8$),
(p) —C$_{1-4}$alkyl-N($R^7$)C(=O)($R^8$),
(q) —C$_{1-4}$alkyl-N($R^7$) S(=O)$_2$($R^8$),
(r) —C$_{1-4}$alkyl-S(=O)$_2$N($R^7$)($R^8$),
(s) —C$_{1-4}$alkyl-N($R^7$)C(=O)O($R^8$)
(t) —C$_{1-4}$alkyl-O—C(=O)N($R^7$)($R^8$)
(u) —C$_{1-4}$alkyl-C(=O)($R^7$),
(v) —C$_{1-4}$alkyl-C($R^7$)($R^8$)OH,
(w) —C$_{1-4}$alkyl-O($R^7$),
(x) —C$_{1-6}$alkyl-C(=O)OH,
(y) —C$_{2-6}$alkenyl-C(=O)OH,
(z) —C$_{3-6}$cycloalkyl-C(=O)OH,
(aa) —C$_{3-6}$cycloalkyl-C(=O)NHS(=O)$_2 R^7$,
(bb) —C$_{3-6}$cycloalkyl-S(=O)$_2$NHC(=O)$R^7$,
(cc) —C$_{3-6}$cycloalkyl-C(=O)—N($R^7$)($R^8$),
(dd) —C$_{3-6}$cycloalkyl-N($R^7$)C(=O)($R^8$),
(ee) —C$_{3-6}$cycloalkyl-N($R^7$)S(=O)$_2$($R^8$),
(ff) —C$_{3-6}$cycloalkyl-S(=O)$_2$N($R^7$)($R^8$),
(gg) —C$_{3-6}$cycloalkyl-N($R^7$)C(=O)O($R^8$),
(jj) —C$_{3-6}$cycloalkyl-C($R^7$)($R^8$)OH,
(kk) —C$_{3-6}$cycloalkyl-O($R^7$),
(ll) —C(=O)OH,
(mm) aryl,
(nn) heteroaryl,
(oo) —C(=O)N($R^7$)S(=O)$_2$($R^8$),
(pp) —S(=O)$_2$N($R^7$)C(=O)($R^8$),
(qq) —NHS(=O)$_2$N($R^7$)($R^8$),
(rr) —NHC(=O)N($R^7$)($R^8$),
(ss) —CH(OH)—C(=O)—N($R^7$)($R^8$),
(tt) —C(=O)—C(=O)—N($R^7$)($R^8$),
(uu) —C$_{3-6}$-cycloalkyl,
(vv) —CF$_3$,
(ww) —C$_{1-6}$alkyl N($R^7$)($R^8$),
(xx) -heterocycle,
(yy) —C$_{1-6}$alkyl,
(zz) halogen, and
(aaa) —O—C$_{1-6}$alkyl-N($R^7$)($R^8$),
wherein the alkyl portion of choices (m), (n), (o), (p), (q), (r), (s), (t), (u), (v), (w), (x), (ww), (yy) and (aaa), the alkenyl portion of choice (y), and the cycloalkyl portion of choices (z), (aa), (bb), (cc), (dd), (ee), (ff), (gg), (hh), (ii), (jj), (kk) and (uu), are optionally mono- or di-substituted with halogen, CN, aryl, C$_{1-6}$alkyl, halo C$_{1-6}$alkyl, C$_{3-6}$cycloalkyl, C$_{1-6}$alkoxy, or C$_{3-6}$cycloalkoxy, and wherein the aryl of choice (mm), the heteroaryl of choice (nn), and the heterocycle of choice (xx) are optionally mono- or di-substituted with substituents selected from halogen, nitro, C$_{1-6}$alkyl, C$_{1-6}$alkoxy, halo C$_{1-6}$alkyl, C$_{3-6}$cycloalkyl, C$_{3-6}$cycloalkoxy, —NH(C$_{1-6}$alkyl), —NH(C$_{3-6}$cycloalkyl), —N(C$_{1-6}$alkyl)$_2$, —N(C$_{3-6}$cycloalkyl)$_2$, —S(=O)$_o$C$_{1-6}$alkyl, —S(=O)$_o$C$_{3-6}$cycloalkyl, hydroxyl and CN, or wherein $R^3$ and $R^4$ or $R^4$ and $R^{4'}$ are joined together to form a 5- or 6-membered heterocyclic ring, said ring having one heteroatom selected from O and N, wherein said ring is optionally substituted with —C(=O)OH, or —C$_{1-6}$alkyl-C(=O)OH, with the proviso that at least one of $R^3$, $R^4$ and $R^{4'}$ is other than hydrogen; $R^5$ is selected from the group consisting of:
(a) hydrogen,
(b) —C$_{1-6}$alkyl,
(c) —C$_{1-4}$alkyl($R^7$),
(d) aryl,
(e) heteroaryl,
(f) —C$_{3-6}$cycloalkyl,
(g) —C$_{3-6}$cycloalkyl($R^7$),
(h) —C$_{3-6}$cycloalkyl-O($R^7$),
(i) —C$_{1-4}$alkyl-C$_{3-6}$cycloalkyl,
(j) —C$_{1-6}$alkoxy, and
(k) —C$_{3-6}$cycloalkoxy,
wherein the alkyl portion of choices (b), (c), (i) and (j), the cycloalkyl portion of choices (f), (g), (h), (i) and (k) are optionally substituted with halogen or C$_{1-4}$alkyl, and
wherein the aryl of choice (d) and the heteroaryl of choice (e), are optionally mono- or di-substituted with substituents selected from halogen, nitro, C$_{1-6}$alkyl, CF$_3$, C$_{1-6}$alkoxy, halo C$_{1-6}$alkyl, aryl, heteroaryl, C$_{3-6}$cycloalkyl, C$_{3-6}$cycloalkoxy, and CN;
$R^6$ is selected from the group consisting of:
(a) hydrogen,
(b) —C$_{1-6}$alkyl,
(c) —C$_{1-6}$alkylaryl,
(d) —C$_{1-6}$alkylheteroaryl,
(e) —S(=O)$_o$C$_{1-6}$alkyl($R^7$),
(f) —C(=O)C$_{1-6}$alkyl($R^7$),
(g) —C$_{3-6}$-cycloalkyl,
(h) aryl,
(i) hetereoaryl,
(j) —C(=O)C$_{3-6}$cycloalkyl($R^7$),
(k) —S(=O)$_o$C$_{3-6}$cycloalkyl($R^7$), and
(l) —C$_{1-6}$alkyl($R^7$), wherein the alkyl portion of choices (b), (c), (d), (e), (f), and (l) and the cycloalkyl portion of choices (g), (j), and (k), are optionally substituted with halogen or $C_{1-4}$alkyl, and wherein the aryl portion of choices (c) and (h), and the heteroaryl portion of choices (d) and (i), are optionally mono- or di-substituted with substituents selected from halogen, nitro, —$CF_3$, $C_{1-6}$alkyl, $C_{1-6}$alkoxy, halo $C_{1-6}$alkyl, $C_{3-6}$cycloalkyl, $C_{3-6}$cycloalkoxy, aryl, heteroaryl, heterocycle optionally substituted with halogen, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_o$$C_{1-6}$alkyl, S(=O)$_o$$C_{3-6}$cycloalkyl, and CN;

$R^7$ and $R^8$ are each independently selected from the following:
   (a) hydrogen,
   (b) —$C_1$ alkyl,
   (c) —$C_{3-6}$cycloalkyl,
   (d) -aryl,
   (e) -heteroaryl,
   (f) —$C_{1-6}$alkylaryl,
   (g) —$C_{1-6}$alkylheteroaryl,
   (h) —C(=O)$C_{1-6}$alkyl,
   (i) —S(=O)$_o$-aryl,
   (j) —$C_{1-6}$alkyl-$C_{3-6}$cycloalkyl, and
   (k) $CF_3$, wherein the alkyl of choices (b), (f), (g), (h), and (j), and the cycloalkyl of choices (c) and (j), are each optionally mono-, di- or tri-substituted with halogen, and wherein the aryl portion of choices (d), (f) and (i), and the heteroaryl portion of choices (e) and (g), are each optionally mono- or di-substituted with substituents selected from halogen, —C(=O)OH, —$CF_3$, —NHC(=O)$CH_3$, nitro, $C_{1-6}$alkyl, $C_{1-6}$alkoxy, halo $C_{1-6}$alkyl, $C_{3-6}$cycloalkyl, $C_{3-6}$cycloalkoxy, —NH($C_{1-3}$alkyl), —NH($C_{3-6}$cycloalkyl), —N($C_{1-3}$alkyl)$_2$, —N($C_{3-6}$cycloalkyl)$_2$, —S(=O)$_o$$C_{1-4}$alkyl, S(=O)$_o$$C_{3-6}$cycloalkyl, aryl, heteroaryl, hydroxyl, and CN;

$R^9$ and $R^{10}$ are each independently selected from the following
   (a) hydrogen,
   (b) —$C_{1-6}$alkyl,
   (c) —$C_{3-6}$-cycloalkyl,
   (d) halogen,
   (e) —O$C_{3-6}$cycloalkyl,
   (f) $CF_3$, and
   (g) —$C_{1-6}$alkoxy, wherein the alkyl portion of choice (b) and the cycloalkyl portion of choices (c) and (e), are each optionally mono-, di- or tri-substituted with halogen. In the alternative, choice (g) of $R^9$ and $R^{10}$ may also be mono-, di- or tri-substituted with halogen.

Within this aspect there is a genus wherein:
X is selected from the group consisting of —($CH_2$)$_m$—, and —($CH_2$)$_m$—O—($CH_2$)$_n$—, optionally mono- or di-substituted with halogen, where m+n is 2, 3 or 4.

Within this genus there is a sub-genus wherein:
X is selected from —$CH_2CH_2CH_2$—, or —$CF_2CH_2CH_2$—.

Within this aspect there is an alternative genus wherein:
X is selected from the group consisting of —($CH_2$)$_m$—, and —($CH_2$)$_m$—O—($CH_2$)$_n$—, optionally mono- or di-substituted with halogen, where m+n is 1, 2, 3 or 4.

Within this alternative genus there is a sub-genus wherein:
X is selected from —$CH_2CH_2CH_2$—, —$CF_2CH_2CH_2$—, or —$OCH_2$—.

Within this aspect there is a genus wherein:
A1 is a substituted phenyl or substituted pyridine.

Within this genus there is a sub-genus wherein:
A2 is A2a.

Within this sub-genus there is a class wherein:
A2a is a substituted phenyl, substituted pyrimidine, substituted pyrazine, or substituted pyridine.

Within this aspect these is a genus wherein:
Y is O.

Within this aspect there is a genus wherein:
$R^1$ and $R^2$ are each independently selected from the group consisting of:
   (a) hydrogen,
   (b) halogen,
   (c) CN,
   (d) $CF_3$,
   (e) —$C_{1-6}$alkyl,
   (f) —O—($R^7$),
   (g) —$C_{3-6}$-cycloalkyl, and
   (h) —N($R^7$)($R^8$), wherein the alkyl portion of choice (e) and the cycloalkyl portion of choice (g) are optionally substituted with halogen.

Within this genus there is a sub-genus wherein:
$R^1$ and $R^2$ are each independently selected from:
   (a) hydrogen,
   (b) halogen,
   (c) $CF_3$,
   (d) —$C_{1-6}$alkyl, and
   (e) —O—($R^7$), wherein the alkyl portion of choice (d) is optionally substituted with halogen.

Within this sub-genus there is a class wherein $R^1$ and $R^2$ are each hydrogen.

Within this aspect there is a genus wherein:
$R^3$ is selected from the group consisting of:
   (a) hydrogen,
   (b) halogen,
   (c) $CF_3$,
   (d) —$C_{1-6}$alkyl,
   (e) —O—($R^7$),
   (f) —S(=O)$_o$$R^7$,
   (g) —$C_{3-6}$-cycloalkyl,
   (h) aryl,
   (i) heteroaryl,
   (j) —S(=O)$_2$N($R^7$)($R^8$),
   (k) —C($R^7$)($R^8$)OH,
   (l) heterocycle, and
   (m) —N($R^7$)S(=O)$_2$($R^8$), wherein the alkyl portion of choice (d) and the cycloalkyl portion of choice (g) are optionally substituted with halogen or hydroxyl, and wherein the aryl of choice (h), the heteroaryl of choice (i), and the heterocycle of choice (l) are optionally mono- or di-substituted with substituents selected from halogen, nitro, $C_{1-6}$alkyl, $C_{1-6}$alkoxy, halo $C_{1-6}$alkyl, $C_{3-6}$cycloalkyl, $C_{3-6}$cycloalkoxy, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_o$$C_{1-6}$alkyl, —S(=O)$_o$$C_{3-6}$cycloalkyl, hydroxyl and CN.

Within this genus there is a sub-genus wherein:
$R^3$ is selected from the group consisting of:
   (a) hydrogen,
   (b) —O—($R^7$),
   (c) —N($R^7$)S(=O)$_2$($R^8$), and
   (d) —$C_{1-6}$-alkyl, wherein the alkyl portion of choice (d) is optionally substituted with halogen or hydroxyl.

Within this aspect there is a genus wherein:
$R^4$ and $R^{4'}$ are each independently selected from the group consisting of:
   (a) hydrogen,
   (b) —N($R^7$)S(=O)$_2R^8$, (c) —N(R$^7$)—C(=O)R$^8$,
(d) —S(=O)$_o$R$^7$,
(e) —S(=O)$_2$N(R$^7$)(R$^8$),
(f) —C(=O)N(R$^7$)(R$^8$),
(g) —O—(R$^7$),
(h) —C(R$^7$)(R$^8$)OH,
(i) —C$_{1-4}$alkyl-C(=O)NHS(=O)$_2$R$^7$,
(j) —C$_{1-4}$alkyl-S(=O)$_2$NHC(=O)R$^7$,
(k) —C$_{1-4}$alkyl-C(=O)—N(R$^7$)(R$^8$),
(l) —C$_{1-4}$alkyl-N(R$^7$)C(=O)(R$^8$),
(m) —C$_{1-4}$alkyl-N(R$^7$) S(=O)$_2$(R$^8$),
(n) —C$_{1-4}$alkyl-S(=O)$_2$N(R$^7$)(R$^8$),
(o) —C$_{1-4}$alkyl-C(R$^7$)(R$^8$)OH,
(p) —C$_{1-4}$alkyl-O(R$^7$),
(q) —C$_{1-6}$alkyl-C(=O)OH,
(r) —C$_{2-6}$alkenyl-C(=O)OH,
(s) —C$_{3-6}$cycloalkyl-C(=O)OH,
(t) —C$_{3-6}$cycloalkyl-C(=O)NHS(=O)$_2$R$^7$,
(u) —C$_{3-6}$cycloalkyl-S(=O)$_2$NHC(=O)R$^7$,
(v) —C$_{3-6}$cycloalkyl-C(=O)—N(R$^7$)(R$^8$),
(w) —C$_{3-6}$-cycloalkyl-N(R$^7$)S(=O)$_2$(R$^8$),
(x) —C$_{3-6}$cycloalkyl-S(=O)$_2$N(R$^7$)(R$^8$),
(y) —C$_{3-6}$cycloalkyl-N(R$^7$)C(=O)O(R$^8$),
(z) —C$_{3-6}$cycloalkyl 1-C(R$^7$)(R$^8$)OH,
(aa) —C$_{3-6}$cycloalkyl-O(R$^7$),
(bb) —C(=O)OH,
(cc) aryl,
(dd) heteroaryl,
(ee) —C(=O)N(R$^7$)S(=O)$_2$(R$^8$),
(ff) —S(=O)$_2$N(R$^7$)C(=O)(R$^8$),
(gg) —NHS(=O)$_2$N(R$^7$)(R$^8$),
(hh) —NHC(=O)N(R$^7$)(R$^8$),
(ii) —C$_{3-6}$cycloalkyl,
(jj) CF$_3$,
(kk) heterocycle,
(ll) —C$_{1-6}$-alkyl, and
(mm) halogen,
wherein the alkyl portion of choices (i), (j), (k), (l), (m), (n), (o), (p), (q), and (ll), the alkenyl portion of choice (r), and the cycloalkyl portion of choices (s), (t), (u), (v), (w), (x), (y), (z), and (aa) are optionally mono- or di-substituted with halogen, CN, aryl, C$_{1-6}$alkyl, halo C$_{1-6}$alkyl, C$_{3-6}$cycloalkyl, C$_{1-6}$alkoxy, or C$_{3-6}$cycloalkoxy and,
wherein the aryl of choice (cc), the heteroaryl of choice (dd), and the heterocycle of choice (kk) are optionally mono- or di-substituted with substituents selected from halogen, hydroxyl, nitro, C$_{1-6}$alkyl, C$_{1-6}$alkoxy, halo C$_{1-6}$alkyl, C$_{3-6}$cycloalkyl, C$_{3-6}$cycloalkoxy, —NH(C$_{1-6}$alkyl), —NH(C$_{3-6}$cycloalkyl), —N(C$_{1-6}$alkyl)$_2$, —N(C$_{3-6}$cycloalkyl)$_2$, —S(=O)$_o$C$_{1-6}$alkyl, —S(=O)$_o$C$_{3-6}$cycloalkyl, and CN. In the alternative, choice (ii) of R$^4$ and R$^{4'}$ may also be mono- or di-substituted with halogen, CN, aryl, C$_{1-6}$alkyl, halo C$_{1-6}$alkyl, C$_{3-6}$-cycloalkyl, C$_{1-6}$alkoxy, or C$_{3-6}$cycloalkoxy halogen.

Within this genus there is a sub-genus wherein:
R$^4$ and R$^{4'}$ are each independently selected from the group consisting of:
(a) hydrogen,
(b) —N(R$^7$)S(=O)$_2$R$^8$,
(c) —N(R$^7$)—C(=O)R$^8$,
(d) —O—(R$^7$),
(e) —C(R$^7$)(R$^8$)OH,
(f) —C$_{1-4}$alkyl-S(=O)$_2$NHC(=O)R$^7$,
(g) —C$_{1-4}$alkyl-N(R$^7$) S(=O)$_2$(R$^8$),
(h) —C$_{1-4}$alkyl-S(=O)$_2$N(R$^7$)(R$^8$),
(i) —C$_{1-4}$alkyl-O(R$^7$),
(j) —C$_{1-6}$ alkyl-C(=O)OH,
(k) —C$_{3-6}$cycloalkyl-C(=O)OH,
(l) —C$_{3-6}$cycloalky-N(R$^7$)S(=O)$_2$(R$^8$),
(m) —C$_{3-6}$cycloalkyl-S(=O)$_2$N(R$^7$)(R$^8$),
(n) —C$_{3-6}$cycloalkyl-O(R$^7$),
(o) —C(=O)OH,
(p) —C(=O)N(R$^7$) S(=O)$_2$(R$^8$),
(q) —S(=O)$_2$N(R$^7$)C(=O)(R$^8$),
(r) —NHS(=O)$_2$N(R$^7$)(R$^8$),
(s) —C$_{3-6}$cycloalkyl,
(t) CF$_3$,
(u) heterocycle,
(v) —C$_{1-6}$alkyl, and
(w) halogen,
wherein the alkyl portion of choices (f), (g), (h), (i), (j), and (v), and the cycloalkyl portion of choices (k), (l), (m), (n), and (s), are optionally mono- or di-substituted with halogen, CN, aryl, C$_{1-6}$alkyl, halo C$_{1-6}$alkyl, C$_{3-6}$cycloalkyl, C$_{1-6}$alkoxy, or C$_{3-6}$cycloalkoxy, and
wherein the heterocycle of choice (u) is optionally mono- or di-substituted with substituents selected from halogen, hydroxyl, nitro, C$_{1-6}$alkyl, C$_{1-6}$alkoxy, halo C$_{1-6}$alkyl, C$_{3-6}$cycloalkyl, C$_{3-6}$cycloalkoxy, —NH(C$_{1-6}$alkyl), —NH(C$_{3-6}$cycloalkyl), —N(C$_{1-6}$alkyl)$_2$, —N(C$_{3-6}$cycloalkyl)$_2$, —S(=O)$_o$C$_{1-6}$alkyl, —S(=O)$_o$C$_{3-6}$cycloalkyl and CN.

Within this sub-genus there is class wherein:
R$^4$ and R$^{4'}$ are each independently selected from the group consisting of:
(a) —C(R$^7$)(R$^8$)OH,
(b) —N(R$^7$)S(=O)$_2$R$^8$,
(c) —O—(R$^7$),
(d) —C$_{1-6}$alkyl-C(=O)OH,
(e) —C(=O)OH,
(f) —NHS(=O)$_2$N(R$^7$)(R$^8$),
(g) —C$_{3-6}$cycloalkyl,
(h) CF$_3$,
(i) heterocycle,
(j) —C$_{1-6}$alkyl, and
(k) halogen,
wherein the alkyl portion of choices (d) and (j), and the cycloalkyl portion of choice (g) are optionally mono- or di-substituted with halogen, CN, aryl, C$_{1-6}$alkyl, halo C$_{1-6}$alkyl, C$_{3-6}$cycloalkyl, C$_{1-6}$alkoxy, or C$_{3-6}$cycloalkoxy, and
wherein the heterocycle of choice (i) is optionally mono- or di-substituted with substituents selected from halogen, hydroxyl, nitro, C$_{1-6}$alkyl, C$_{1-6}$alkoxy, halo C$_{1-6}$alkyl, C$_{3-6}$cycloalkyl, C$_{3-6}$cycloalkoxy, —NH(C$_{1-6}$alkyl), —NH(C$_{3-6}$cycloalkyl), —N(C$_{1-6}$alkyl)$_2$, —N(C$_{3-6}$cycloalkyl)$_2$, —S(=O)$_o$C$_{1-6}$alkyl, —S(=O)$_o$C$_{3-6}$cycloalkyl, and CN.

Within this aspect there is a genus wherein:
R$^5$ is selected from the group consisting of:
(a) hydrogen,
(b) —C$_{1-6}$alkyl,
(c) —C$_{1-4}$alkyl(R$^7$),
(d) aryl,
(e) heteroaryl,
(f) —C$_{3-6}$cycloalkyl, and
(g) —C$_{1-4}$alkyl-C$_{3-6}$cycloalkyl,
wherein the alkyl portion of choices (b), (c), and (g), the cycloalkyl portion of choices (f) and (g), are optionally substituted with halogen or C$_{1-4}$alkyl, and
wherein the aryl of choice (d) and the heteroaryl of choice (e), is optionally mono- or di-substituted with substituents selected from halogen, nitro, C$_{1-6}$alkyl, CF$_3$, C$_{1-6}$alkoxy, halo C$_{1-6}$alkyl, aryl, heteroaryl, C$_{3-6}$cycloalkyl, C$_{3-6}$cycloalkoxy, and CN.

Within this genus there is a sub-genus wherein
$R^5$ is selected from the group consisting of:
  (a) hydrogen,
  (b) —$C_{1-6}$alkyl, and
  (c) —$C_{1-4}$alkyl($R^7$),
wherein the alkyl portion of choices (b) and (c) is optionally substituted with halogen or $C_{1-4}$alkyl.

Within this aspect there is a genus wherein:
$R^6$ is selected from the group consisting of:
  (a) —$C_{1-6}$alkylaryl,
  (b) —$C_{1-6}$alkylheteroaryl,
  (c) —$C_{3-6}$-cycloalkyl,
  (d) aryl,
  (e) hetereoaryl, and
  (f) —$C_{1-6}$alkyl($R^7$),
wherein the alkyl portion of choices (a), (b) and (f), and the cycloalkyl portion of choice (c) are optionally substituted with halogen or $C_{1-4}$alkyl, and
wherein the aryl portion of choices (a) and (d), and the heteroaryl portion of choices (b) and (e), are optionally mono- or di-substituted with substituents selected from halogen, nitro, $CF_3$, $C_{1-6}$alkyl, $C_{1-6}$alkoxy, halo $C_{1-6}$alkyl, $C_{3-6}$cycloalkyl, $C_{3-6}$cycloalkoxy, aryl, heteroaryl, heterocycle optionally substituted with halogen, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_o$$C_{1-6}$alkyl, —S(=O)$_o$$C_{3-6}$cycloalkyl, and CN.

Within this genus there is a sub-genus wherein:
$R^6$ is selected from the group consisting of:
  (a) —$C_{1-6}$alkylaryl,
  (b) —$C_{1-6}$alkylheteroaryl, and
  (c) —$C_{1-6}$alkyl($R^7$),
wherein the alkyl portion of choices (a), (b), and (c) is optionally substituted with halogen or $C_{1-4}$alkyl, and
wherein the aryl portion of choice (a), and the heteroaryl portion of choice (b), are optionally mono- or di-substituted with substituents selected from halogen, nitro, $CF_3$, $C_{1-6}$alkyl, $C_{1-6}$alkoxy, halo $C_{1-6}$alkyl, $C_{3-6}$ cycloalkyl, $C_{3-6}$cycloalkoxy, aryl, heteroaryl, heterocycle optionally substituted with halogen, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_o$$C_{1-6}$alkyl, —S(=O)$_o$$C_{3-6}$cycloalkyl, and CN.

Within this aspect there is a genus wherein:
$R^7$ and $R^8$ are each independently selected from the following:
  (a) hydrogen,
  (b) —$C_{1-6}$alkyl,
  (c) —$C_{3-6}$-cycloalkyl,
  (d) aryl,
  (e) heteroaryl, and
  (f) $CF_3$,
wherein the alkyl of choice (b) and the cycloalkyl of choice (c) are optionally mono-, di- or tri-substituted with halogen, and
wherein the aryl of choice (d) and the heteroaryl of choice (e) are optionally mono- or di-substituted with substituents selected from halogen, —C(=O)OH, $CF_3$, —NHC(=O)—$CH_3$, nitro, $C_{1-6}$alkyl, $C_{1-6}$alkoxy, halo $C_{1-6}$alkyl, $C_{3-6}$cycloalkyl, $C_{3-6}$cycloalkoxy, —NH($C_{1-3}$alkyl), —NH($C_{3-6}$cycloalkyl), —N($C_{1-3}$alkyl)$_2$, —N($C_{3-6}$cycloalkyl)$_2$, —S(=O)$_o$$C_{1-4}$alkyl, —S(=O)$_o$$C_{3-6}$cycloalkyl, aryl, heteroaryl, hydroxyl, and CN.

Within this aspect there is a genus wherein:
$R^9$ and $R^{10}$ are each independently
  (a) hydrogen,
  (b) —$C_{1-6}$alkyl,
  (c) halogen,
  (d) $CF_3$, and
  (e) —$C_{1-6}$alkoxy,
wherein the alkyl of choice (b) is optionally mono-, di- or tri-substituted with halogen. In the alternative, the alkyl portion of choice (e) of $R^9$ and $R^{10}$ may also be mono-, di- or tri-substituted with halogen.

Within this aspect there is a genus wherein:
X is selected from the group consisting of —(CH$_2$)$_m$—, and —(CH$_2$)$_m$—O—(CH$_2$)$_n$—, optionally mono or di-substituted with halogen, where m+n is 2, 3 or 4;
Y is O;
A1 is a substituted phenyl or substituted pyridine;
A2 is A2a;
$R^1$ and $R^2$ are each independently selected from the group consisting of:
  (a) hydrogen,
  (b) halogen,
  (c) CN,
  (d) $CF_3$,
  (e) —$C_{1-6}$alkyl,
  (f) —O—($R^7$),
  (g) —$C_{3-6}$cycloalkyl, and
  (h) —N($R^7$)($R^8$),
wherein the alkyl portion of choice (e) and the cycloalkyl portion of choice (g) are optionally substituted with halogen;
$R^3$ is selected from the group consisting of:
  (a) hydrogen,
  (b) halogen,
  (c) $CF_3$,
  (d) —$C_{1-6}$alkyl,
  (e) —O—($R^7$),
  (f) —S(=O)$_o$$R^7$,
  (g) —$C_{3-6}$-cycloalkyl,
  (h) aryl,
  (i) heteroaryl,
  (j) —S(=O)$_2$N($R^7$)($R^8$),
  (k) —C($R^7$)($R^8$)OH,
  (l) heterocycle, and
  (m) —N($R^7$)S(=O)$_2$($R^8$),
wherein the alkyl portion of choice (d) and the cycloalkyl portion of choice (g) are optionally substituted with halogen or hydroxyl, and
wherein the aryl of choice (h), the heteroaryl of choice (i), and the heterocycle of choice (l) are optionally mono- or di-substituted with substituents selected from halogen, nitro, $C_{1-6}$alkyl, $C_{1-6}$alkoxy, halo $C_{1-6}$alkyl, $C_{3-6}$cycloalkyl, $C_{3-6}$cycloalkoxy, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_o$$C_{1-6}$alkyl, —S(=O)$_o$$C_{3-6}$cycloalkyl, hydroxyl and CN;
$R^4$ and $R^{4'}$ are each independently selected from the group consisting of:
  (a) hydrogen,
  (b) —N($R^7$)S(=O)$_2$$R^8$,
  (c) —N($R^7$)—C(=O)$R^8$,
  (d) —S(=O)$_o$$R^7$,
  (e) —S(=O)$_2$N($R^7$)($R^8$),
  (f) —C(=O)N($R^7$)($R^8$),
  (g) —O—($R^7$),
  (h) —C($R^7$)($R^8$)OH,
  (i) —$C_{1-4}$alkyl-C(=O)NHS(=O)$_2$$R^7$,
  (j) —$C_{1-4}$alkyl-S(=O)$_2$NHC(=O)$R^7$,
  (k) —$C_{1-4}$alkyl-C(=O)—N($R^7$)($R^8$),
  (l) —$C_{1-4}$alkyl-N($R^7$)C(=O)($R^8$),
  (m) —$C_{1-4}$alkyl-N($R^7$) S(=O)$_2$($R^8$),
  (n) —$C_{1-4}$alkyl-S(=O)$_2$N($R^7$)($R^8$),
  (o) —$C_{1-4}$alkyl-C($R^7$)($R^8$)OH,
  (p) —$C_{1-4}$alkyl-O($R^7$), (q) —$C_{1-6}$alkyl-C(=O)OH,
(r) —$C_{2-6}$alkenyl-C(=O)OH,
(s) —$C_{3-6}$cycloalkyl-C(=O)OH,
(t) —$C_{3-6}$cycloalkyl-C(=O)NHS(=O)$_2R^7$,
(u) —$C_{3-6}$cycloalkyl-S(=O)$_2$NHC(=O)$R^7$,
(v) —$C_{3-6}$cycloalkyl-C(=O)—N($R^7$)($R^8$),
(w) —$C_{3-6}$-cycloalkyl-N($R^7$)S(=O)$_2$($R^8$),
(x) —$C_{3-6}$cycloalkyl-S(=O)$_2$N($R^7$)($R^8$),
(y) —$C_{3-6}$cycloalkyl-N($R^7$)C(=O)O($R^8$),
(z) —$C_{3-6}$cycloalkyl 1-C($R^7$)($R^8$)OH,
(aa) —$C_{3-6}$cycloalkyl-O($R^7$),
(bb) —C(=O)OH,
(cc) aryl,
(dd) heteroaryl,
(ee) —C(=O)N($R^7$)S(=O)$_2$($R^8$),
(ff) —S(=O)$_2$N($R^7$)C(=O)($R^8$),
(gg) —NHS(=O)$_2$N($R^7$)($R^8$),
(hh) —NHC(=O)N($R^7$)($R^8$),
(ii) —$C_{3-6}$cycloalkyl,
(jj) $CF_3$,
(kk) heterocycle,
(ll) —$C_{1-6}$alkyl, and
(mm) halogen,
wherein the alkyl portion of choices (i), (j), (k), (l), (m), (n), (o), (p), (q), and (ll), the alkenyl portion of choice (r), and the cycloalkyl portion of choices (s), (t), (u), (v), (w), (x), (y), (z), and (aa) are optionally mono- or di-substituted with halogen, CN, aryl, $C_{1-6}$alkyl, halo $C_{1-6}$alkyl, $C_{3-6}$-cycloalkyl, $C_{1-6}$alkoxy, or $C_{3-6}$cycloalkoxy and,
wherein the aryl of choice (cc), the heteroaryl of choice (dd), and the heterocycle of choice (kk) are optionally mono- or di-substituted with substituents selected from halogen, hydroxyl, nitro, $C_{1-6}$alkyl, $C_{1-6}$alkoxy, halo $C_{1-6}$alkyl, $C_{3-6}$cycloalkyl, $C_{3-6}$cycloalkoxy, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_o$C-alkyl, —S(=O)$_o C_{3-6}$cycloalkyl, and CN;
$R^5$ is selected from the group consisting of:
 (a) hydrogen,
 (b) —$C_{1-6}$alkyl,
 (c) —$C_{1-4}$alkyl($R^7$),
 (d) aryl,
 (e) heteroaryl,
 (f) —$C_{3-6}$cycloalkyl, and
 (g) —$C_{1-4}$alkyl-$C_{3-6}$cycloalkyl,
wherein the alkyl portion of choices (b), (c) and (g), the cycloalkyl portion of choices (f) and (g), are optionally substituted with halogen or $C_{1-4}$alkyl, and
wherein the aryl of choice (d) and the heteroaryl of choice (e), are optionally mono- or di-substituted with substituents selected from halogen, nitro, $C_{1-6}$alkyl, $CF_3$, $C_{1-6}$alkoxy, halo $C_{1-6}$alkyl, aryl, heteroaryl, $C_{3-6}$cycloalkyl, $C_{3-6}$cycloalkoxy, and CN;
$R^6$ is selected from the group consisting of:
 (a) —$C_{1-6}$alkylaryl,
 (b) —$C_{1-6}$alkylheteroaryl,
 (c) $C_{3-6}$cycloalkyl,
 (d) aryl,
 (e) hetereoaryl, and
 (f) —$C_{1-6}$alkyl($R^7$),
wherein the alkyl portion of choices (a), (b) and (f), and the cycloalkyl portion of choice (c) are optionally substituted with halogen or $C_{1-4}$alkyl, and
wherein the aryl portion of choices (a) and (d), and the heteroaryl portion of choices (b) and (e), are optionally mono- or di-substituted with substituents selected from halogen, nitro, $CF_3$, $C_{1-6}$alkyl, $C_{1-6}$alkoxy, halo $C_{1-6}$alkyl, $C_{3-6}$cycloalkyl, $C_{3-6}$cycloalkoxy, aryl, heteroaryl, heterocycle optionally substituted with halogen, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_o C_{1-6}$alkyl, —S(=)$C_{3-6}$cycloalkyl, and CN;
$R^7$ and $R^8$ are each independently selected from the following:
 (a) hydrogen,
 (b) $C_{1-6}$ alkyl,
 (c) $C_{3-6}$cycloalkyl,
 (d) aryl,
 (e) heteroaryl, and
 (f) $CF_3$,
wherein the alkyl of choice (b) and the cycloalkyl of choice (c) are optionally mono-, di- or tri-substituted with halo, and wherein the aryl of choice (d) and the heteroaryl of choice (e) are optionally mono- or di-substituted with substituents selected from halogen, —C(=O)OH, $CF_3$, —NHC(=O)—$CH_3$, nitro, $C_{1-6}$alkyl, $C_{1-6}$alkoxy, halo$C_{1-6}$alkyl, $C_{3-6}$cycloalkyl, $C_{3-6}$cycloalkoxy, —NH($C_{1-3}$alkyl), —NH($C_{3-6}$cycloalkyl), —N($C_{1-3}$alkyl)$_2$, —N($C_{3-6}$cycloalkyl)$_2$, —S(=O)$_o C_{1-4}$alkyl, —S(=O)$_o C_{3-6}$cycloalkyl, aryl, heteroaryl, hydroxyl, and CN; and
$R^9$ and $R^{10}$ are each independently
 (a) hydrogen,
 (b) —$C_{1-6}$alkyl,
 (c) halogen,
 (d) $CF_3$, and
 (e) $C_{1-6}$alkoxy,
wherein the alkyl of choice (b) is optionally mono-, di- or tri-substituted with halogen. In the alternative aspect, choice (ii) of $R^4$ and $R^{4'}$ may also be mono- or di-substituted with halogen, CN, aryl, $C_{1-6}$alkyl, halo $C_{1-6}$alkyl, $C_{3-6}$cycloalkyl, $C_{1-6}$-alkoxy, or $C_{3-6}$cycloalkoxy halogen; and the alkyl portion of choice (e) is optionally mono-, di- or tri-substituted with halogen and choice (e) of $R^9$ and $R^{10}$ may also be mono-, di- or tri-substituted with halogen Within this genus there is a sub-genus wherein:
A2 is A2a, and A2a is a substituted phenyl, substituted pyrimidine, substituted pyrazine, or substituted pyridine;
$R^1$ and $R^2$ are each independently selected from:
 (a) hydrogen,
 (b) halogen,
 (c) $CF_3$,
 (d) $C_{1-6}$alkyl, and
 (e) —O—($R^7$),
wherein the alkyl portion of choice (d) is optionally substituted with halogen;
$R^3$ is selected from the group consisting of:
 (a) hydrogen,
 (b) —O—($R^7$),
 (c) —N($R^7$)S(=O)$_2$($R^8$), and
 (d) —$C_{1-6}$-alkyl,
wherein the alkyl portion of choice (d) is optionally substituted with halogen or hydroxyl;
$R^4$ and $R^{4'}$ are each independently selected from the group consisting of:
 (a) hydrogen,
 (b) —N($R^7$)S(=O)$_2R^8$,
 (c) —N($R^7$)—C(=O)$R^8$,
 (d) —O—($R^7$),
 (e) —C($R^7$)($R^8$)OH,
 (f) —$C_{1-4}$alkyl-S(=O)$_2$NHC(=O)$R^7$,
 (g) —$C_{1-4}$alkyl-N($R^7$) S(=O)$_2$($R^8$),
 (h) —$C_{1-4}$alkyl-S(=O)$_2$N($R^7$)($R^8$),
 (i) —$C_{1-4}$alkyl-O($R^7$),
 (j) —$C_{1-6}$-alkyl-C(=O)OH,
 (k) —$C_{3-6}$cycloalkyl-C(=O)OH, (l) —C$_{3-6}$cycloalkyl-N(R$^7$)S(=O)$_2$(R$^8$),
(m) —C$_{3-6}$cycloalkyl-S(=O)$_2$N(R$^7$)(R$^8$),
(n) —C$_{3-6}$cycloalkyl-O(R$^7$),
(o) —C(=O)OH,
(p) —C(=O)N(R$^7$) S(=O)$_2$(R$^8$),
(q) —S(=O)$_2$N(R$^7$)C(=O)(R$^8$),
(r) —NHS(=O)$_2$N(R$^7$)(R$^8$),
(s) —C$_{3-6}$cycloalkyl,
(t) CF$_3$,
(u) heterocycle,
(v) —C$_{1-6}$alkyl, and
(w) halogen,
wherein the alkyl portion of choices (f), (g), (h), (i), (j), and (v), and the cycloalkyl portion of choices (k), (l), (m), (n), and (s), are optionally mono- or di-substituted with halogen, CN, aryl, C$_{1-6}$alkyl, halo C$_{1-6}$alkyl, C$_{3-6}$cycloalkyl, C$_{1-6}$alkoxy, or C$_{3-6}$cycloalkoxy, and
wherein the heterocycle of choice (u) is optionally mono- or di-substituted with substituents selected from halogen, hydroxyl, nitro, C$_{1-6}$alkyl, C$_{1-6}$alkoxy, halo C$_{1-6}$alkyl, C$_{3-6}$cycloalkyl, C$_{3-6}$cycloalkoxy, —NH(C$_{1-6}$alkyl), —NH(C$_{3-6}$cycloalkyl), —N(C$_{1-6}$alkyl)$_2$, —N(C$_{3-6}$cycloalkyl)$_2$, —S(=O)$_o$C$_{1-6}$alkyl, —S(=O)$_o$C$_{3-6}$cycloalkyl and CN;
R$^5$ is selected from the group consisting of:
(a) hydrogen,
(b) —C$_{1-6}$alkyl, and
(c) —C$_{1-4}$alkyl(R$^7$),
wherein the alkyl portion of choices (b) and (c) is optionally substituted with halogen or C$_{1-4}$alkyl;
R$^6$ is selected from the group consisting of:
(a) —C$_{1-6}$alkylaryl,
(b) —C$_{1-6}$alkylheteroaryl, and
(c) —C$_{1-6}$alkyl(R$^7$),
wherein the alkyl portion of choices (a), (b), and (c) is optionally substituted with halogen or C$_{1-4}$alkyl, and
wherein the aryl portion of choice (a), and the heteroaryl portion of choice (b), are optionally mono- or di-substituted with substituents selected from halogen, nitro, CF$_3$, C$_{1-6}$alkyl, C$_{1-6}$alkoxy, halo C$_{1-6}$alkyl, C$_{3-6}$cycloalkyl, C$_{3-6}$cycloalkoxy, aryl, heteroaryl, heterocycle optionally substituted with halogen, —NH(C$_{1-6}$alkyl), —NH(C$_{3-6}$cycloalkyl), —N(C$_{1-6}$alkyl)$_2$, —N(C$_{3-6}$cycloalkyl)$_2$, —S(=O)$_o$C$_{1-6}$alkyl, —S(=O)$_o$C$_{3-6}$cycloalkyl, and CN.
Within this sub-genus there is a class wherein:
R$^4$ and R$^{4'}$ are each independently selected from the group consisting of:
(a) —C(R$^7$)(R$^8$)OH,
(b) —N(R$^7$)S(=O)$_2$R$^8$,
(c) —O—(R$^7$),
(d) —C$_{1-6}$alkyl-C(=O)OH,
(e) —C(=O)OH,
(f) —NHS(=O)$_2$N(R$^7$)(R$^8$),
(g) C$_{3-6}$cycloalkyl,
(h) CF$_3$,
(i) heterocycle,
(j) —C$_{1-6}$alkyl, and
(k) halogen,
wherein the alkyl portion of choices (d) and (j), and the cycloalkyl portion of choice (g) are optionally mono- or di-substituted with halo, CN, aryl, C$_{1-6}$alkyl, halo C$_{1-6}$alkyl, C$_{3-6}$cycloalkyl, C$_{1-6}$alkoxy, or C$_{3-6}$cycloalkoxy, and
wherein the heterocycle of choice (i) is optionally mono- or di-substituted with substituents selected from halogen, hydroxyl, nitro, C$_{1-6}$alkyl, C$_{1-6}$alkoxy, halo C$_{1-6}$alkyl, C$_{3-6}$cycloalkyl, C$_{3-6}$cycloalkoxy, —NH(C$_{1-6}$alkyl), —NH(C$_{3-6}$cycloalkyl), —N(C$_{1-6}$alkyl)$_2$, —N(C$_{3-6}$cycloalkyl)$_2$, —S(=O)$_o$C$_{1-6}$alkyl, —S(=O)$_o$C$_{3-6}$cycloalkyl, and CN.

Within this class there is a sub-class wherein of Formula 1a

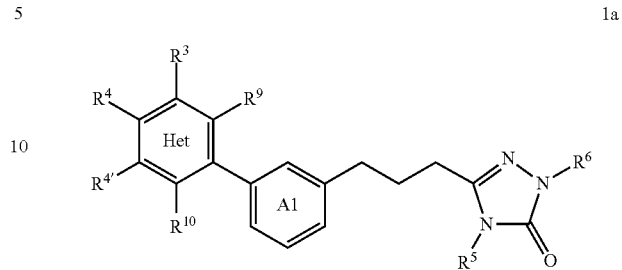

1a or a pharmaceutically acceptable salt thereof.

Within this sub-class there is a sub-sub-class wherein of Formula 1b

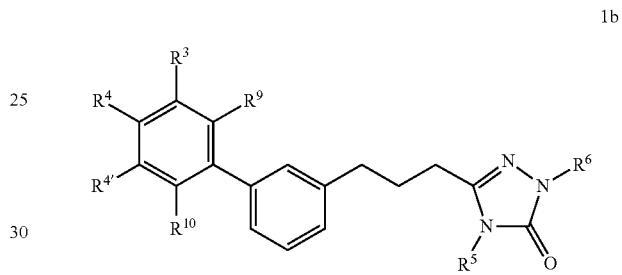

1b or a pharmaceutically acceptable salt thereof.

In some embodiments, R$^3$ is not hydrogen. In some embodiments, R$^4$ is not hydrogen. In some embodiments, R$^3$ is not hydrogen; and R$^4$ is not hydrogen.

In one aspect, described herein are the following compounds:

2-(3'-(3-(1-(4-(tert-butyl)benzyl)-4-ethyl-5-oxo-4,5-dihydro-1H-1,2,4-triazol-3-yl)propyl)-[1,1'-biphenyl]-3-yl)acetic acid, 2-(3'-(3-(1-(4-(tert-butyl)benzyl)-4-ethyl-5-oxo-4,5-dihydro-1H-1,2,4-triazol-3-yl)propyl)-[1,1'-biphenyl]-4-yl)acetic acid, 3'-(3-(1-(4-(tert-butyl)benzyl)-4-ethyl-5-oxo-4,5-dihydro-1H-1,2,4-triazol-3-yl)propyl)-[1,1'-biphenyl]-3-carboxylic acid, 3'-(3-(1-(4-(tert-butyl)benzyl)-4-ethyl-5-oxo-4,5-dihydro-1H-1,2,4-triazol-3-yl)propyl)-[1,1'-biphenyl]-4-carboxylic acid, 1-(3'-(3-(1-(4-(tert-butyl)benzyl)-4-ethyl-5-oxo-4,5-dihydro-1H-1,2,4-triazol-3-yl)propyl)-4-ethoxy-[1,1'-biphenyl]-3-yl)cyclopropanecarboxylic acid, 2-(3'-(3-(1-(4-(tert-butyl)benzyl)-4-ethyl-5-oxo-4,5-dihydro-1H-1,2,4-triazol-3-yl)propyl)-4-ethoxy-[1,1'-biphenyl]-3-yl)acetic acid, 1-(3'-(3-(1-(4-(tert-butyl)benzyl)-4-ethyl-5-oxo-4,5-dihydro-1H-1,2,4-triazol-3-yl)propyl)-[1,1'-biphenyl]-3-yl)cyclopropanecarboxylic acid, 1-(3'-(3-(1-(4-(tert-butyl)benzyl)-4-ethyl-5-oxo-4,5-dihydro-1H-1,2,4-triazol-3-yl)propyl)-[1,1'-biphenyl]-4-yl)cyclopropanecarboxylic acid, 3'-(3-(1-(4-(tert-butyl)benzyl)-4-ethyl-5-oxo-4,5-dihydro-1H-1,2,4-triazol-3-yl)propyl)-4-methoxy-[1,1'-biphenyl]-3-carboxylic acid, 3'-(3-(1-(4-(tert-butyl)benzyl)-4-ethyl-5-oxo-4,5-dihydro-1H-1,2,4-triazol-3-yl)propyl)-4-ethoxy-[1,1'-biphenyl]-3-carboxylic acid, 2-(3'-(3-(1-(4-(tert-butyl)benzyl)-4-ethyl-5-oxo-4,5-dihydro-1H-1,2,4-triazol-3-yl)propyl)-4-propoxy-[1,1'-biphenyl]-3-yl)acetic acid, N-(6-(3-(3-(1-(4-(tert-butyl)benzyl)-4-ethyl-5-oxo-4,5-dihydro-1H-1,2,4-triazol-3-yl)propyl)phenyl)pyridin-3-yl)benzenesulfonamide, 2-(3'-(3-(1-(4-(tert-butyl)benzyl)-4-ethyl-5-oxo-4,5-dihydro-1H-1,2,4-triazol-3-yl)propyl)-4-methoxy-[1,1'-biphenyl]-3-yl)acetic acid, 1-(3'-(3-(1-(4-(tert-butyl)benzyl)-4-ethyl-5-oxo-4,5-dihydro-1H-1,2,4-triazol-3-yl)propyl)-4-methy-1-[1,1'-biphenyl]-3-yl)cyclopropanecarboxylic acid, 2-(4-(benzyloxy)-3'-(3-(1-(4-(tert-butyl)benzyl)-4-ethyl-5-oxo-4,5-dihydro-1H-1,2,4-triazol-3-yl)propyl)-[1,1'-biphenyl]-3-yl)acetic acid, 2-(3'-(3-(1-(4-(tert-butyl)benzyl)-4-ethyl-5-oxo-4,5-dihydro-1H-1,2,4-triazol-3-yl)propyl)-4-(cyclopropylmethoxy)-[1,1'-biphenyl]-3-yl)acetic acid, 2-(3'-(3-(1-(4-(tert-butyl)benzyl)-4-ethyl-5-oxo-4,5-dihydro-1H-1,2,4-triazol-3-yl)propyl)-4-fluoro-[1,1'-biphenyl]-3-yl)acetic acid, 2-(3'-(3-(1-(4-(tert-butyl)benzyl)-4-ethyl-5-oxo-4,5-dihydro-1H-1,2,4-triazol-3-yl)propyl)-6-ethoxy-[1,1'-biphenyl]-3-yl)acetic acid, 3'-(3-(1-(4-(tert-butyl)benzyl)-4-ethyl-5-oxo-4,5-dihydro-1H-1,2,4-triazol-3-yl)propyl)-4-propoxy-[1,1'-biphenyl]-3-carboxylic acid, N-((3'-(3-(1-(4-(tert-butyl)benzyl)-4-ethyl-5-ox-4,5-dihydro-1H-1,2,4-triazol-3-yl)propyl)-[1,1'-biphenyl]-3-yl)methyl)benzenesulfonamide, 3-(3'-(3-(1-(4-(tert-butyl)benzyl)-4-ethyl-5-oxo-4,5-dihydro-1H-1,2,4-triazol-3-yl)propyl)-4-methoxy-[1,1'-biphenyl]-3-yl)propanoic acid, 2-(3'-(3-(1-(4-(tert-butyl)benzyl)-4-ethyl-5-oxo-4,5-dihydro-1H-1,2,4-triazol-3-yl)-1,1-difluoropropyl)-4-ethoxy-[1,1'-biphenyl]-3-yl)acetic acid, N-(6-(3-(3-(1-(4-(tert-butyl)benzyl)-4-ethyl-5-oxo-4,5-dihydro-1H-1,2,4-triazol-3-yl)-1,1-difluoropropyl)phenyl)pyridin-3-yl)benzenesulfonamide, 2-(5-(6-(3-(1-(4-(tert-butyl)benzyl)-4-ethyl-5-oxo-4,5-dihydro-1H-1,2,4-triazol-3-yl)propyl)pyridin-2-yl)-2-methoxyphenyl)acetic acid, 3-(3-(3'-(1H-tetrazol-5-yl)-[1,1'-biphenyl]-3-yl)propyl)-1-(4-(tert-butyl)benzyl)-4-ethyl-1H-1,2,4-triazol-5(4H)-one, 2-(5-(4-(3-(1-(4-(tert-butyl)benzyl)-4-ethyl-5-oxo-4,5-dihydro-1H-1,2,4-triazol-3-yl)propyl)pyrimidin-2-yl)-2-ethoxyphenyl)acetic acid, 2-(5-(6-(3-(1-(4-(tert-butyl)benzyl)-4-ethyl-5-oxo-4,5-dihydro-1H-1,2,4-triazol-3-yl)propyl)pyrimidin-4-yl)-2-ethoxyphenyl)acetic acid, (3'-(3-(1-(4-(tert-Butyl)benzyl)-4-ethyl-5-oxo-4,5-dihydro-1H-1,2,4-triazol-3-yl)propyl)-3-methoxy-[1,1'-biphenyl]-4-yl)acetic acid, (3'-(3-(1-(4-(tert-Butyl)benzyl)-4-ethyl-5-oxo-4,5-dihydro-1H-1,2,4-triazol-1-yl)propyl)-3-ethoxy-[1,1'-biphenyl]-4-yl)acetic acid, (3'-(3-(1-(4-(tert-Butyl)benzyl)-4-ethyl-5-oxo-4,5-dihydro-1H-1,2,4-triazol-3-yl)propyl)-3-propoxy-[1,1'-biphenyl]-4-yl)acetic acid, 2-(3'-(3-(1-(4-(tert-butyl)benzyl)-4-ethyl-5-oxo-4,5-dihydro-1H-1,2,4-triazol-3-yl)propyl)-3-hydroxy-[1,1'-biphenyl]-4-yl)acetic acid, 2-(3'-(3-(1-(4-(tert-butyl)benzyl)-4-ethyl-5-oxo-4,5-dihydro-1H-1,2,4-triaz-3-yl)propyl)-4-isopropoxy-[1,1'-biphenyl]-3-yl)acetic acid, 2-(3'-(3-(1-(4-(tert-butyl)benzyl)-4-ethyl-5-oxo-4,5-dihydro-1H-1,2,4-triazol-3-yl)propyl)-4-(2-(dimethylamino)ethoxy)-[1,1'-biphenyl]-3-yl)acetic acid, or a pharmaceutically acceptable salt thereof.

In another aspect the invention is directed to a pharmaceutical composition comprising a compound of Formula I, or a pharmaceutically acceptable salt thereof, and a pharmaceutically acceptable carrier.

In another aspect the invention is directed to a method of treating a cancer which is negatively impacted by diminution in its metabolism of fatty acid, through the administration of a therapeutically effective amount of a compound of Formula I, or a pharmaceutically acceptable salt thereof.

Within this aspect there is a genus wherein the cancer is selected from prostate, breast, ovarian, liver, kidney, colon, pancreatic, human chronic lymphocytic leukemia, and melanoma.

In another aspect the invention is directed to a method of treating cancer involving the administration of a therapeutically effective amount of a compound of Formula I, or a pharmaceutically acceptable salt thereof.

In another aspect the invention is directed to a method of preventing the onset of and/or recurrence of acute and chronic myeloid leukemia, as well as other cancers through the administration of a therapeutically effective amount of a compound according to Claim 1, or a pharmaceutically acceptable salt thereof.

Definitions

The term "patient" includes mammals such as mice, rats, cows, sheep, pigs, rabbits, goats, horses, monkeys, dogs, cats, and humans.

The term "halo" or "halogen" refers to any radical of fluorine, chlorine, bromine or iodine.

The term "alkyl" refers to a saturated hydrocarbon chain that may be a straight chain or branched chain, containing the indicated number of carbon atoms. For example, $C_{1-6}$alkyl indicates that the group may have from 1 to 6 (inclusive) carbon atoms in it. Any atom can be optionally substituted, e.g., by one or more substitutents. Examples of alkyl groups include without limitation methyl, ethyl, n-propyl, isopropyl, n-butyl, sec-butyl and tert-butyl.

The term "haloalkyl" refers to an alkyl group, in which at least one hydrogen atom is replaced by halo. In some embodiments, more than one hydrogen atom (e.g., 2, 3, 4, 5, 6, 7, 8, 9, 10, 11, 12, 13, or 14) are replaced by halo. In these embodiments, the hydrogen atoms can each be replaced by the same halogen (e.g., fluoro) or the hydrogen atoms can be replaced by a combination of different halogens (e.g., fluoro and chloro). "Haloalkyl" also includes alkyl moieties in which all hydrogens have been replaced by halo (sometimes referred to herein as perhaloalkyl, e.g., perfluoroalkyl, such as trifluoromethyl). Any atom can be optionally substituted, e.g., by one or more substituents.

As referred to herein, the term "alkoxy" refers to a group of formula —O(alkyl). Alkoxy can be, for example, methoxy, ethoxy, propoxy, isopropoxy, butoxy, iso-butoxy, sec-butoxy, pentoxy, 2-pentoxy, 3-pentoxy, or hexyloxy. Likewise, the term "thioalkoxy" refers to a group of formula —S(alkyl). The terms "haloalkoxy" and "halothioalkoxy" refer to —O(haloalkyl) and —S(haloalkyl), respectively. The term "sulfhydryl" refers to —SH.

The term "aralkyl" refers to an alkyl moiety in which an alkyl hydrogen atom is replaced by an aryl group. One of the carbons of the alkyl moiety serves as the point of attachment of the aralkyl group to another moiety. Any ring or chain atom can be optionally substituted e.g., by one or more substituents. Non-limiting examples of "aralkyl" include benzyl, 2-phenylethyl, and 3-phenylpropyl groups.

The term "alkenyl" refers to a straight or branched hydrocarbon chain containing the indicated number of carbon atoms and having one or more carbon-carbon double bonds. Any atom can be optionally substituted, e.g., by one or more substituents. Alkenyl groups can include, e.g., vinyl, allyl, 1-butenyl, and 2-hexenyl.

The term "heterocycle" or "heterocyclic", as used herein except where noted, represents a stable 4-, 5-, 6- or 7-membered monocyclic- or stable 6-, 7-, 8-, 9-, 10-, 11-, or 12-membered fused bicyclic heterocyclic ring system which comprises at least one non-aromatic (i.e. saturated or partially unsaturated) ring which consists of carbon atoms and from one to four heteroatoms selected from the group consisting of N, O and S, wherein the nitrogen and sulfur heteroatoms may optionally be oxidized, and wherein the nitrogen heteroatom may optionally be quaternized. In the case of a "heterocycle" which is a bicyclic group, the second ring may also be a non-aromatic ring which consists of carbon atoms and from one to four heteroatoms selected from the group consisting of N, O and S, as defined above, or the second ring may be a benzene ring, or a "cycloalkyl", or a "cycloalkenyl", as defined immediately below. Examples of such heterocyclic groups include, but are not limited to, azetidine, chroman, dihydrofuran, dihydropyran, dioxane, dioxolane, hexahydroazepine, imidazolidine, imidazoline, indoline, isochroman, isoindoline, isothiazoline, isothiazolidine, isoxazoline, isoxazolidine, morpholine, oxazoline, oxazolidine, oxetane, piperazine, piperidine, pyran, pyrazolidine, pyrazoline, pyrrolidine, pyrroline, tetrahydrofuran, tetrahydropyran, thiamorpholine, thiazoline, thiazolidine, thiomorpholine and N-oxides thereof.

The term "cycloalkyl" refers to a fully saturated monocyclic, bicyclic, tricyclic, or other polycyclic hydrocarbon groups. Any atom can be optionally substituted, e.g., by one or more substituents. A ring carbon serves as the point of attachment of a cycloalkyl group to another moiety. Cycloalkyl moieties can include, e.g., cyclopropyl, cyclobutyl, cyclopentyl, cyclohexyl, cycloheptyl, adamantyl, and norbornyl (bicycle[2.2.1]heptyl).

The term "cycloalkenyl" refers to partially unsaturated monocyclic, bicyclic, tricyclic, or other polycyclic hydrocarbon groups. A ring carbon (e.g., saturated or unsaturated) is the point of attachment of the cycloalkenyl substituent. Any atom can be optionally substituted e.g., by one or more substituents. Cycloalkenyl moieties can include, e.g., cyclopentenyl, cyclohexenyl, cyclohexadienyl, or norbornenyl.

The term "cycloalkylene", as used herein, refers to a divalent monocyclic cycloalkyl group having the indicated number of ring atoms.

The term "heterocycloalkylene", as used herein, refers to a divalent monocyclic heterocyclyl group having the indicated number of ring atoms.

The term "aryl" as used herein, is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, or biphenyl.

The term "heteroaryl", as used herein except where noted, represents a stable 5, 6 or 7-membered monocyclic- or stable 9 or 10-membered fused bicyclic ring system which comprises at least one aromatic ring,—which consists of carbon atoms and from one to three heteroatoms selected from the group consisting of N, O and S wherein the nitrogen and sulfur heteroatoms may optionally be oxidized, and the nitrogen heteroatom may optionally be quaternized. In the case of a "heteroaryl" which is a bicyclic group, the second ring need not be aromatic and need not comprise a heteroatom. Accordingly, "heteroaryl" includes, for example, a stable 5, 6 or 7-membered monocyclic aromatic ring consisting of carbon atoms and from one to four heteroatoms, as defined immediately above, fused to a benzene ring, or fused to a "heterocycle", "cycloalkyl", or a "cycloalkenyl", as defined above. Examples of such heteroaryl groups include, but are not limited to, benzimidazole, benzisothiazole, benzisoxazole, benzofuran, isobenzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

The term "acyl", as used herein, refers to those groups derived from an organic acid by removal of the hydroxy portion of the acid. Accordingly, acyl is meant to include, for example, acetyl, propionyl, butyryl, decanoyl, pivaloyl, benzoyl and the like.

Compound Forms and Salts

The compounds of this invention may contain one or more stereocenters and thus occur as racemates and racemic mixtures, enantiomerically-enriched mixtures, single enantiomers, individual diastereomers and diastereomeric mixtures. The compounds of this invention may also be represented in multiple tautomeric forms, in such instances, the invention expressly includes all tautomeric forms of the compounds described herein, even though only a single tautomeric form may be represented. All such isomeric forms of such compounds are expressly included in the present invention.

The compounds of this invention include the compounds themselves, as well as their salts and their prodrugs, if applicable. A salt, for example, can be formed between an anion and a positively charged substituent (e.g., ammonium) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids.

When the compound of the present invention is acidic, salts may be prepared from pharmaceutically acceptable non-toxic bases, including inorganic and organic bases. Such salts that may be prepared include a lithium salt, sodium salt, potassium salt, magnesium salt, calcium salt, dicyclohexylamine salt, N-methyl-D-glucamine salt, tris (hydroxymethyl)methylamine salt, arginine salt, lysine salt, and the like.

Lists of suitable salts are found in Remington's Pharmaceutical Sciences, 17th ed., Mack Publishing Company, Easton, Pa., 1985, p. 1418; Journal of Pharmaceutical Science, 66, 2 (1977); and "Pharmaceutical Salts: Properties, Selection, and Use A Handbook; Wermuth, C. G. and Stahl, P. H. (eds.) Verlag Helvetica Chimica Acta, Zurich, 2002 [ISBN 3-906390-26-8] each of which is incorporated herein by reference in their entireties.

The compounds may be radiolabeled with radioactive isotopes, such as for example tritium, iodine-125 or carbon-14. All isotopic variations of the compounds of the invention, whether radioactive or not, are intended to be encompassed within the scope of the invention.

In some embodiments, hydrogen atoms of the compounds described herein may be replaced with deuterium atoms.

In some embodiments, compounds of Formula I are prepared as prodrugs. Prodrugs are generally drug precursors that, following administration to a subject and subsequent absorption, are converted to an active, or a more active species via some process, such as conversion by a metabolic pathway. Examples of prodrugs include $C_{1-6}$ alkyl esters of carboxylic acid groups, which, upon administration to a subject, are capable of providing active compounds.

Pharmaceutical Compositions

The term "pharmaceutically acceptable carrier" refers to a carrier or adjuvant that may be administered to a patient, together with a compound of this invention, or a pharmaceutically acceptable salt thereof, and which does not destroy the pharmacological activity thereof and is nontoxic when administered in doses sufficient to deliver a therapeutic amount of the compound.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention, or a pharmaceutically acceptable salt thereof, and a pharmaceutically acceptable carrier. By "pharmaceutically acceptable" it is meant the carrier, diluent or excipient must be compatible with the other ingredients of the formulation and not deleterious to the recipient thereof.

The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient.

Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The amount administered depends on the compound formulation, route of administration, etc. and is generally empirically determined in routine trials, and variations will necessarily occur depending on the target, the host, and the route of administration, etc. Generally, the quantity of active compound in a unit dose of preparation may be varied or adjusted from about 1, 3, 10 or 30 to about 30, 100, 300 or 1000 mg, according to the particular application. For convenience, the total daily dosage may be divided and administered in portions during the day if desired.

Uses

In one aspect the invention disclosed herein is directed to compounds of Formula I and pharmaceutically acceptable salts thereof, which are useful in the treatment of prostate, breast, ovarian, liver, kidney, colon, pancreatic, human chronic lymphocytic leukemia, melanoma and other cancers. In another aspect the invention is directed to a method of preventing the onset of and/or recurrence of acute and chronic myeloid leukemia, as well as other cancers. The invention also includes pharmaceutical compositions comprising a therapeutically effective amount of compound of Formula I, or a pharmaceutically acceptable salt thereof. The invention disclosed herein is also directed to methods of treating prostate, breast, ovarian, liver, kidney, colon, pancreatic, human chronic lymphocytic leukemia, melanoma and other cancers. The invention disclosed herein is further directed to methods of treating prostate, breast, colon, pancreatic, human chronic lymphocytic leukemia, melanoma and other cancers comprising administration of a therapeutically effective amount of a selective PPARα antagonist. The methods include administering to the subject an effective amount of a compound of Formula (I) (and/or a compound of any of the other formulae described herein) or a salt (e.g., a pharmaceutically acceptable salt) thereof as defined anywhere herein. In another aspect, the use of a compound of Formula (I) (and/or a compound of any of the other formulae described herein) or a salt (e.g., a pharmaceutically acceptable salt) thereof as defined anywhere herein in the preparation of, or for use as, a medicament for the treatment (e.g., controlling, alleviating, or slowing the progression of) or prevention (e.g., delaying the onset of or reducing the risk of developing) of one or more diseases, disorders, or conditions caused by, or associated with, prostate, breast, ovarian, liver, kidney, colon, pancreatic, human chronic lymphocytic leukemia, melanoma and other cancers.

In one aspect the invention is directed a method of treating a cancer which is negatively impacted by diminution in its metabolism via fatty acid oxidation, comprising administration of a therapeutically effective amount of a compound of Formula I (and/or a compound of any of the other formulae described herein) or a salt (e.g., a pharmaceutically acceptable salt). In another aspect, the invention is directed to a method of treating a cancer having a metabolism that is reliant on fatty acid oxidation, comprising administration of a therapeutically effective amount of a compound of Formula I (and/or a compound of any of the other formulae described herein), or a pharmaceutically acceptable salt thereof.

Administration

The compounds and compositions described herein can, for example, be administered orally, parenterally (e.g., subcutaneously, intracutaneously, intravenously, intramuscularly, intraarticularly, intraarterially, intrasynovially, intrasternally, intrathecally, intralesionally and by intracranial injection or infusion techniques), by inhalation spray, topically, rectally, nasally, buccally, vaginally, via an implanted reservoir, by injection, subdermally, intraperitoneally, transmucosally, or in an ophthalmic preparation, with a dosage ranging from about 0.01 mg/kg to about 1000 mg/kg, (e.g., from about 0.01 to about 100 mg/kg, from about 0.1 to about 100 mg/kg, from about 1 to about 100 mg/kg, from about 1 to about 10 mg/kg) every 4 to 120 hours, or according to the requirements of the particular drug. The interrelationship of dosages for animals and humans (based on milligrams per meter squared of body surface) is described by Freireich et al., Cancer Chemother. Rep. 50, 219 (1966). Body surface area may be approximately determined from height and weight of the patient. See, e.g., Scientific Tables, Geigy Pharmaceuticals, Ardsley, N.Y., 537 (1970). In certain embodiments, the compositions are administered by oral administration or by injection. The methods herein include the administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Dosage forms include from about 0.05 milligrams to about 2,000 milligrams (e.g., from about 0.1 milligrams to about 1,000 milligrams, from about 0.1 milligrams to about 500 milligrams, from about 0.1 milligrams to about 250 milligrams, from about 0.1 milligrams to about 100 milligrams, from about 0.1 milligrams to about 50 milligrams, or from about 0.1 milligrams to about 25 milligrams) of a compound of Formula I (and/or a compound of any of the other formulae described herein) or a salt (e.g., a pharmaceutically acceptable salt) thereof as defined anywhere herein. The dosage forms can further include a pharmaceutically acceptable carrier and/or an additional therapeutic agent.

In one aspect the compounds of the invention may be co-administered with one or more additional anti-cancer agents. The additional anti-cancer agents include, but are not limited to alkylating agents such as cyclophosphamide, chlorambucil, mecloreethamine, ifosfamide, or melphalan; antimetabolites such as methotrexate, cytarabine, fludarabine, 6-mercaptopurine, azathioprene, pyrimidines, or 5-fluorouracil; antimitotic agents such as vincristine, paclitaxel, vinorelbine or docetaxaxel; a topoisomerase inhibitors such as doxorubicin or irinotecan; platinum derivatives such as cisplatin, carboplatin or oxaliplatin; hormone therapeutics such as tamoxifen; aromatase inhibitors such as bicalutamide, anastrozole, exemestane or letrozole; signaling inhibitors such as imatinib, gefitinib or erlotinib; monoclonal antibodies such as rituximab, trastuzumab, gemtuzumab or ozogamicin; differentiating agents such as tretinoin or arsenic trioxide; antiangiogenic agents such as bevacizumab, sorafinib or sunitinib; biologic response modifiers such as interferon-alpha; topoisomerase inhibitors such as camptothecins (including irinotecan and topotecan), amsacrine, etoposide, etoposide phosphate, or teniposide; cytotoxic antibiotics such as actinomycin, anthracyclines including doxorubicin, daunorubicin, valrubicin, idarubicin, epirubicin, bleomycin, plicamycin or mitomycin; vinca alkaloids such as vincristine, vinblastine, viorelbine or vindesine; or podophyllotoxins such as etoposide and teniposide; or mTOR inhibitors such as rapamycin, temsirolimus and everolimus.

Other anti-cancer agents for use in combination with the compounds include one or more of the following: abiraterone, adriamycin, dactinomycin, bleomycin, vinblastine, cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; everolimus; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; iimofosine; interleukin II (including recombinant interleukin II, or rIL2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; metformin, methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; rapamycin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; temsirolimus; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

In certain embodiments, the additional agents may be administered separately, as part of a multiple dose regimen, from the compounds of this invention (e.g., sequentially, or on different overlapping schedules with the administration of one or more compounds of Formula (I) (and/or a compound of any of the other formulae including any subgenera or specific compounds thereof)). In other embodiments, these agents may be part of a single dosage form, mixed together with the compounds of this invention in a single composition. In still another embodiment, these agents can be given as a separate dose that is administered at about the same time as one or more compounds of Formula (I) (and/or a compound of any of the other formulae including any subgenera or specific compounds thereof) are administered (e.g., simultaneously with the administration of one or more compounds of Formula (I) (and/or a compound of any of the other formulae including any subgenera or specific compounds thereof)). When the compositions of this invention include a combination of a compound of the formulae described herein and one or more additional therapeutic or prophylactic agents, both the compound and the additional agent can be present at dosage levels of between about 1 to 100%, and more preferably between about 5 to 95% of the dosage normally administered in a monotherapy regimen.

The compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

The compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase that is then combined with emulsifying and/or suspending agents. If desired, certain sweetening and/or flavoring and/or coloring agents may be added.

Biological Function

The utility of the invention can be demonstrated by one or more of the following methods or other methods known in the art:

Human PPARα Reporter Assay

The screening of test compounds for agonist or antagonist activities against human PPARα receptors was performed using a commercial kit, Human PPARα Reporter Assay System (Indigo Biosciences, Cat. # IB00111).

This nuclear receptor assay system utilizes proprietary non-human mammalian cells engineered to provide constitutive, high-level expression of Human PPARα. Because these cells incorporate a PPARα-responsive luciferase reporter gene, quantifying expressed luciferase activity provides a sensitive surrogate measure of PPARα activity in the treated cells. The primary application of this reporter assay system is in the screening of test samples to quantify any functional activity, either agonist or antagonist, that they may exert against human PPARα. While this assay may be used to measure agonism, each of the Examples, infra, exhibits antagonism rather than agonism. Briefly, the reporter cells are dispensed into wells of the assay plate and then immediately dosed with test compounds. Following an overnight incubation, the treatment media are discarded and Luciferase Detection Reagent (LDR) is added. The intensity of light emission from the ensuing luciferase reaction provides a sensitive measure that is directly proportional to the relative level of PPARa activation in the reporter cells.

Target Selectivity Assays

To determine species selectivity, a Mouse PPARα Reporter Assay System was used (Indigo Biosciences, Cat. # M00111). Activity of test compounds to antagonize or agonize other isoforms of human PPAR, for example β/δ and γ, were assessed using the corresponding kits from Indigo Biosciences (Cat. # IB00121 and # IB00101, respectively). In addition to PPAR activity, compounds were also screened for activity against other nuclear hormone receptors including Estrogen Receptor β, Glucocorticoid Receptor and Thyroid Receptor β using commercially available kits (Indigo Biosciences, Cat. # IB00411, IB00201 and IB01101, respectively). Each assay system from Indigo Biosciences uses technology analogous to the human PPARα kit, with the variance being that the cells used for each assay were engineered to over-express the receptor of interest. In addition, the appropriate receptor agonist (included with each kit) was used at ~EC80 for assays in which antagonist potency was being assessed.

Target Selectivity—Counterscreen Assay Results

| Example | PPAR alpha IC$_{50}$ (nM) | PPAR beta/delta IC$_{50}$ (nM) | PPAR gamma IC$_{50}$ (nM) | Thyroid Receptor β IC$_{50}$ (nM) | Glucocorticoid Receptor IC$_{50}$ (nM) | Estrogen Receptor β IC$_{50}$ (nM) |
|---|---|---|---|---|---|---|
| 6 | 58 | 13265 | 39845 | 30849 | 18191 | 19444 |

Measuring Fatty Acid Oxidation Using $^3$H Palmitate

Fatty acid oxidation is measured using $^3$H palmitate metabolism into $^3$H$_2$O as described previously (Nieman et al., 2011). Briefly, cells (e.g. HepG2, PC3 and CLL) are plated in growth media and allowed to adhere overnight. Cells are then treated with compound or 40 µM etomoxir (an inhibitor of fatty acid oxidation) as control. After treatment, cells are washed with DPBS followed by incubation in assay buffer (growth media, $^3$H palmitate and compound). After incubation, media is collected and proteins precipitated with 5% tricholoroacetic acid. The precipitate is pelleted by centrifugation and the supernatant collected. Any remaining $^3$H palmitate in the supernatant is then removed by purification over a Dowex anion exchange column. $^3$H$_2$O is then measured by scintillation counting.

Measurement of Cell Viability

Purified CLL cells were cultured at 2×10$^5$ cells/200 µL of RPMI1640 supplemented with 10% FCS in 96-well plates under various treatment conditions. Determination of CLL cell viability was based on the analysis of mitochondrial transmembrane potential (ΔΨm) using 3,3'-dihexyloxacarbocyanine iodide (DiOC6) (Invitrogen) and cell membrane permeability to propidium iodide (PI) (Sigma). For viability assays, 100 µL of the cell culture was collected at the indicated time points and transferred to polypropylene tubes containing 100 µL of 40 µM DiOC6 and 10 µg/mL PI in culture media. The cells were then incubated at 37° C. for 15 min and analyzed within 30 min by flow cytometry using an Accuri C6 flow cytometer. The percentage of viable cells was determined by gating on PI negative and DiOC6 bright cells.

In Vivo PD Model: PPAR Alpha Agonist-Induced Changes in Liver Gene Expression

CD-1 mice were treated with test compound 1-2 hours prior to oral gavage with the PPAR alpha agonist WY14,643 (3 mg/kg). For the 1 day pharmacodynamic model, animals were euthanized 6 hours after agonist treatment. For the 3 day pharmacodynamic model, mice were dosed again with antagonist and WY14,643 on day 2 and day 3. In this case, mice were euthanized 6 hours following WY14,643 on day 3. Upon termination, blood was collected for DMPK analysis. Liver was collected, placed into Trizol and stored at −80° C. until processing. RNA was extracted from thawed and homogenized tissue using standard Trizol RNA isolation methods. RT-PCR was performed on the extracted RNA using primers specific for PPAR alpha regulated genes. Quantitative PCR was performed on the resulting cDNA and expression was normalized to β-actin.

In Vivo Cancer Model: B16F10 Model of Pulmonary Metastasis

B16F10 cells were cultured in standard growth media, harvested when approximately 50% confluent and injected into C57BL/6 mice via the tail vein (50,000 cells per mouse in 200 µL). Mice were treated daily with test compound. On day 21, mice were euthanized. Lungs were harvested and placed into Fekete's solution overnight to facilitate visualization of the tumors. Black nodules were enumerated.

FIG. 1 shows inhibition of metastasis of B16F10 melanoma cells to the lung following oral doses of Example 6 at 0.3, 3 and 30 mg/kg. Statistics were performed by ANOVA with Dunnett's Multiple Comparison Test post-hoc to determine statistical differences from vehicle treatment group. * denotes P<0.05, while *** denotes P<0.001.

Synthesis

The starting materials used for the synthesis are either synthesized or obtained from commercial sources, such as, but not limited to, Sigma-Aldrich, Fluka, Acros Organics, Alfa Aesar, VWR Scientific, and the like. General methods for the preparation of compounds can be modified by the use of appropriate reagents and conditions for the introduction of the various moieties found in the structures are provided herein.

In some embodiments, compounds described herein are prepared as outlined in the following general synthetic scheme.

General Synthetic Scheme for Exemplary Compounds

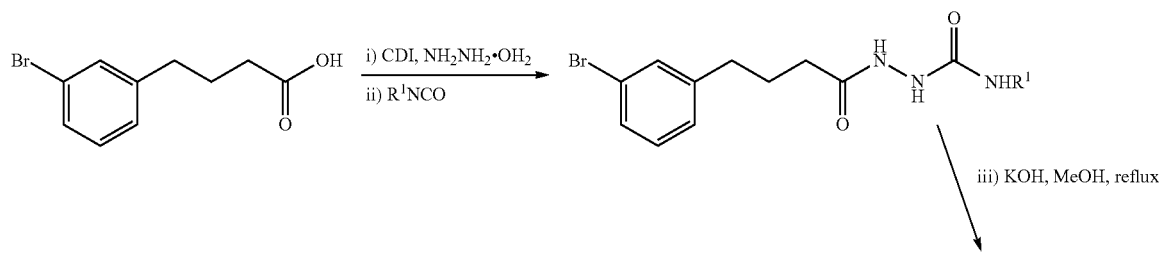

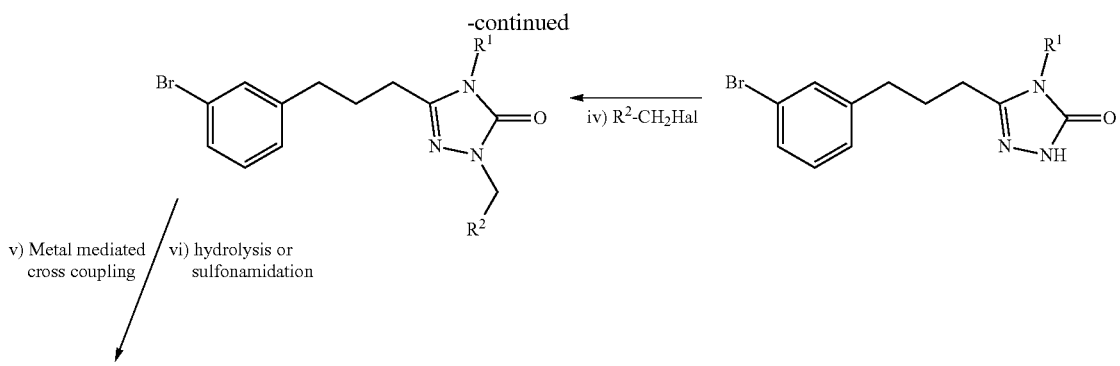
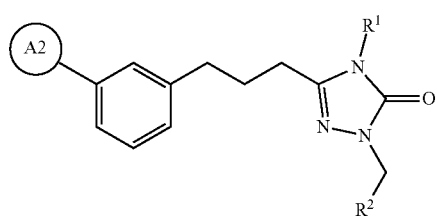
For Heterocycle containing central rings:
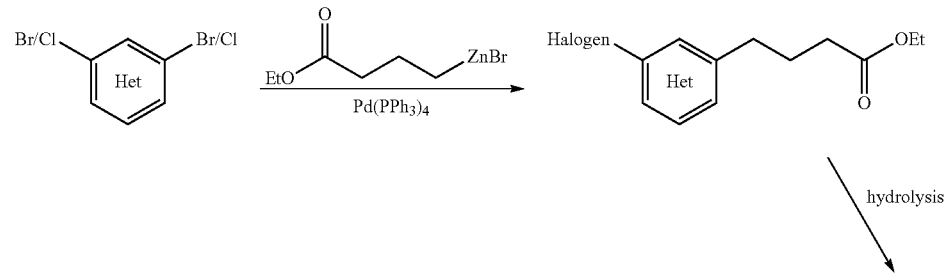
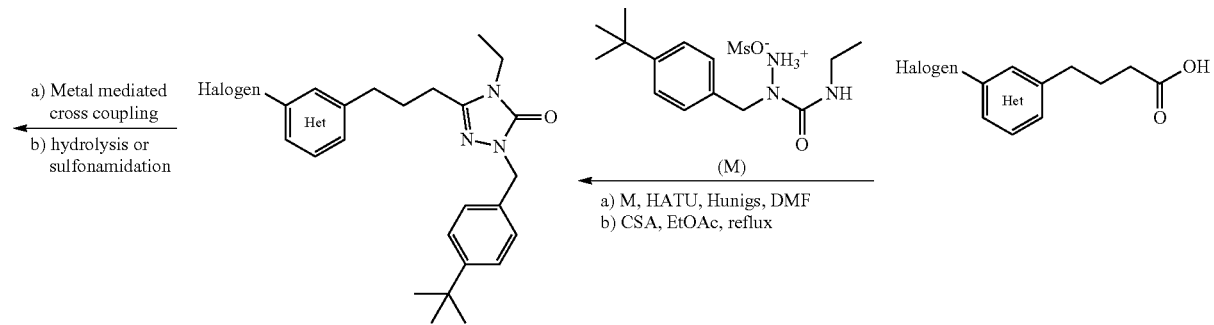

Preparation of Intermediates

4-(3-Bromophenyl)butanoic acid

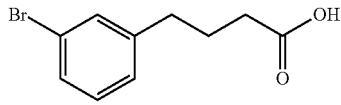 [SMILES: O=C(O)CCCc1cccc(Br)c1]

Step 1: To a solution of 3-bromobenzaldehyde (5.00 g, 27.0 mmol) in DMF (18 mL) was added sodium cyanide (331 mg, 6.8 mmol) and the resulting solution was heated at 45° C. for 30 min. A solution of acrylonitrile (1.55 mL, 23.7 mmol) in DMF (2 mL) was added dropwise over a period of 20 minutes and the heating continued for 3 hrs. The solution was allowed to cool after which AcOH (1 mL) was added, the reaction mixture partitioned between EtOAc and water, the organic phase extracted, dried (MgSO$_4$), filtered and evaporated in vacuo. The residue was purified using silica gel chromatography (0 to 30% EtOAc in hexanes) to afford 3.1 g of 4-(3-bromophenyl)-4-oxobutanenitrile as a yellow oil.

Step 2: To a solution of the isolated nitrile (3.1 g, 13.0 mmol) in ethylene glycol (22 mL) was added water (0.5 mL), hydrazine monohydrate (1.5 mL) and potassium hydroxide (3.34 g). The reaction mixture was heated to 195° C. until analysis by LCMS indicated complete reaction, after which it was allowed to cool to room temperature, diluted with water and acidifed to pH ~2 with 2N HCl. The resulting solution was extracted with EtOAc, dried (MgSO$_4$), filtered and evaporated in vacuo. Purification of the residue on silica gel (0 to 30% acetone in hexanes) afforded 2.9 g of the title acid. 4-(3-Bromophenyl)butanehydrazide:

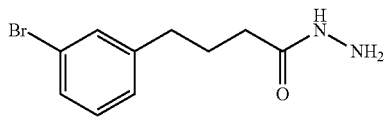 [SMILES: NNC(=O)CCCc1cccc(Br)c1]

To a solution of 4-(3-bromophenyl)butanoic acid (2.9 g, 11.9 mmol) in THF (50 mL) was added carbonyldiimidazole (2.32 g, 14.3 mmol) and stirred for 1.5 hrs. Hydrazine monohydrate (2.4 mL, ~4 eq.) was added and the reaction was complete after 30 minutes as judged by LCMS analysis. The solution was partitioned between EtOAc and water, the organic phase extracted, dried (MgSO$_4$), filtered and evaporated to afford the title compound which was then used without further purification.

3-(3-(3-Bromophenyl)propyl)-4-ethyl-1H-1,2,4-triazol-5(4H)-one

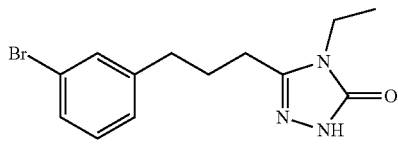 [SMILES: CCn1c(CCCc2cccc(Br)c2)n[nH]c1=O]

Step 1: The previously isolated 4-(3-bromophenyl)butanehydrazide (11.9 mmol) was dissolved in THF (50 mL) to which was added ethyl isocyanate (1.13 mL, 14.3 mmol). After stirring at room temperature for 12 hrs, the solution was evaporated to dryness to afford 2-(4-(3-bromophenyl)butanoyl)-N-ethylhydrazinecarboxamide which was then used without further purification.

Step 2: To a solution of the isolated carboxamide in MeOH (50 mL) was added KOH (6 g) and the reaction mixture was heated to reflux for 16 hrs. After complete reaction as judged by LCMS analysis, the solvent was removed and the residue diluted in DCM and acidified with 1N HCl with cooling. Extraction of the resulting mixture with DCM, drying of the organic phase (MgSO$_4$), filtration and evaporation of the filtrate in vacuo afforded crude 3-(3-(3-bromophenyl)propyl)-4-ethyl-1H-1,2,4-triazol-5 (4H)-one which could be purified on silica gel (0 to 100% EtOAc in hexanes).

3-(3-(3-Bromophenyl)propyl)-1-(4-(tert-butyl)benzyl)-4-ethyl-1H-1,2,4-triazol-5(4H)-one

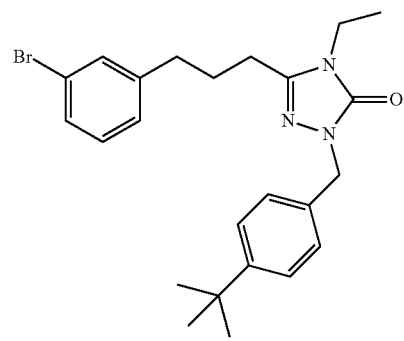 [SMILES: CCn1c(CCCc2cccc(Br)c2)nn(Cc2ccc(C(C)(C)C)cc2)c1=O]

To a solution of 3-(3-(3-bromophenyl)propyl)-4-ethyl-1H-1,2,4-triazol-5(4H)-one (27.7 g, 89.3 mmol) in DMF (200 mL) was added potassium carbonate (40.0 g, 288.7 mmol) followed by 4-tert-butylbenzylbromide (17.2 mL, 93.8 mmol) and the resulting suspension was stirred vigorously for 48 hrs at room temperature. The reaction mixture was diluted with EtOAc, washed with water (×2), dried (MgSO$_4$), filtered and evaporated in vacuo. Purification of the residue on silica gel (0 to 50% EtOAc in hexanes) afforded the title compound as a colorless oil.

1-(4-(tert-Butyl)benzyl)-4-ethyl-3-(3-(3-(4,4,5,5-tetramethyl-1,3,2-dioxaborolan-2-yl)phenyl)propyl)-1H-1,2,4-triazol-5(4H)-one

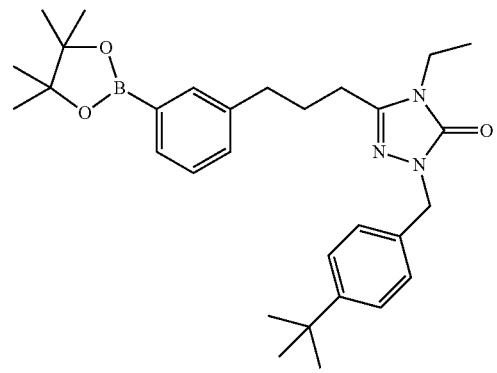 [SMILES: CCn1c(CCCc2cccc(B3OC(C)(C)C(C)(C)O3)c2)nn(Cc2ccc(C(C)(C)C)cc2)c1=O]

To a solution of 3-(3-(3-bromophenyl)propyl)-1-(4-(tert-butyl)benzyl)-4-ethyl-1H-1,2,4-triazol-5(4H)-one (11.7 g, 25.5 mmol) in dioxane (150 mL) was added potassium acetate (7.5 g, 76.5 mmol), bis(pinacolato)diboron (7.8 g, 30.7 mmol) and Pd(dppf)Cl$_2$ (750 mg). The resulting solution was sparged with dry nitrogen for 15 minutes and then heated to 85° C. for a period of 3 hrs. The solvent was removed in vacuo and the residue partitioned between EtOAc and water. The organic phase was separated, dried (MgSO$_4$), filtered and evaporated to give the crude boronate. This was further purified on silica gel, eluting with 0 to 50% EtOAc in hexanes, to afford the title boronate as a colorless oil.

Methyl 2-(5-bromo-2-hydroxyphenyl)acetate

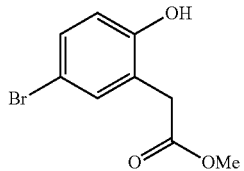 [SMILES: COC(=O)Cc1cc(Br)ccc1O]

To a solution of 2-(2-hydroxyphenyl)acetic acid (15.6 g, 103 mmol) in MeOH (350 mL) was added tetrabutylammonium tribromide (50 g, 103 mmol) in small portions over a 10 minute period. After stirring at ambient temperature for 24 hrs, the solvent was evaporated and the residue taken up in EtOAc, washed with 1N HCl, extracted with EtOAc, the organic phases dried (MgSO$_4$), filtered and evaporated. The residue was purified on silica gel eluting with a gradient of 30% EtOAc in hexanes to afford the title compound as a colorless solid.

Methyl 2-(5-bromo-2-ethoxyphenyl)acetate

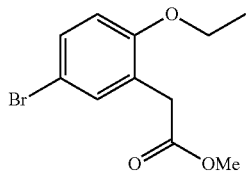

To a solution of methyl 2-(5-bromo-2-hydroxyphenyl)acetate (1.0 g, 4.1 mmol) in DMF (8 mL) was added cesium carbonate (2.66 g, 8.2 mmol) and iodoethane (392 µL, 4.9 mmol) and stirred at rt for 2 hrs. After completion, the reaction mixture was partitioned between EtOAc and water, the organic phase separated, washed with water, dried (MgSO$_4$), filtered and evaporated in vacuo. The residue was purified on silica gel eluting with a gradient of 0 to 10% EtOAc in hexanes to afford the title compound as a colorless oil.

Methyl 2-(5-bromo-2-methoxyphenyl)acetate

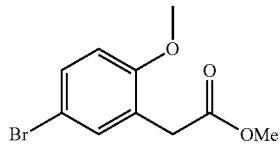

Prepared in an analogous fashion to the aforementioned ethyl derivative using methyl iodide as electrophile.

Methyl 2-(5-bromo-2-propoxyphenyl)acetate

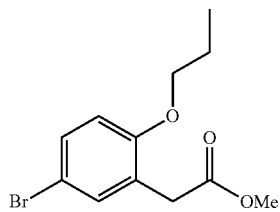 [SMILES: CCCOc1ccc(Br)cc1CC(=O)OC]

Prepared in an analogous fashion to the aforementioned ethyl derivative using 1-bromopropane as electrophile.

Methyl 2-(2-(benzyloxy)-5-bromophenyl)acetate

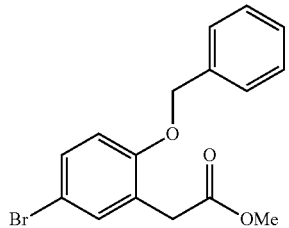 [SMILES: COC(=O)Cc1cc(Br)ccc1OCc1ccccc1]

Prepared in an analogous fashion to the aforementioned ethyl derivative using benzylbromide as electrophile.

Methyl 2-(5-bromo-2-(cyclopropylmethoxy)phenyl)acetate

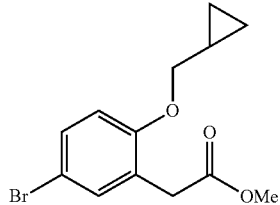 [SMILES: COC(=O)Cc1cc(Br)ccc1OCC1CC1]

Prepared in an analogous fashion to the aforementioned ethyl derivative using (bromomethyl)cyclopropane as electrophile.

Methyl 2-(5-bromo-2-(2-(dimethylamino)ethoxy)phenyl)acetate

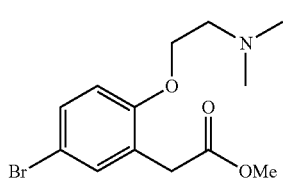

Prepared in an analogous fashion to the aforementioned ethyl derivative using 2-chloro-N,N-dimethylamine hydrochloride as electrophile in the presence of catalytic amount of tetrabutylammonium iodide. Purified on silica using a 0 to 60% gradient of acetone in hexanes.

Methyl 5-bromo-2-propoxybenzoate

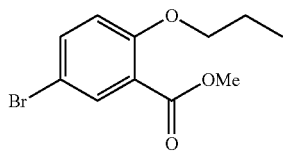

Prepared in an analogous fashion to methyl 2-(5-bromo-2-ethoxyphenyl)acetate but starting with 5-bromo-methyl-salicylate as starting material.

2-(4-Bromo-2-methoxyphenyl)acetonitrile

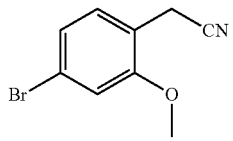

Step 1: To a solution of 5-bromo-2-methylphenol (1.5 g, 8.0 mmol) in DMF (10 mL) was added Cs$_2$CO$_3$ (3.9 g, 12.0 mmol) followed by iodomethane (0.55 mL, 8.8 mmol). The resulting suspension was stirred vigorously for 24 hrs after which it was diluted with EtOAc and washed with water. The organic phase was dried (MgSO$_4$), filtered, evaporated in vacuo and the residue purified on silica gel (0 to 5% EtOAc gradient in hexanes) to afford 4-bromo-2-methoxy-1-methylbenzene as a colorless oil.

Step 2: To a solution of 4-bromo-2-methoxy-1-methylbenzene (1.2 g, 6.0 mmol) in C$_{1-4}$ (15 mL) was added N-bromosuccinimide (1.17 g, 6.5 mmol) and benzoyl peroxide (50 mg). The resulting mixture was heated under reflux for 6 hrs, allowed to cool, evaporated and the residue purified on silica gel eluting with a gradient of 0 to 10% EtOAc in hexanes. The isolated bromide (440 mg, 1.6 mmol) was then dissolved in DMF (2 mL) and potassium cyanide (204 mg, 3.1 mmol) added. After stirring for 48 hrs at room temperature, the solution was diluted with EtOAc, washed with water, the organic phase separated, dried (MgSO$_4$), filtered and evaporated in vacuo. Purification of the residue on silica gel (0 to 10% EtOAc in hexanes) afforded the title compound.

2-(4-Bromo-2-ethoxyphenyl)acetonitrile

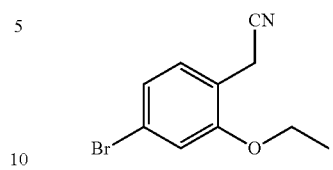

Prepared in an analogous fashion to the methoxy derivative using iodoethane in Step 1.

2-(4-Bromo-2-propoxyphenyl)acetonitrile

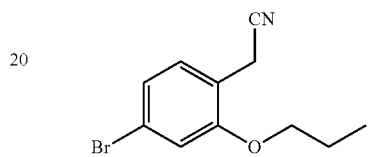

Prepared in an analogous fashion to the methoxy derivative using 1-bromopropane in Step 1.

2-(5-Bromo-2-isopropoxyphenyl) acetonitrile

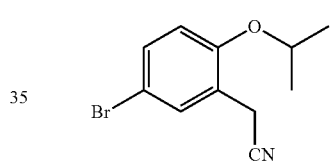

Prepared in an analogous fashion to 2-(4-bromo-2-ethoxyphenyl)acetonitrile utilizing 4-bromo-2-methylphenol as starting material and alkylating the phenol under the following conditions: To a solution of 4-bromo-2-methylphenol (3.5 g, 18.7 mmol) in DMSO (10 mL) was added K$_2$CO$_3$ (5.2 g, 37.5 mmol) and 2-iodopropane (2.25 mL, 22.5 mmol) and the resulting suspension was heated to 60° C. in a sealed vial for 16 hrs. After complete reaction the solution was diluted in EtOAc, washed with water, the organic phase separated, dried (MgSO$_4$), filtered and evaporated in vacuo. The isolated residue was purified on silica gel (0 to 5% EtOAc in hexanes) to afford 4-bromo-1-isopropoxy-2-methylbenzene as a colorless oil.

1-(4-(tert-Butyl)benzyl)-N-ethylhydrazinecarboxamide, monomethanesulfonate (Intermediate M)

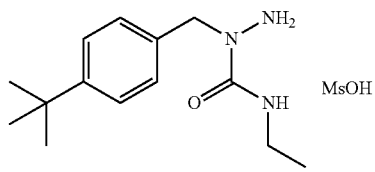 [SMILES: "MsOH" ; CCNC(=O)N(N)Cc1ccc(C(C)(C)C)cc1]

Step 1: In a 500 mL Parr shaker flask was dissolved (E)-tert-butyl 2-(4-(tert-butyl)benzylidene)hydrazinecarboxylate (15.0 g, 54.0 mmol, prepared according to the procedure described in Braden, T. M. et al., *Org. Process Res. Dev.* 2007, 11, 431-440) in iPrOH (75 mL) and EtOAc (25 mL). To this was then added Adam's catalyst (0.7 g, 0.3 mmol) and the resulting suspension was thoroughly deoxygenated via subsurface purging with nitrogen. The reaction vessel was then connected to a Parr shaker and the reaction suspension was shaken under 50 psi of $H_2$ for 3 days (or until no further consumption of hydrogen gas could be discerned). At this point, the excess $H_2$ was discharged from the vessel and the reaction was immediately quenched with DCM. The deactivated catalyst was then removed via filtration through a pad of DCM-wetted celite and the insolubles were washed thoroughly with DCM. The filtrate thus obtained was concentrated in vacuo to furnish a colorless oil. This residue was then transferred as an iPrOH (100 mL) solution to a 500 mL Parr shaker flask and added another batch of Adam's catalyst (0.7 g, 0.3 mmol). After de-oxygenation via subsurface purging with nitrogen, the resulting suspension was shaken under 50 psi of $H_2$ for 2 more days. Finally, excess $H_2$ was discharged from the vessel and the reaction was quenched with DCM. The insolubles were then removed via filtration through a pad of DCM-wetted celite and the celite bed was washed thoroughly with DCM. Concentration of the filtrate thus obtained in vacuo furnished 15.1 g of tert-butyl 2-(4-(tert-butyl)benzyl)hydrazinecarboxylate (quantitative yield).

Step 2: In an oven-dried 1 L RBF equipped with a magnetic stirrer was dissolved tert-butyl 2-(4-(tert-butyl)benzyl)hydrazinecarboxylate (15.1 g, 54.0 mmol) in anhydrous DCM (500 mL). To this was then added neat ethyl isocyanate (6.7 mL, 86 mmol) drop-wise over a period of 15 min and the resulting solution was allowed to stir under nitrogen at RT over 48 h. The volatiles were then removed in vacuo and the resulting residue was co-evaporated with heptanes (3×500 mL) to furnish 19.5 g of tert-butyl 2-(4-(tert-butyl)benzyl)-2-(ethylcarbamoyl)hydrazinecarboxylate (quantitative yield).

Step 3: In an oven-dried 1 L RBF equipped with a magnetic stirrer was dissolved tert-butyl 2-(4-(tert-butyl)benzyl)-2-(ethylcarbamoyl)hydrazinecarboxylate (19.5 g, 54.0 mmol) in anhydrous DCM (500 mL). To this was then added neat MsOH (4.7 mL, 73 mmol) drop-wise over a period of 15 min and the resulting solution was allowed to stir under nitrogen at RT over 16 h. The volatiles were then in vacuo and the resulting residue was co-evaporated with DCM (3×500 mL) and MeOH (3×500 mL) to furnish 19.1 g (99% yield) of intermediate (M) as a pale yellow foam.

Example 1: 2-(3'-(3-(1-(4-(tert-Butyl)benzyl)-4-ethyl-5-oxo-4,5-dihydro-1H-1,2,4-triazol-3-yl)propyl)-[1,1'-biphenyl]-3-yl)acetic Acid Step 1:
To a solution of 3-(3-(3-bromophenyl)propyl)-1-(4-(tert-butyl)benzyl)-4-ethyl-1H-1,2,4-triazol-5(4H)-one (250 mg, 0.55 mmol) in a mixture of DME (5 mL) and water (2 mL) was added potassium carbonate (191 mg, 1.38 mmol) and 3-ethoxycarbonylmethylphenylboronic acid (191 mg, 0.66 mmol). After sparging the mixture with nitrogen, $Pd(PPh_3)_4$ (30 mg, cat.) was added and the reaction heated at 85° C. for 3 hrs. The reaction as allowed to cool, partitioned between EtOAc and water, the organic phase extracted, dried ($MgSO_4$), filtered and evaporated in vacuo. The residue was purified on silica gel eluting with a gradient of 0 to 60% EtOAc in hexanes to afford the ester of the title compound.

Step 2:
To a solution of the aforementioned ester (200 mg, 0.37 mmol) in a mixture of THF (4 mL), MeOH (2 mL) and water (2 mL) was added lithium hydroxide monohydrate (100 mg, 2.4 mmol) and the reaction stirred at room temperature until complete ester hydrolysis was evident as determined by LCMS analysis. Solid citric acid was added to adjust pH to ~4 and the solution partitioned between EtOAc and water. The organic phase was extracted, dried ($MgSO_4$), filtered and evaporated to afford the title acid as a colorless solid.

The following examples (2-4,6-11, 13, 15-19, 28-30, 32 and 33) were prepared in an analogous fashion to Example 1 using the requisite commercially available boronic acid (or pinacol ester) coupling partner and subsequent hydrolysis.

Example 2: 2-(3'-(3-(1-(4-(tert-Butyl)benzyl)-4-ethyl-5-oxo-4,5-dihydro-1H-1,2,4-triazol-3-yl)propyl)-[1,1'-biphenyl]-4-yl)acetic Acid

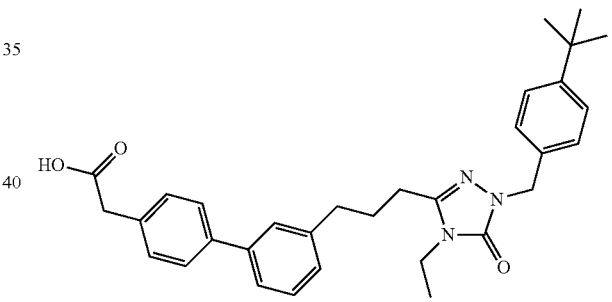

Example 3: 3'-(3-(1-(4-(tert-Butyl)benzyl)-4-ethyl-5-oxo-4,5-dihydro-1H-1,2,4-triazol-3-yl)propyl)-[1,1'-biphenyl]-3-carboxylic Acid

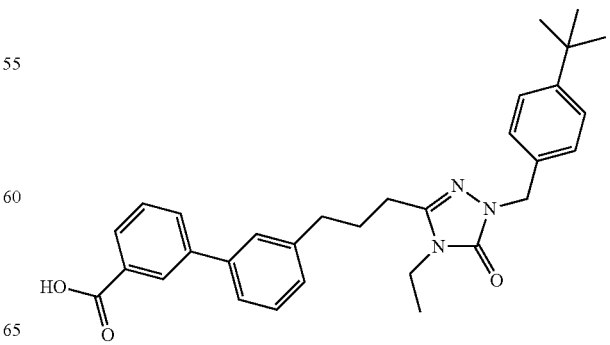

Example 4: 3'-(3-(1-(4-(tert-Butyl)benzyl)-4-ethyl-5-oxo-4,5-dihydro-1H-1,2,4-triazol-3-yl)propyl)-[1,1'-biphenyl]-4-carboxylic Acid

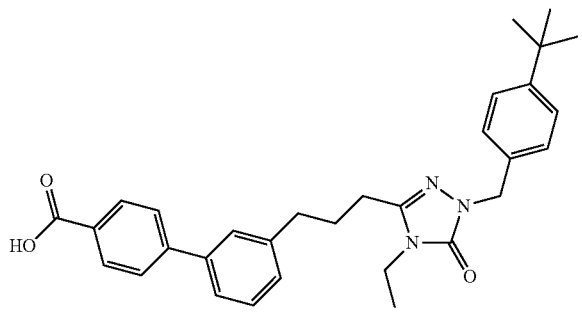 [SMILES: CCn1c(CCCc2cccc(-c3ccc(C(=O)O)cc3)c2)nn(Cc2ccc(C(C)(C)C)cc2)c1=O]

Example 5: 1-(3'-(3-(1-(4-(tert-Butyl)benzyl)-4-ethyl-5-oxo-4,5-dihydro-1H-1,2,4-triazol-3-yl)propyl)-4-ethoxy-[1,1'-biphenyl]-3-yl)cyclopropanecarboxylic Acid

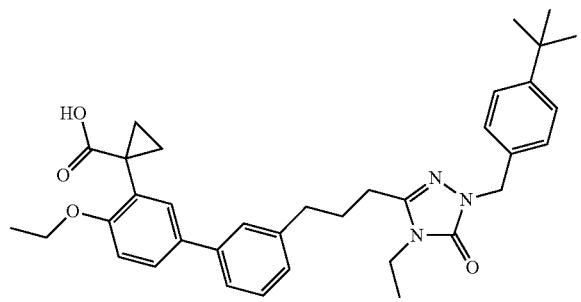 [SMILES: CCOc1ccc(-c2cccc(CCCc3nn(Cc4ccc(C(C)(C)C)cc4)c(=O)n3CC)c2)cc1C1(C(=O)O)CC1]

Preparation of 1-(5-bromo-2-ethoxyphenyl)cyclopropanecarbonitrile

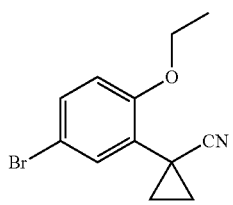

Step 1:

To a solution of 4-bromo-2-methylphenol (5.0 g, 26.7 mmol) in DMF (20 mL) was added $Cs_2CO_3$ (13.0 g, 39.9 mmol) and iodoethane (2.6 mL, 32.5 mmol). The reaction was stirred vigorously for 24 hrs after which the suspension was partitioned between EtOAc and water, the organic phase extracted, wash with water, dried ($MgSO_4$), filtered and evaporated to afford 4-bromo-1-ethoxy-2-methylbenzene used without further purification.

Step 2:

To a solution of 4-bromo-1-ethoxy-2-methylbenzene (5.0 g, 23.1 mmol) in $C_{1-4}$ (80 mL) was added N-bromosuccinimide (4.93 g, 27.6 mmol) and benzoyl peroxide (100 mg, cat.). The reaction mixture was then heated to reflux for a period of 3 hrs after which it was allowed to cool, partially evaporated then filtered to remove the succinimide. The filtrate was then evaporated to dryness to afford the benzylbromide which was used without further purification.

Step 3:

To the crude 4-bromo-2-(bromomethyl)-1-ethoxybenzene (23.1 mmol) isolated previously was added DMF (20 mL) and potassium cyanide (2.26 g, 34.7 mmol) and the slurry stirred at room temperature for 48 hrs. The reaction mixture was partitioned between EtOAc and water, the organic phase separated, dried ($MgSO_4$), filtered and evaporated to afford a mixture of the mono and bis cyanomethyl derivatives. Purification of the mixture using silica gel chromatography (0 to 10% EtOAc in hexanes) afforded 2.5 g of 2-(5-bromo-2-ethoxyphenyl)acetonitrile.

Step 4:

To 2-(5-bromo-2-ethoxyphenyl)acetonitrile (1.0 g, 4.16 mmol) in 2 mL of aqueous KOH (50%) was added tetrabutylammonium bromide (200 mg) and 1,2-dibromoethane (541 µL, 6.2 mmol) and heated in a sealed vial at 50° C. with vigorous stirring for 4 hrs. The mixture was partitioned between EtOAc and 1N HCl, the organic phase separated, dried ($MgSO_4$), filtered and evaporated in vacuo. The afforded 1-(5-bromo-2-ethoxyphenyl)cyclopropanecarbonitrile was used without further purification.

Example 5 was prepared analogously to example 1 using 1-(5-bromo-2-ethoxyphenyl)cyclopropanecarbonitrile as the coupling partner. Furthermore, hydrolysis of the resulting nitrile after cross-coupling was performed using KOH in ethylene glycol and water at 150° C.

Example 6: 2-(3'-(3-(1-(4-(tert-Butyl)benzyl)-4-ethyl-5-oxo-4,5-dihydro-1H-1,2,4-triazol-3-yl)propyl)-4-ethoxy-[1,1'-biphenyl]-3-yl)acetic Acid

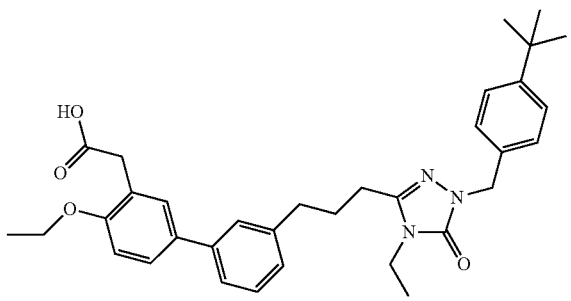 [SMILES: CCOc1ccc(-c2cccc(CCCc3nn(Cc4ccc(C(C)(C)C)cc4)c(=O)n3CC)c2)cc1CC(=O)O]

Example 7: 1-(3'-(3-(1-(4-(tert-Butyl)benzyl)-4-ethyl-5-oxo-4,5-dihydro-1H-1,2,4-triazol-3-yl)propyl)-[1,1'-biphenyl]-3-yl)cyclopropanecarboxylic Acid

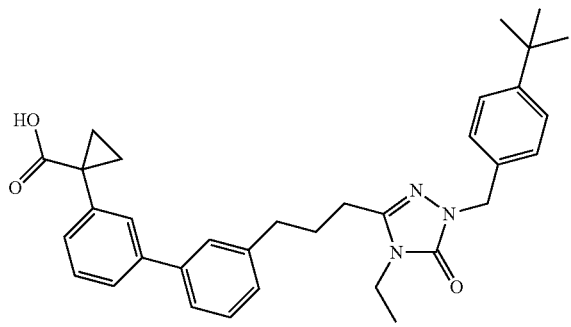 [SMILES: CCn1c(CCCc2cccc(-c3cccc(C4(C(=O)O)CC4)c3)c2)nn(Cc2ccc(C(C)(C)C)cc2)c1=O]

Example 8: 1-(3'-(3-(1-(4-(tert-Butyl)benzyl)-4-ethyl-5-oxo-4,5-dihydro-1H-1,2,4-triazol-3-yl)propyl)-[1,1'-biphenyl]-4-yl)cyclopropanecarboxylic Acid

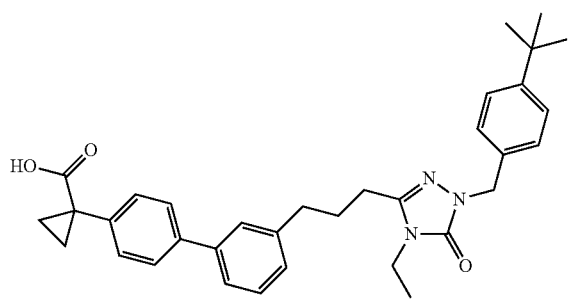 [SMILES: CCn1c(CCCc2cccc(-c3ccc(C4(C(=O)O)CC4)cc3)c2)nn(Cc2ccc(C(C)(C)C)cc2)c1=O]

Example 9: 3'-(3-(1-(4-(tert-Butyl)benzyl)-4-ethyl-5-oxo-4,5-dihydro-1H-1,2,4-triazol-3-yl)propyl)-4-methoxy-[1,1'-biphenyl]-3-carboxylic Acid

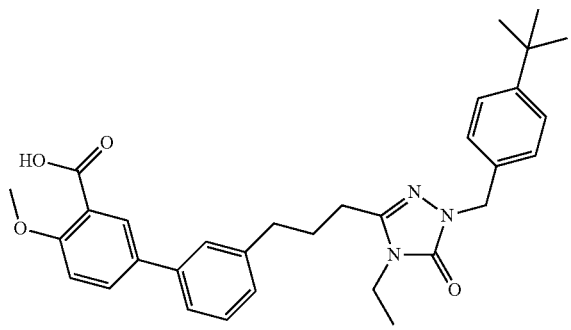 [SMILES: CCn1c(CCCc2cccc(-c3ccc(OC)c(C(=O)O)c3)c2)nn(Cc2ccc(C(C)(C)C)cc2)c1=O]

Example 10: 3'-(3-(1-(4-(tert-Butyl)benzyl)-4-ethyl-5-oxo-4,5-dihydro-1H-1,2,4-triazol-3-yl)propyl)-4-ethoxy-[1,1'-biphenyl]-3-carboxylic Acid

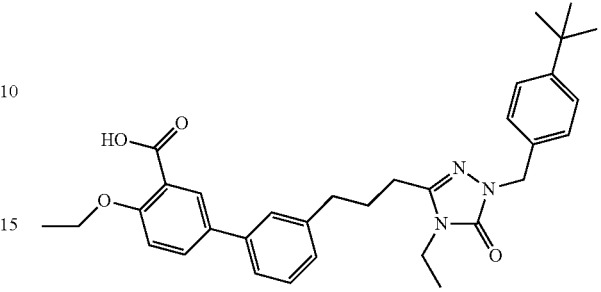

Example 11: 2-(3'-(3-(1-(4-(tert-Butyl)benzyl)-4-ethyl-5-oxo-4,5-dihydro-1H-1,2,4-triazol-3-yl)propyl)-4-propoxy-[1,1'-biphenyl]-3-yl)acetic Acid

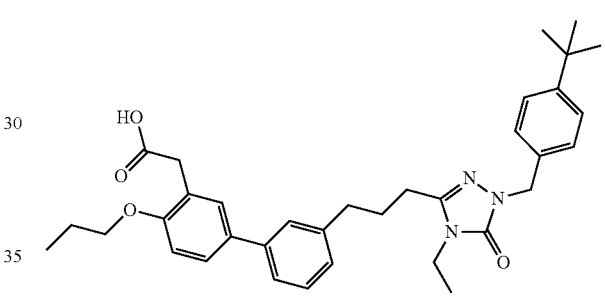

Example 12: N-(6-(3-(3-(1-(4-(tert-Butyl)benzyl)-4-ethyl-5-oxo-4,5-dihydro-1H-1,2,4-triazol-3-yl)propyl)phenyl)pyridin-3-yl)benzenesulfonamide

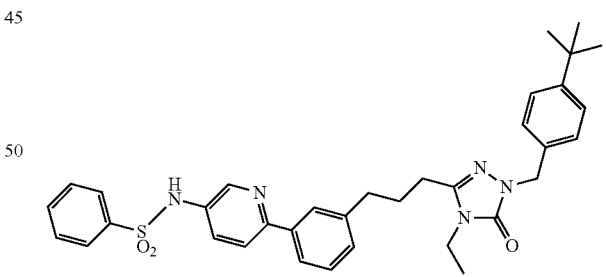

Step 1:

To a solution of 3-(3-(3-bromophenyl)propyl)-1-(4-(tert-butyl)benzyl)-4-ethyl-1H-1,2,4-triazol-5(4H)-one (300 mg, 0.6 mmol) in a mixture of DME (5.5 mL) and water (2.5 mL) was added potassium carbonate (250 mg, 1.80 mmol) and 3-amino-6-bromopyridine (135 mg, 0.78 mmol). After sparging the mixture with nitrogen, Pd(PPh$_3$)$_4$ (30 mg, cat.) was added and the reaction heated at 85° C. for 6 hrs. The reaction was allowed to cool, partitioned between EtOAc and water, the organic phase extracted, dried (MgSO$_4$), filtered and evaporated in vacuo. The residue was purified on silica gel eluting with a gradient of 0 to 60% EtOAc in hexanes to afford 3-(3-(3-(5-aminopyridin-2-yl)phenyl)propyl)-1-(4-(tert-butyl)benzyl)-4-ethyl-1H-1,2,4-triazol-5(4H)-one.

Step 2:

To a solution of the isolated 3-(3-(3-(5-aminopyridin-2-yl)phenyl)propyl)-1-(4-(tert-butyl)benzyl)-4-ethyl-1H-1,2,4-triazol-5(4H)-one (50 mg, 0.106 mmol) in pyridine (0.8 mL) was added benzenesulfonyl chloride (14 μL, 0.106 mmol). After stirring for 48 hrs, the reaction mixture was diluted with EtOAc, washed with water, dried (MgSO₄), filtered and evaporated in vacuo. The isolated residue was purified on silica gel eluting with a gradient of 0 to 5% MeOH in CHCl₃ to afford the title compound.

Example 13: 2-(3'-(3-(1-(4-(tert-Butyl)benzyl)-4-ethyl-5-oxo-4,5-dihydro-1H-1,2,4-triazol-3-yl)propyl)-4-methoxy-[1,1'-biphenyl]-3-yl)acetic Acid

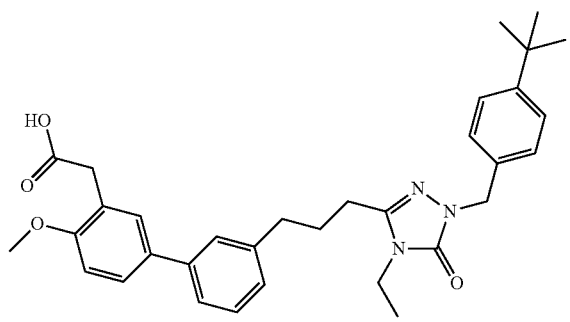 [SMILES: CCn1c(CCCc2cccc(-c3ccc(OC)c(CC(=O)O)c3)c2)nn(Cc2ccc(C(C)(C)C)cc2)c1=O]

Example 14: 1-(3'-(3-(1-(4-(tert-Butyl)benzyl)-4-ethyl-5-oxo-4,5-dihydro-1H-1,2,4-triazol-3-yl)propyl)-4-methyl-[1,1'-biphenyl]-3-yl)cyclopropanecarboxylic Acid

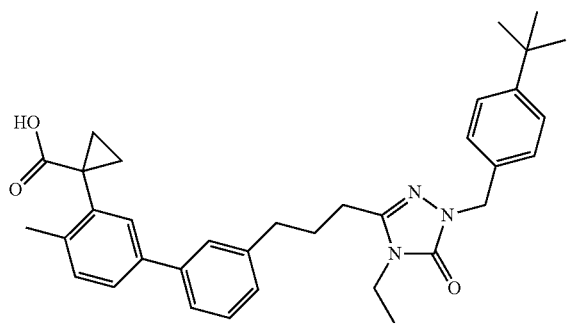 [SMILES: CCn1c(CCCc2cccc(-c3ccc(C)c(C4(C(=O)O)CC4)c3)c2)nn(Cc2ccc(C(C)(C)C)cc2)c1=O]

Preparation of 1-(5-bromo-2-methylphenyl)cyclopropanecarbonitrile

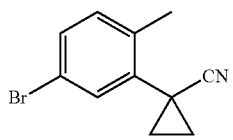

Step 1:

To a suspension of LiAlH₄ (0.75 g, 3.11 mmol) in diethyl ether (8 mL) at 0° C. was added a solution of methyl 5-bromo-2-methylbenzoate (949 mg, 4.14 mmol) in diethyl ether (2 mL) dropwise. The reaction mixture was allowed to slowly warm to rt, then quenched with EtOAc, partitioned between EtOAc and 2N HCl and extracted (EtOAc). The organic phase was washed with water, dried (MgSO₄), filtered and evaporated in vacuo to afford the crude alcohol which can be used without further purification.

Step 2:

To the aforementioned alcohol (818 mg, 4.1 mmol) in diethyl ether (10 mL) cooled to 0° C. was added PBr₃ (0.2 mL, 2.07 mmol) and stirred at 0° C. for 1 hr. The reaction was then quenched with water, diluted with ether, washed with sodium bicarbonate solution, the organic phase separated and dried (MgSO₄), filtered and evaporated yielding 726 mg of the benzyl bromide.

Step 3:

To 4-bromo-2-(bromomethyl)-1-methylbenzene (726 mg, 2.75 mmol) in DMF (8 mL) was added sodium cyanide (142 mg, 2.89 mmol) and the resulting suspension heated to 50° C. for 4 hrs. The reaction mixture was diluted with EtOAc, washed with water then brine, dried (MgSO₄), filtered and evaporated in vacuo. The isolated residue was purified on silica gel eluting with a gradient of 0 to 50% EtOAc in hexanes to afford 2-(5-bromo-2-methylphenyl)acetonitrile.

Step 4:

1-(5-bromo-2-methylphenyl)cyclopropanecarbonitrile was then prepared analogously to the method described in Example 5, Step 4.

Example 14 was completed under the same conditions as described for Example 5.

Example 15: 2-(4-(Benzyloxy)-3'-(3-(1-(4-(tert-butyl)benzyl)-4-ethyl-5-oxo-4,5-dihydro-1H-1,2,4-triazol-3-yl)propyl)-[1,1'-biphenyl]-3-yl)acetic Acid

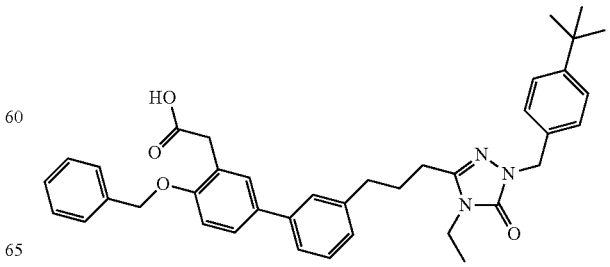

Example 16: 2-(3'-(3-(1-(4-(tert-Butyl)benzyl)-4-ethyl-5-oxo-4,5-dihydro-1H-1,2,4-triazol-3-yl)propyl)-4-(cyclopropylmethoxy)-[1,1'-biphenyl]-3-yl)acetic Acid

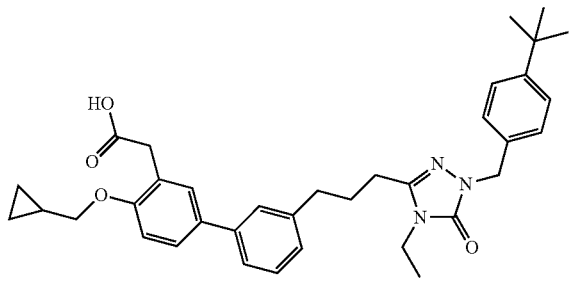 [SMILES: CCn1c(CCCc2cccc(-c3ccc(OCC4CC4)c(CC(=O)O)c3)c2)nn(Cc2ccc(C(C)(C)C)cc2)c1=O]

Example 17: 2-(3'-(3-(1-(4-(tert-Butyl)benzyl)-4-ethyl-5-oxo-4,5-dihydro-1H-1,2,4-triazol-3-yl)propyl)-4-fluoro-[1,1'-biphenyl]-3-v 1)acetic Acid

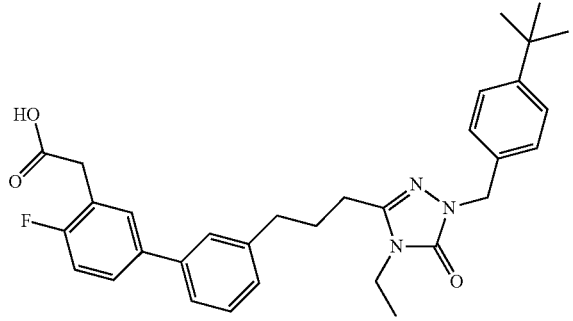 [SMILES: CCn1c(CCCc2cccc(-c3ccc(F)c(CC(=O)O)c3)c2)nn(Cc2ccc(C(C)(C)C)cc2)c1=O]

Example 18: 2-(3'-(3-(1-(4-(tert-Butyl)benzyl)-4-ethyl-5-oxo-4,5-dihydro-1H-1,2,4-triazol-3-yl)propyl)-6-ethoxy-[1,1'-biphenyl]-3-yl)acetic Acid

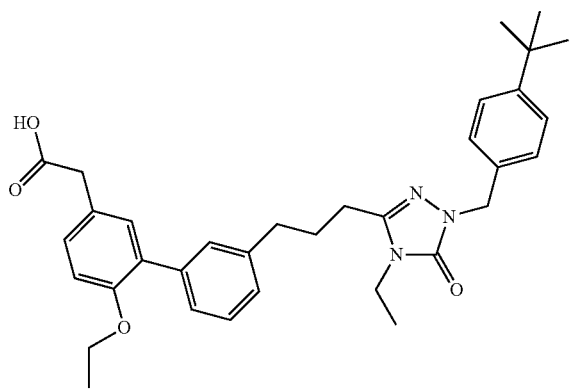 [SMILES: CCOc1ccc(CC(=O)O)cc1-c1cccc(CCCc2nn(Cc3ccc(C(C)(C)C)cc3)c(=O)n2CC)c1]

Example 19: 3'(3'-(3-(1-(4-(tert-Butyl)benzyl)-4-ethyl-5-oxo-4,5-dihydro-1H-1,2,4-triazol-3-yl)propyl)-4-propoxy-[1,1'-biphenyl]-3-carboxylic Acid

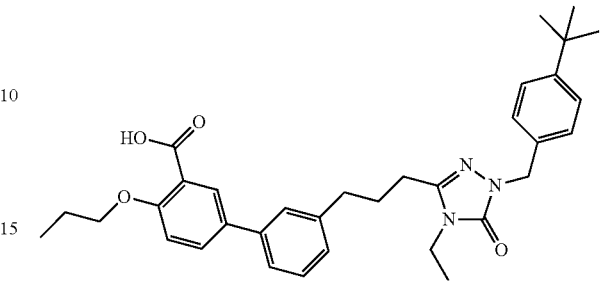

Example 20: N-((3'-(3-(1-(4-(tert-Butyl)benzyl)-4-ethyl-5-oxo-4,5-dihydro-1H-1,2,4-triazol-3-yl)propyl)-[1,1'-biphenyl]-3-yl)methyl)benzenesulfonamide

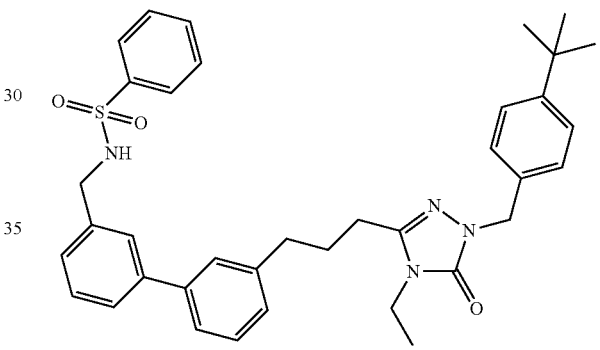

Step 1:

A mixture of 1-(4-(tert-butyl)benzyl)-4-ethyl-3-(3-(3-(4,4,5,5-tetramethyl-1,3,2-dioxaborolan-2-yl)phenyl)propyl)-1H-1,2,4-triazol-5(4H)-one (223 mg, 0.443 mmol), 3-bromobenzyl amine (98 mg, 0.532 mmol, 1.2 eq) and potassium carbonate (183 mg, 1.33 mmol, 3 eq) were taken up in DME (2 mL) and water (1 mL) solution. To this tetrakis(triphenylphosphine)palladium(0) (52 mg, 0.0443 mmol, 0.1 eq) was added and the resulting mixture was stirred at 85° C. under an atmosphere of $N_2$ for 24 hr. The reaction mixture was cooled to room temperature and the solvent was removed under vacuum. The crude material was partitioned between water and EtOAc. The aqueous layer was extracted with EtOAc (3×20 mL) and the organic layer was dried over anhydrous $Na_2SO_4$. The solvent was evaporated in vacuum to obtain the crude product. The crude product was purified on flash column chromatography (silica gel, 0-70% EtOAc, 10% Methanol, 2.5% trieythylamine/Hexanes) to afford a white solid (84 mg, 40% yield) LC-MS: 483 (M+H)+.

Step 2:

A mixture of 3-(3-(3'-(aminomethyl)-[1,1'-biphenyl]-3-yl)propyl)-1-(4-(tert-butyl)benzyl)-4-ethyl-1H-1,2,4-triazol-5(4H)-one (35 mg, 0.0726 mmol) and benzene sulfonylchloride (10 µL, 0.0798 mmol, 1.1 eq) was stirred in pyridine (1 mL) at room temperature for 24 hr. The mixture was poured onto dichloromethane (40 mL) and washed with saturated CuSO₄, water, and brine. The combined organic layers were dried over anhydrous Na₂SO₄, filtered and evaporated under vacuum to obtain the crude product. The crude product was purified on reverse phase HPLC to afford a white foam (10 mg, 33%). LC-MS: 623 (M+H)+.

Example 21: 3-(3'-(3-(1-(4-(tert-Butyl)benzyl)-4-ethyl-5-oxo-4,5-dihydro-1H-1,2,4-triazol-3-yl)propyl)-4-methoxy-[1,1'-biphenyl]-3-yl)propanoic Acid

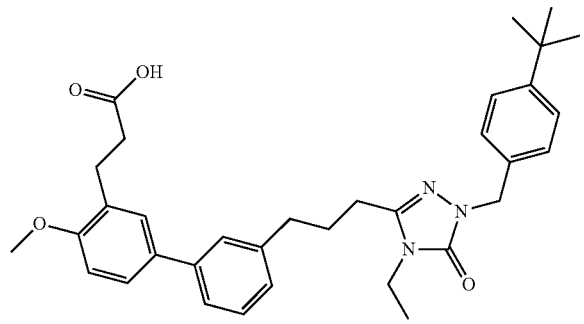 [SMILES: CCn1c(CCCc2cccc(-c3ccc(OC)c(CCC(=O)O)c3)c2)nn(Cc2ccc(C(C)(C)C)cc2)c1=O]

A mixture of 1-(4-(tert-butyl)benzyl)-4-ethyl-3-(3-(3-(4,4,5,5-tetramethyl-1,3,2-dioxaborolan-2-yl)phenyl)propyl)-1H-1,2,4-triazol-5(4H)-one (70 mg, 0.139 mmol), 3-(5-bromo-2-methoxyphenyl) propanoic acid (43 mg, 0.167 mmol, 1.2 eq) and potassium phosphate tribasic (118 mg, 0.556 mmol, 4 eq) were taken up in DME (2 mL) and water (1 mL) solution. To this tris(dibenzylideneacetone)dipalladium(0) (4 mg, 0.0034 mmol, 0.025 eq) and 2-dicyclohexylphosphino-2',6'-dimethoxybiphenyl (5 mg, 0.011 mmol, 0.08 eq) were added and the resulting mixture was stirred at 85° C. under an atmosphere of N₂ for 24 hr. The reaction mixture was cooled to room temperature and the solvent was removed under vacuum. The crude material was partitioned between water and EtOAc. The aqueous layer was extracted with EtOAc (3×20 mL) and the organic layer was dried over anhydrous Na₂SO₄. The solvent was evaporated in vacuum to obtain the crude product. The crude product was purified on reverse phase HPLC to afford a white solid (10 mg, 13% yield) LC-MS: 556 (M+H)+.

Example 22: 2-(3'-(3-(1-(4-(tert-Butyl)benzyl)-4-ethyl-5-oxo-4,5-dihydro-1H-1,2,4-triazol-3-yl)-1,1-difluoropropyl)-4-ethoxy-[1,1'-biphenyl]-3-yl)acetic Acid

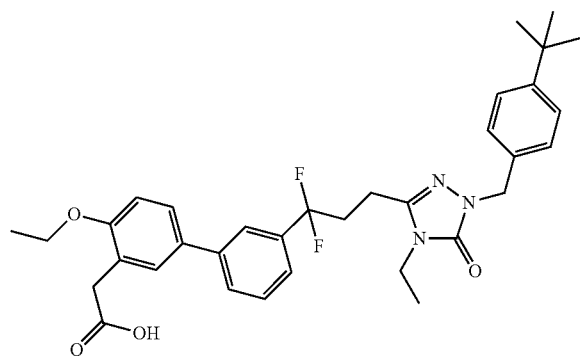 [SMILES: CCOc1ccc(-c2cccc(C(F)(F)CCc3nn(Cc4ccc(C(C)(C)C)cc4)c(=O)n3CC)c2)cc1CC(=O)O]

Step 1:
To a solution of 4-(3-bromophenyl)-4-oxobutanenitrile (1.11 g, 4.66 mmol) in toluene (10 mL) was added Deoxyfluor (8.63 mL, 23.31 mmol, 2.7 M solution in Toluene) followed by EtOH (0.16 mL, 2.80 mmol). The mixture was stirred at 80° C. for 16 hrs. The solution was cooled to rt and diluted with diethyl ether and a solution of saturated aqueous NaHCO₃. The organic layer was separated and washed sequentially with saturated aqueous NaHCO₃, 1M aqueous HCl, and water. The organics were concentrated and residue was purified by column chromatography using 0%-65% gradient EtOAc/Hexanes as eluent to afford 0.570 g (47% yield) of 4-(3-bromophenyl)-4,4-difluorobutanenitrile.

Step 2:
4-(3-Bromophenyl)-4,4-difluorobutanenitrile (0.57 g, 2.19 mmol), ethylene glycol (20 mL), water (2 mL), and KOH (0.701 g, 17.53 mmol) were combined and heated at 80° C. for 16 hrs. The solution was cooled to rt, diluted with EtOAc and quenched with 1M aqueous HCl. The organics were separated and washed sequentially with 0.1M aqueous HCl and brine, filtered through a Na₂SO₄/paper plug and concentrated. The organics were concentrated and residue was purified by column chromatography using 0%-50% gradient acetone/hexanes as eluent to afford 0.386 g (63% yield) of 4-(3-bromophenyl)-4,4-difluorobutanoic acid.

Step 3:
4-(3-Bromophenyl)-4,4-difluorobutanoic acid (0.20 g, 0.717 mmol), Hunig's base (0.33 mL, 1.86 mmol) and 2-(7-aza-1H-benzotriazole-1-yl)-1,1,3,3-tetramethyluronium hexafluorophosphate (0.327 g, 0.86 mmol) were combined in anhydrous DMF (7 mL). The reaction solution was stirred for 40 min at rt, then intermediate (M) (0.248 g, 0.717 mmol) was added. The resulting solution was allowed to stir at rt for 16 h. The reaction mixture was then diluted with EtOAc and 1 N aq. HCl. The organics were separated and washed sequentially with saturated aqueous NaHCO₃, water, and brine. The organic extract was then dried over sodium sulfate and filtered. Concentration of the filtrate afforded crude 2-(4-(3-bromophenyl)-4,4-difluorobutanoyl)-1-(4-(tert-butyl)benzyl)-N-ethylhydrazinecarboxamide, which was used as is in the next step.

Step 4:
To an EtOAc solution (8 mL) of 2-(4-(3-bromophenyl)-4,4-difluorobutanoyl)-1-(4-(tert-butyl)benzyl)-N-ethylhydrazinecarboxamide (0.365 g, 0.717 mmol) was added camphorsulfonic acid (0.18 g, 0.717 mmol) and the resulting solution was heated at reflux for 16 h. The reaction mixture was then diluted with EtOAc and 1 N aq. HCl. The organics were washed sequentially with 1M NaOH and water, and then concentrated. The residue was purified by column chromatography using 10%-90% gradient EtOAc/hexanes as eluent to afford 0.140 g (40% yield, two steps) of 3-(3-(3-bromophenyl)-3,3-difluoropropyl)-1-(4-(tert-butyl)benzyl)-4-ethyl-1H-1,2,4-triazol-5 (4H)-one.

Step 5:
Under a nitrogen atmosphere, 3-(3-(3-bromophenyl)-3,3-difluoropropyl)-1-(4-(tert-butyl)benzyl)-4-ethyl-1H-1,2,4-triazol-5(4H)-one (0.040 g, 0.081 mmol) and methyl 2-(2-ethoxy-5-(4,4,5,5-tetramethyl-1,3,2-dioxaborolan-2-yl)phenyl)acetate (0.029 g, 0.089 mmol) were dissolved in dioxane (3 mL) to which was then added a solution of saturated aqueous NaHCO₃ (1 mL). The resulting solution was then subsurface purged with N₂ for 5 minutes after which, Pd(PPh₃)₄ (0.016 g, 0.014 mmol) was added. The resulting mixture was stirred in a sealed pressure vessel at 90° C. for 16 hrs. The solution was cooled to rt and diluted with EtOAc and water. The organics were washed once more with water and the solution was filtered through a Na$_2$SO$_4$/paper plug and concentrated. The residue was purified by preparatory TLC using 20% acetone/hexanes as eluent to afford 0.029 g of methyl 2-(3'-(3-(1-(4-(tert-butyl)benzyl)-4-ethyl-5-oxo-4,5-dihydro-1H-1,2,4-triazol-3-yl)-1,1-difluoropropyl)-4-ethoxy-[1,1'-biphenyl]-3-yl)acetate (59% yield).

Step 6:
To a solution of methyl 2-(3'-(3-(1-(4-(tert-butyl)benzyl)-4-ethyl-5-oxo-4,5-dihydro-1H-1,2,4-triazol-3-yl)-1,1-difluoropropyl)-4-ethoxy-[1,1'-biphenyl]-3-yl)acetate (0.029 g, 0.048 mmol) in THF (1 mL) and MeOH (1 mL) was added water (0.62 mL) and 1M aq. LiOH (0.38 mL, 0.37 mmol). The resulting mixture was then stirred at 35° C. for 48 hrs. The solvents were evaporated and the residue treated with EtOAc and a 20% aq. solution of citric acid. The organic layer was separated and extracted with water (2×). The organics were concentrated to afford 0.029 g (100% yield) of the title compound as a brown solid. LCMS (ESI), M+H 592.

Example 23: N-(6-(3-(3-(1-(4-(tert-Butyl)benzyl)-4-ethyl-5-oxo-4,5-dihydro-1H-1,2,4-triazol-3-yl)-1,1-difluoropropyl)phenyl)pyridin-3-yl)benzenesulfonamide

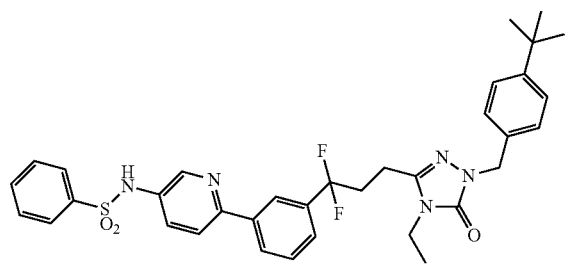 [SMILES: CCn1c(CCC(F)(F)c2cccc(-c3ccc(NS(=O)(=O)c4ccccc4)cn3)c2)nn(Cc2ccc(C(C)(C)C)cc2)c1=O]

Step 1:
3-(3-(3-Bromophenyl)-3,3-difluoropropyl)-1-(4-(tert-butyl)benzyl)-4-ethyl-1H-1,2,4-triazol-5(4H)-one (0.110 g, 0.223 mmol), bis(pinacolato)diborane (0.074 g, 0.290 mmol), KOAc (0.066 g, 0.669 mmol) were dissolved in dioxane (4 mL) and the resulting solution was subsurface purged with N$_2$ for 5 minutes after which, Pd(dppf)Cl$_2$ (0.016 g, 0.014 mmol) was added. The resulting mixture was stirred in a sealed pressure vessel at 85° C. for 16 hrs. The solution was cooled to rt and diluted with DCM and water. The organics were washed once more with water and the solution was filtered through a Na$_2$SO$_4$/paper plug and concentrated. The residue was purified by preparatory TLC using 40% EtOAc/hexanes as eluent to afford 0.065 g of 1-(4-(tert-butyl)benzyl)-3-(3,3-difluoro-3-(3-(4,4,5,5-tetramethyl-1,3,2-dioxaborolan-2-yl)phenyl)propyl)-4-ethyl-1H-1,2,4-triazol-5(4H)-one (54% yield).

Step 2:
Under a nitrogen atmosphere, 1-(4-(tert-butyl)benzyl)-3-(3,3-difluoro-3-(3-(4,4,5,5-tetramethyl-1,3,2-dioxaborolan-2-yl)phenyl)propyl)-4-ethyl-1H-1,2,4-triazol-5(4H)-one (0.065 g, 0.120 mmol) from the previous step and N-(6-bromopyridin-3-yl)benzenesulfonamide (0.042 g, 0.133 mmol) were dissolved in dioxane (3 mL). To this solution was then added a solution of saturated aqueous NaHCO$_3$ (1 mL) and the resulting biphasic mixture was then subsurface purged with N$_2$ for 5 minutes. Finally, Pd(PPh$_3$)$_4$ (0.014 g, 0.012 mmol) was added and the resulting mixture was stirred in a sealed pressure vessel at 85° C. for 16 hrs. The solution was cooled to rt, evaporated, and diluted with EtOAc and 1:1 brine/water. The organics were washed once more with water and brine. The organics were then filtered through a Na$_2$SO$_4$/paper plug and concentrated. The residue was purified by preparatory LCMS (C$_{18}$ reverse phase) using 0% to 100% CH$_3$CN/water as eluent to afford 0.013 g of the title compound (17% yield). LCMS (ESI), M+H 646.

Example 24: 2-(5-(6-(3-(1-(4-(tert-Butyl)benzyl)-4-ethyl-5-oxo-4,5-dihydro-1H-1,2,4-triazol-3-yl)propyl)pyridin-2-yl)-2-methoxyphenyl)acetic Acid

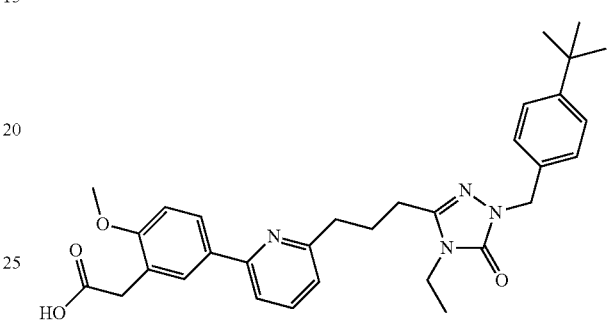

Step 1:
To a degassed (sparged) solution of 2-bromo-6-chloropyridine (2.0 g, 10.4 mmol) in THF (75 mL) was added Pd(PPh$_3$)$_4$ (200 mg) followed by a solution of (4-ethoxy-4-oxobutyl)zinc(II) bromide (0.5M in THF; 20.8 mL, 20.8 mmol). After stirring at room temperature for 2 hrs, the solution was poured on to a mixture of ice and 1N HCl, extracted with EtOAc, the organic phase separated, dried (MgSO$_4$), filtered and evaporated. The isolated residue was purified on silica gel (0 to 30% EtOAc in hexanes) to afford 1.4 g of ethyl 4-(6-chloropyridin-2-yl)butanoate.

Step 2:
Lithium hydroxide monohydrate (400 mg) was added to a solution of ethyl 4-(6-chloropyridin-2-yl)butanoate (1.4 g, 7.0 mmol) in a mixture of THF (20 mL), MeOH (8 mL) and water (8 mL). After stirring at room temperature for 1 hr, the solution was diluted with EtOAc and water. Solid citric acid was then added until an acidic pH was attained and the organic phase separated, washed with water, dried (MgSO$_4$), filtered and evaporated to afford 4-(6-chloropyridin-2-yl)butanoic acid. The crude product thus obtained was used without further purification.

Step 3:
To a solution of 4-(6-chloropyridin-2-yl)butanoic acid (600 mg, 3.0 mmol) in DMF (15 mL) was added HATU (1.3 g, 3.42 mmol) followed by DIPEA (1.6 mL) and stirred at RT for 30 minutes. Intermediate (M) (1.2 g, 3.47 mmol) was then added and the solution allowed to stir at rt for 24 hrs. The reaction mixture was partitioned between EtOAc and water, the organic phase separated, dried (MgSO$_4$) and filtered. To the filtrate was then added camphorsulfonic acid (697 mg, 3.0 mmol) and the resulting mixture was heated to reflux for 24 hrs. After cooling, the solution was neutralized following the addition of saturated aqueous NaHCO$_3$. The organic phase was then separated, dried (MgSO$_4$), filtered and evaporated in vacuo. The residue thus obtained was purified on silica gel, eluting with a gradient of 0 to 80%

EtOAc in hexanes to afford 1-(4-(tert-butyl)benzyl)-3-(3-(6-chloropyridin-2-yl)propyl)-4-ethyl-1H-1,2,4-triazol-5(4H)-one.

Step 4:

The title compound was then obtained as previously described for Example 1, whereby the requisite boronate was cross-coupled and the resulting ester was then hydrolyzed under the same conditions.

Example 25: 3-(3-(3'-(1H-Tetrazol-5-yl)-[1,1'-biphenyl]-3-yl)propyl)-1-(4-(tert-butyl)benzyl)-4-ethyl-1H-1,2,4-triazol-5(4H)-one

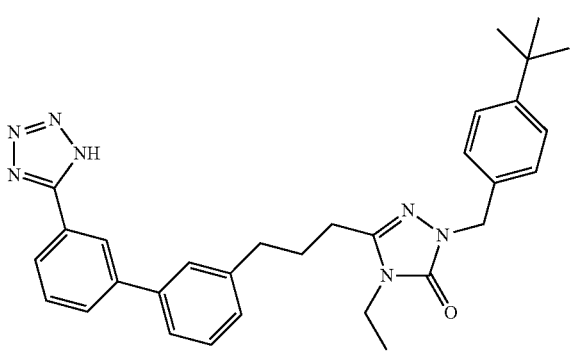 [SMILES: CCn1c(CCCc2cccc(-c3cccc(-c4nnn[nH]4)c3)c2)nn(Cc2ccc(C(C)(C)C)cc2)c1=O]

A mixture of 3-(3-(3'-bromo-[1,1'-biphenyl]-3-yl)propyl)-1-(4-(tert-butyl)benzyl)-4-ethyl-1H-1,2,4-triazol-5(4H)-one (112 mg, 0.245 mmol), 3-(tetrazol-5 yl)phenylboronic acid (46 mg, 0.245 mmol, 1.0 eq) and potassium phosphate tribasic (208 mg, 0.980 mmol, 4 eq) were taken up in a DME (2 mL) and water (1 mL) solution. To this was added tris(dibenzylideneacetone)dipalladium(0) (6 mg, 0.0061 mmol, 0.025 eq) and 2-dicyclohexylphosphino-2',6'-dimethoxybiphenyl (20 mg, 0.049 mmol, 0.2 eq), and the resulting mixture was stirred at 85° C. under an atmosphere of N$_2$ for 24 hr. The reaction mixture was cooled to room temperature and the solvent was removed under vacuum. The crude material was then partitioned between water and EtOAc. The aqueous layer was separated and extracted further with EtOAc (3×20 mL). The combined organic extracts were dried over anhydrous Na$_2$SO$_4$. The solvent was evaporated in vacuum to obtain the crude product. The crude product was purified on reverse phase HPLC to afford a white solid (20 mg, 16% yield) LC-MS: 521 (M+H)+.

Example 26: 2-(5-(4-(3-(1-(4-(tert-Butyl)benzyl)-4-ethyl-5-oxo-4,5-dihydro-1H-1,2,4-triazol-3-yl)propyl)pyrimidin-2-yl)-2-ethoxyphenyl)acetic Acid

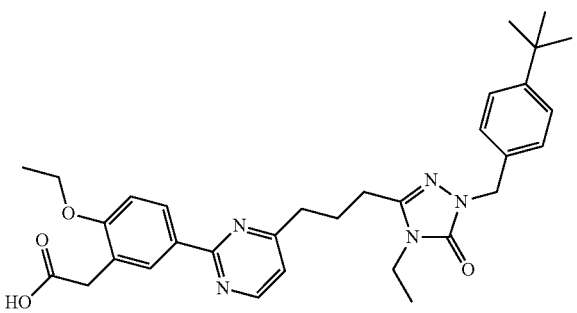 [SMILES: CCOc1ccc(-c2nccc(CCCc3nn(Cc4ccc(C(C)(C)C)cc4)c(=O)n3CC)n2)cc1CC(=O)O]

Step 1:

To a THF solution of 2,4-dichloropyrimidine (1.00 g, 6.71 mmol) was added at 0° C. (4-ethoxy-4-oxobutyl)zinc(II) bromide (13.42 mL, 6.71 mmol, 0.5 M in THF) followed by Pd(PPh)$_4$ (0.194 g, 0.167 mmol). The reaction mixture thus obtained was then allowed to slowly warm to rt. By TLC, it was noted that this reaction had stalled after 1.5 hr, so another spatula tip of Pd(PPh)$_4$ was then added and reaction was allowed to continue at rt for another 16 hrs. The reaction mixture was then poured into ice-cold 0.5M aq. HCl solution and diluted with EtOAc and brine. The organics were separated, washed once more with water and then concentrated. The residue was purified by column chromatography using 0%-50% gradient EtOAc/hexanes as eluent to afford 0.930 g (60% yield) of ethyl 4-(2-chloropyrimidin-4-yl)butanoate.

Step 2:

Under a nitrogen atmosphere, ethyl 4-(2-chloropyrimidin-4-yl)butanoate (0.193 g, 0.842 mmol) and ethyl 2-(2-ethoxy-5-(4,4,5,5-tetramethyl-1,3,2-dioxaborolan-2-yl)phenyl)acetonitrile (0.220 g, 0.766 mmol) were dissolved in dioxane (8 mL) to which was added a solution of saturated aqueous NaHCO$_3$ (4 mL). The resulting solution was then subsurface purged with N$_2$ for 5 minutes after which, Pd(PPh)$_4$ (0.088 g, 0.077 mmol) was added. The resulting mixture was stirred in a sealed pressure vessel at 85° C. for 16 hrs. The solution was cooled to rt, evaporated, and diluted with EtOAc and brine. The aqueous layer was extracted twice more with DCM and the combined organics were concentrated. The residue was purified by column chromatography using 0%-60% gradient EtOAc/hexanes as eluent to afford 0.144 g (54% yield) of 4-(2-(3-(cyanomethyl)-4-ethoxyphenyl)pyrimidin-4-yl)butanoate.

Step 3:

To a solution of ethyl 4-(2-(3-(cyanomethyl)-4-ethoxyphenyl)pyrimidin-4-yl)butanoate (0.360 g, 1.02 mmol) in THF (8 mL) and MeOH (8 mL) was added 1M aq. LiOH (8.02 mL, 8.02 mmol). The resulting mixture was then stirred at rt for 1.5 hrs. The solvents were evaporated and the residue treated with EtOAc and a 20% aq. solution of citric acid. The organic layer was separated and washed with water (2×). The organics were then filtered through a Na$_2$SO$_4$/paper plug and concentrated. The resulting crude 4-(2-(3-(cyanomethyl)-4-ethoxyphenyl)pyrimidin-4-yl)butanoic acid thus obtained was used directly in the next step.

Step 4:

4-(2-(3-(Cyanomethyl)-4-ethoxyphenyl)pyrimidin-4-yl)butanoic acid (0.32 g, 0.984 mmol), Hunig's base (0.45 mL, 1.86 mmol) and 2-(7-aza-1H-benzotriazole-1-yl)-1,1,3,3-tetramethyluronium hexafluorophosphate (0.449 g, 1.18 mmol) were combined in anhydrous DMF (10 mL). The reaction solution was stirred for 40 min at rt before intermediate (M) (0.248 g, 0.717 mmol), dissolved in a minimal amount of DMF, was added dropwise. The resulting solution was allowed to stir at rt for 16 h. The reaction mixture was then evaporated and diluted with EtOAc and water. The organics were washed sequentially with saturated aqueous NaHCO$_3$ and brine, dried over sodium sulfate, filtered and the filtrate concentrated. The crude 1-(4-(tert-butyl)benzyl)-

2-(4-(2-(3-(cyanomethyl)-4-ethoxyphenyl)pyrimidin-4-yl)butanoyl)-N-ethylhydrazinecarboxamide thus obtained was used as is in the next step.

Step 5:

To an EtOAc solution (10 mL) of 1-(4-(tert-butyl)benzyl)-2-(4-(2-(3-(cyanomethyl)-4-ethoxyphenyl)pyrimidin-4-yl)butanoyl)-N-ethylhydrazinecarboxamide (0.547 g, 0.982 mmol) was added camphorsulfonic acid (0.228 g, 0.982 mmol) and the resulting solution was heated at reflux for 16 h. The reaction mixture was then diluted with EtOAc and brine. The organics were separated and washed sequentially with 1M NaOH, water, and brine. The organic extract was then dried over sodium sulfate, filtered and the filtrate concentrated. The residue was purified by column chromatography using 0%-50% gradient acetone/hexanes as eluent to afford 0.300 g (57% yield, three steps) of 2-(5-(4-(3-(1-(4-(tert-butyl)benzyl)-4-ethyl-5-oxo-4,5-dihydro-1H-1,2,4-triazol-3-yl)propyl)pyrimidin-2-yl)-2-ethoxyphenyl)acetonitrile.

Step 6:

To a solution of 2-(5-(4-(3-(1-(4-(tert-butyl)benzyl)-4-ethyl-5-oxo-4,5-dihydro-1H-1,2,4-triazol-3-yl)propyl)pyrimidin-2-yl)-2-ethoxyphenyl)acetonitrile (0.100 g, 0.186 mmol) in ethylene glycol (6 mL) and water (1.5 mL) was added 18M KOH (0.104 mL, 1.86 mmol). The resulting mixture was then stirred at 120° C. for 16 hrs. The reaction was quenched with 1 M aq. HCl (1.86 mL, 1.86 mmol) and the residue was diluted with EtOAc and water. The organic layer was separated and washed further with water (2×). The organics were then filtered through a $Na_2SO_4$/paper plug and concentrated. The organics were concentrated to afford 0.095 g (92% yield) of the title compound as a yellow solid. LCMS (ESI), M+H 558.

Example 27: 2-(5-(6-(3-(1-(4-(tert-Butyl)benzyl)-4-ethyl-5-oxo-4,5-dihydro-1H-1,2,4-triazol-3-yl)propyl)pyrimidin-4-yl)-2-ethoxyphenyl) acetic Acid

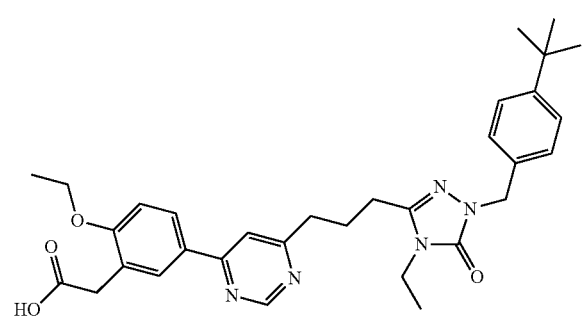 [SMILES: CCOc1ccc(-c2cc(CCCc3nn(Cc4ccc(C(C)(C)C)cc4)c(=O)n3CC)ncn2)cc1CC(=O)O]

The title compound was prepared in an analogous fashion to Example 26 but using instead the requisite commercially available 4,6-dichloropyrimidine in the first step. LCMS (ESI), M+H 558.

Examples 28 (R=Me), 29 (R=Et) and 30 (R=nPr); (3'-(3-(1-(4-(tert-Butyl)benzyl)-4-ethyl-5-oxo-4,5-dihydro-1H-1,2,4-triazol-3-yl)propyl)-3-alkoxy-[1,1'-biphenyl]-4-yl)acetic Acid

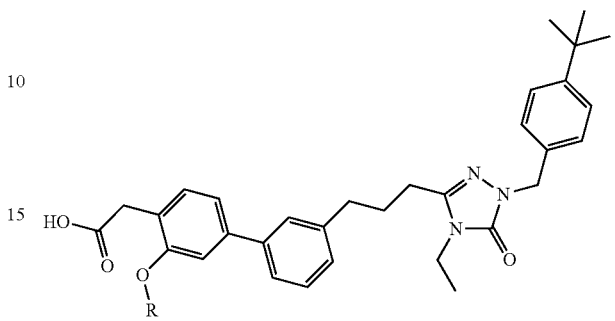

Example 31: 2-(3'-(3-(1-(4-(tert-Butyl)benzyl)-4-ethyl-5-oxo-4,5-dihydro-1H-1,2,4-triazol-3-yl)propyl)-3-hydroxy-[1,1'-biphenyl]-4-yl)acetic Acid

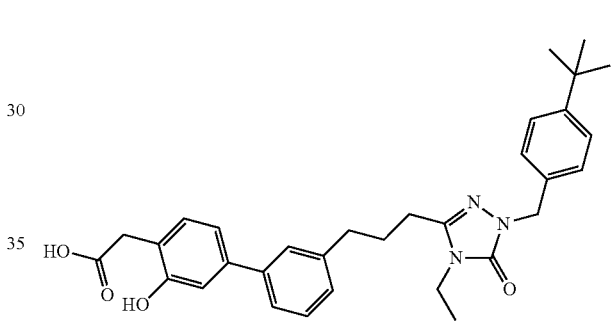

Step 1:

In a 75 mL screw-cap reaction flask equipped with a magnetic stirrer was combined 1-(4-(tert-butyl)benzyl)-4-ethyl-3-(3-(3-(4,4,5,5-tetramethyl-1,3,2-dioxaborolan-2-yl)phenyl)propyl)-1H-1,2,4-triazol-5(4H)-one (300 mg, 0.60 mmol), methyl 2-(benzyloxy)-5-bromobenzoate (200 mg, 0.60 mmol) and $K_3PO_4$ (330 mg, 2.4 mmol) in DME (4 mL) and water (2 mL). The resulting biphasic mixture was then subsurface purged with $N_2$ for 15 min after which, $Pd_2(dba)_3$ (14 mg, 0.015 mmol) and 2-dicyclohexylphosphino-2',6'-dimethoxybiphenyl (25 mg, 0.060 mmol) were added in one rapid portion. The now golden-yellow biphasic suspension was subsurface purged with $N_2$ for another 15 min before the vessel was tightly sealed and then heated at 85° C. for 15 h. The now dark orange reaction suspension was allowed to cool to RT, diluted with tert-butyl methyl ether and washed sequentially with 10% aq. HCl, water and brine. The organic extract thus obtained was then dried over $Na_2SO_4$, decolorized with activated charcoal and finally filtered through a pad of ether-wetted celite. The insolubles were rinsed further with tert-butyl methyl ether and the filtrate thus obtained was concentrated in vacuo. Purification of the crude product thus obtained by way of column chromatography ($SiO_2$, gradient elution, 4:1 Hex: EtOAc-EtOAc) furnished 2-(3-(benzyloxy)-3'-(3-(1-(4-(tert-butyl)benzyl)-4-ethyl-5-oxo-4,5-dihydro-1H-1,2,4-triazol-3-yl)propyl)-[1,1'-biphenyl]-4-yl)acetate as a pale yellow oil (190 mg, 49% yield).

Step 2:

In a 500 mL Parr shaker flask was dissolved methyl 2-(3-(benzyloxy)-3'-(3-(1-(4-(tert-butyl)benzyl)-4-ethyl-5-oxo-4,5-dihydro-1H-1,2,4-triazol-3-yl)propyl)-[1,1'-biphenyl]-4-yl)acetate (190 mg, 29 mmol) from the previous step in MeOH (10 mL). To this was then added Pd/C (10% wt/wt wet, 120 mg, 0.06 mmol) and the resulting suspension was thoroughly deoxygenated via subsurface purging with nitrogen. The reaction vessel was then connected to a Parr shaker and the reaction suspension was shaken under 50 psi of $H_2$ for 5 h. The excess $H_2$ was discharged from the vessel and the reaction was immediately quenched with DCM. The deactivated catalyst was then removed via filtration through a pad of DCM-wetted celite and the insolubles were washed thoroughly with DCM. The filtrate thus obtained was concentrated in vacuo to furnish a pale yellow solid. Purification of the crude product thus obtained by way of column chromatography ($SiO_2$, gradient elution, 4:1 Hex: EtOAc-EtOAc) furnished methyl 2-(3'-(3-(1-(4-(tert-butyl)benzyl)-4-ethyl-5-oxo-4,5-dihydro-1H-1,2,4-triazol-3-yl)propyl)-3-hydroxy-[1,1'-biphenyl]-4-yl)acetate as a pale yellow solid (110 mg, 66% yield).

Step 3:

In a 50 mL RBF equipped with a magnetic stirrer was added methyl 2-(3'-(3-(1-(4-(tert-butyl)benzyl)-4-ethyl-5-oxo-4,5-dihydro-1H-1,2,4-triazol-3-yl)propyl)-3-hydroxy-[1,1'-biphenyl]-4-yl)acetate (35 mg, 0.065 mmol) from the previous step in THF (1 mL) and MeOH (0.5 mL). To this was then added 2N aq. LiOH (0.2 mL, 0.4 mmol) and the resulting solution was stirred at RT for 16 h. The volatiles were then removed in vacuo and the resulting residue was acidified with 1 N aq. HCl and extracted with DCM (3×10 mL). The combined organic extracts were then washed further with water and brine, dried over $Na_2SO_4$ and filtered. Concentration of the filtrate thus obtained in vacuo furnished the title compound as a white solid (33 mg, 66% yield). LC-MS: 528 (M+H)$^+$, 526 (M−H)$^+$.

Example 32: 2-(3'-(3-(1-(4-(tert-Butyl)benzyl)-4-ethyl-5-oxo-4,5-dihydro-1H-1,2,4-triazol-3-yl)propyl)-4-isopropoxy-[1,1'-biphenyl]-3-yl)acetic Acid

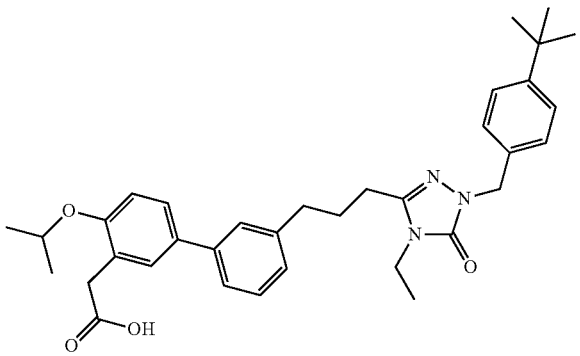 [SMILES: CCn1c(CCCc2cccc(-c3ccc(OC(C)C)c(CC(=O)O)c3)c2)nn(Cc2ccc(C(C)(C)C)cc2)c1=O]

Example 33: 2-(3'-(3-(1-(4-(tert-Butyl)benzyl)-4-ethyl-5-oxo-4,5-dihydro-1H-1,2,4-triazol-3-yl)propyl)-4-(2-(dimethylamino)ethoxy)-[1,1'-biphenyl]-3-yl)acetic Acid

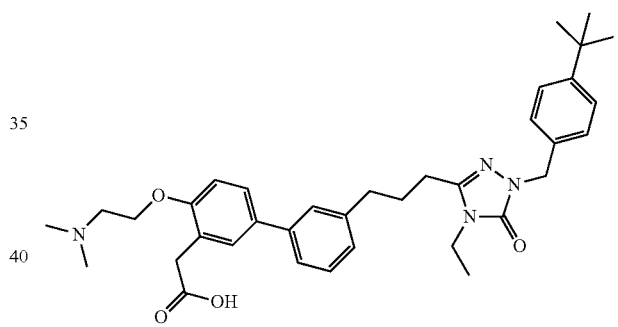

| Example | Structure | Human PPARα Reporter Assay - Luciferase IC$_{50}$ (nM) | MS(ESI) |
|---|---|---|---|
| 1 | 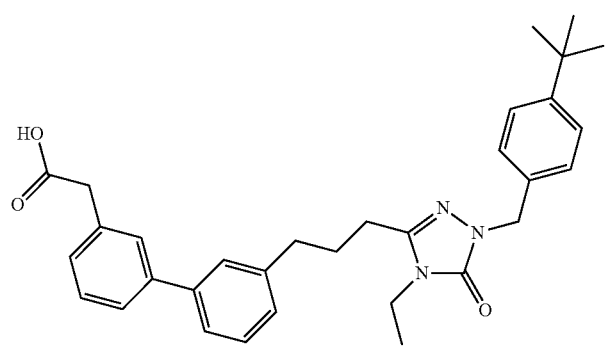 [SMILES: CCn1c(CCCc2cccc(-c3cccc(CC(=O)O)c3)c2)nn(Cc2ccc(C(C)(C)C)cc2)c1=O] | 346 | 512 (M + H) |

-continued

| Example | Structure | Human PPARα Reporter Assay - Luciferase IC$_{50}$ (nM) | MS(ESI) |
|---|---|---|---|
| 2 | 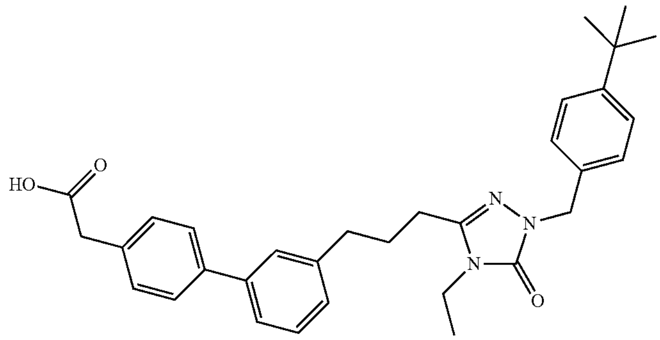 [SMILES: CCn1c(CCCc2cccc(-c3ccc(CC(=O)O)cc3)c2)nn(Cc2ccc(C(C)(C)C)cc2)c1=O] | 324 | 512 (M + H) |
| 3 | 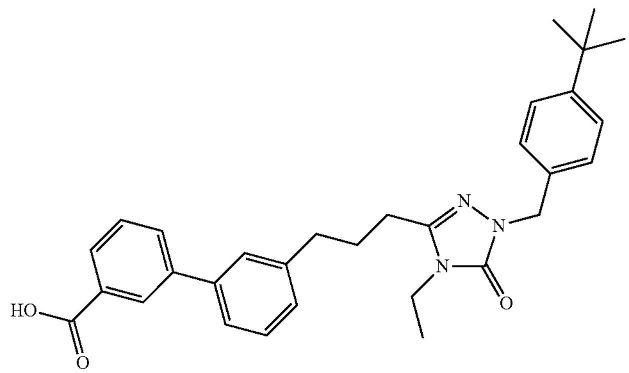 [SMILES: CCn1c(CCCc2cccc(-c3cccc(C(=O)O)c3)c2)nn(Cc2ccc(C(C)(C)C)cc2)c1=O] | 1333 | 498 (M + H) |
| 4 | 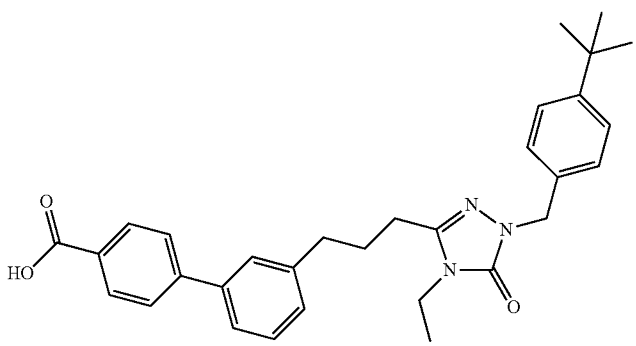 [SMILES: CCn1c(CCCc2cccc(-c3ccc(C(=O)O)cc3)c2)nn(Cc2ccc(C(C)(C)C)cc2)c1=O] | 110 | 498 (M + H) |
| 5 | 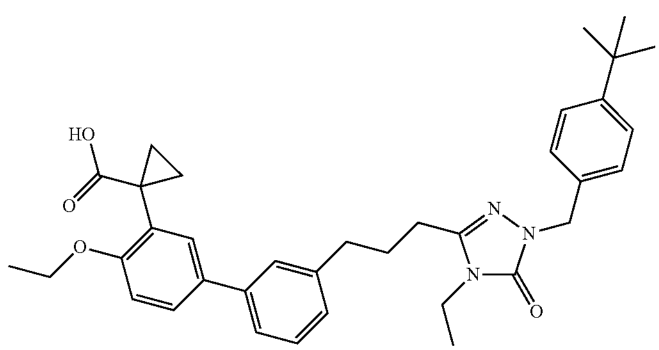 [SMILES: CCOc1ccc(-c2cccc(CCCc3nn(Cc4ccc(C(C)(C)C)cc4)c(=O)n3CC)c2)cc1C1(C(=O)O)CC1] | 137 | 582 (M + H) |

-continued
| Example | Structure | Human PPARα Reporter Assay - Luciferase IC$_{50}$ (nM) | MS(ESI) |
|---|---|---|---|
| 6 | 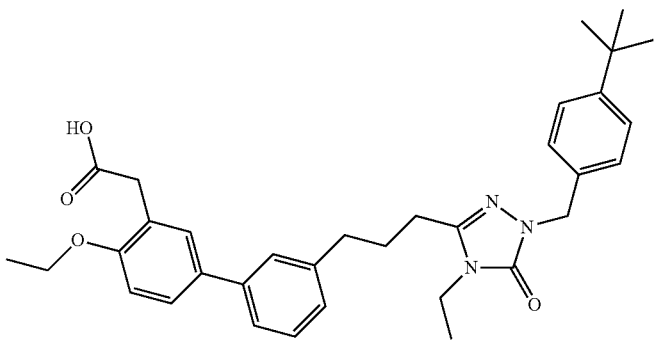 [SMILES: CCOc1ccc(-c2cccc(CCCc3nn(Cc4ccc(C(C)(C)C)cc4)c(=O)n3CC)c2)cc1CC(=O)O] | 58 | 554 (M − H) |
| 7 | 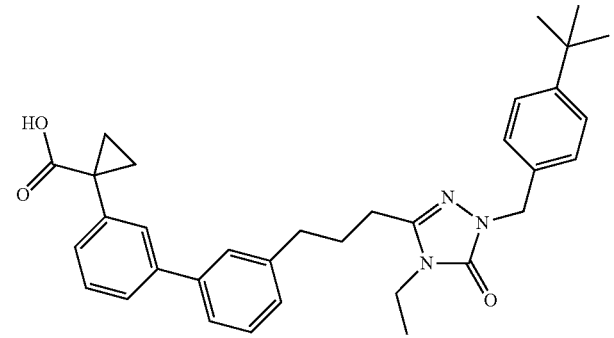 [SMILES: CCn1c(CCCc2cccc(-c3cccc(C4(C(=O)O)CC4)c3)c2)nn(Cc2ccc(C(C)(C)C)cc2)c1=O] | 77 | 538 (M + H) |
| 8 | 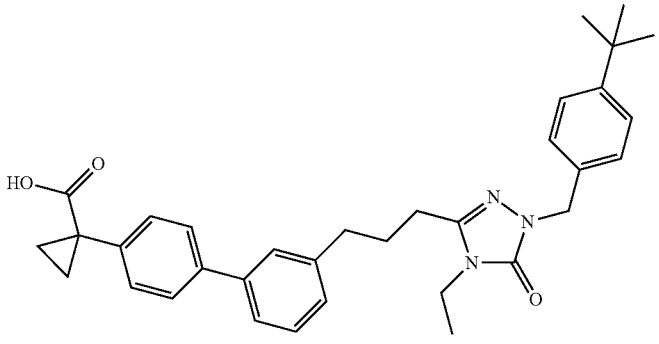 [SMILES: CCn1c(CCCc2cccc(-c3ccc(C4(C(=O)O)CC4)cc3)c2)nn(Cc2ccc(C(C)(C)C)cc2)c1=O] | 487 | 538 (M + H) |
| 9 | 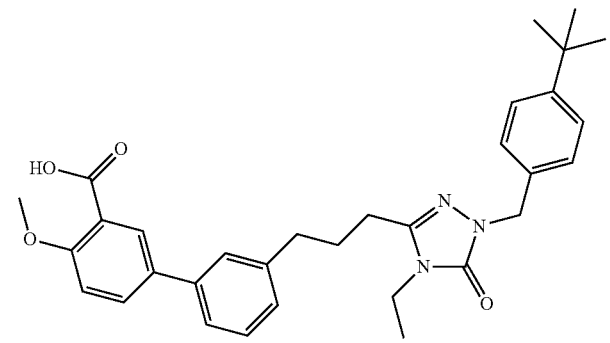 [SMILES: CCn1c(CCCc2cccc(-c3ccc(OC)c(C(=O)O)c3)c2)nn(Cc2ccc(C(C)(C)C)cc2)c1=O] | 548 | 528 (M + H) |

-continued
| Example | Structure | Human PPARα Reporter Assay - Luciferase IC$_{50}$ (nM) | MS(ESI) |
|---|---|---|---|
| 10 | 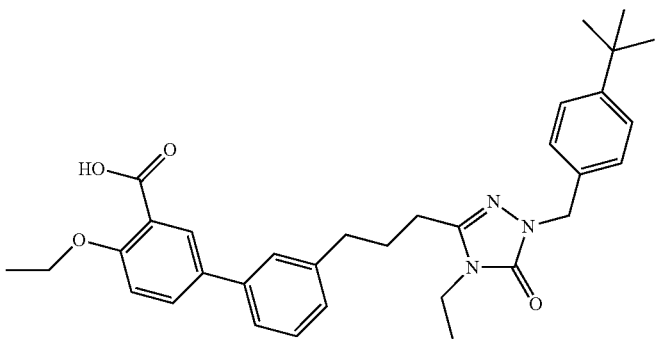 [SMILES: CCOc1ccc(-c2cccc(CCCc3nn(Cc4ccc(C(C)(C)C)cc4)c(=O)n3CC)c2)cc1C(=O)O] | 211 | 542 (M + H) |
| 11 | 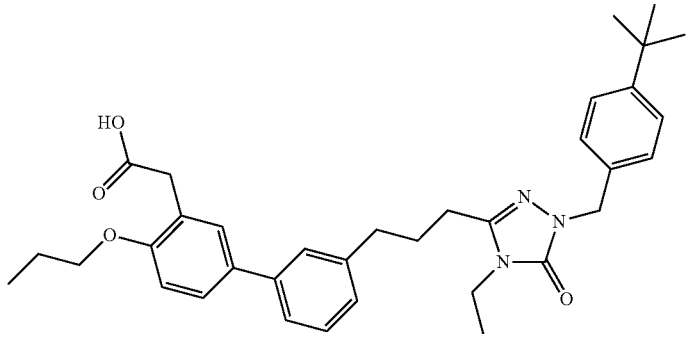 [SMILES: CCCOc1ccc(-c2cccc(CCCc3nn(Cc4ccc(C(C)(C)C)cc4)c(=O)n3CC)c2)cc1CC(=O)O] | 48 | 570 (M + H) |
| 12 | 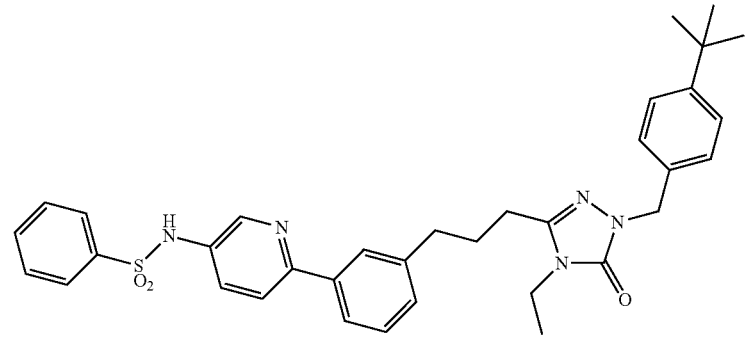 [SMILES: CCn1c(CCCc2cccc(-c3ccc(NS(=O)(=O)c4ccccc4)cn3)c2)nn(Cc2ccc(C(C)(C)C)cc2)c1=O] | 302 | 610 (M + H) |
| 13 | 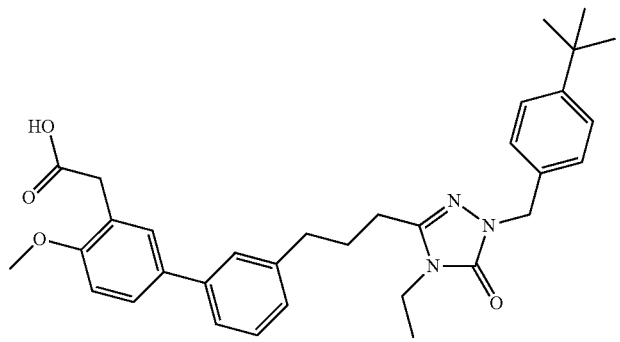 [SMILES: CCn1c(CCCc2cccc(-c3ccc(OC)c(CC(=O)O)c3)c2)nn(Cc2ccc(C(C)(C)C)cc2)c1=O] | 197 | 542 (M + H) |

-continued

| Example | Structure | Human PPARα Reporter Assay - Luciferase IC$_{50}$ (nM) | MS(ESI) |
| --- | --- | --- | --- |
| 14 | 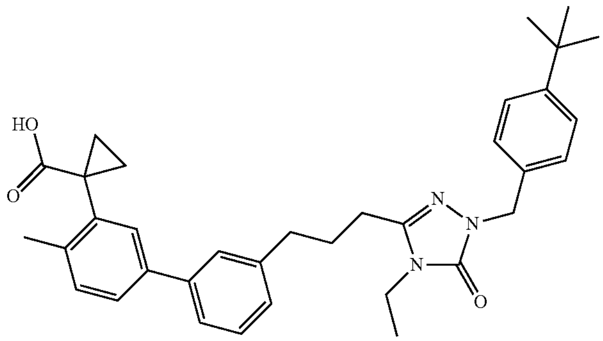 [SMILES: CCn1c(CCCc2cccc(-c3ccc(C)c(C4(C(=O)O)CC4)c3)c2)nn(Cc2ccc(C(C)(C)C)cc2)c1=O] | 234 | 552 (M + H) |
| 15 | 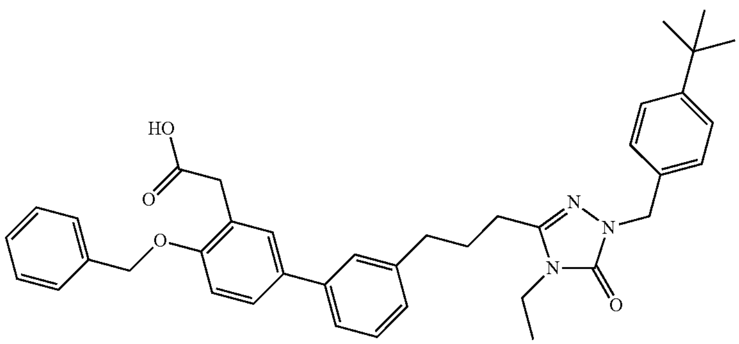 [SMILES: CCn1c(CCCc2cccc(-c3ccc(OCc4ccccc4)c(CC(=O)O)c3)c2)nn(Cc2ccc(C(C)(C)C)cc2)c1=O] | 122 | 618 (M + H) |
| 16 | 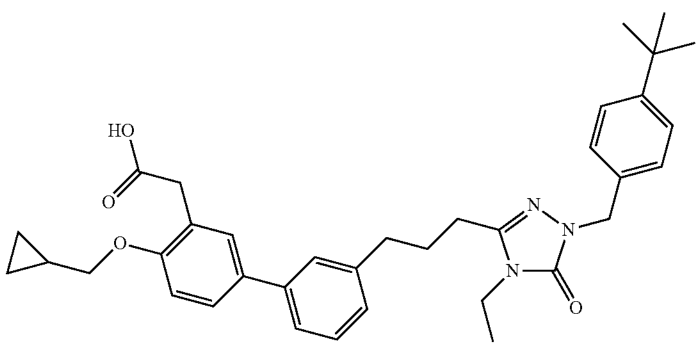 [SMILES: CCn1c(CCCc2cccc(-c3ccc(OCC4CC4)c(CC(=O)O)c3)c2)nn(Cc2ccc(C(C)(C)C)cc2)c1=O] | 141 | 582 (M + H) |
| 17 | 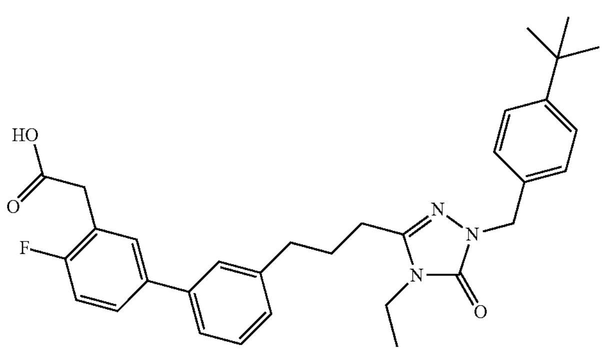 [SMILES: CCn1c(CCCc2cccc(-c3ccc(F)c(CC(=O)O)c3)c2)nn(Cc2ccc(C(C)(C)C)cc2)c1=O] | 83 | 530 (M + H) |

-continued

| Example | Structure | Human PPARα Reporter Assay - Luciferase IC$_{50}$ (nM) | MS(ESI) |
|---|---|---|---|
| 18 | 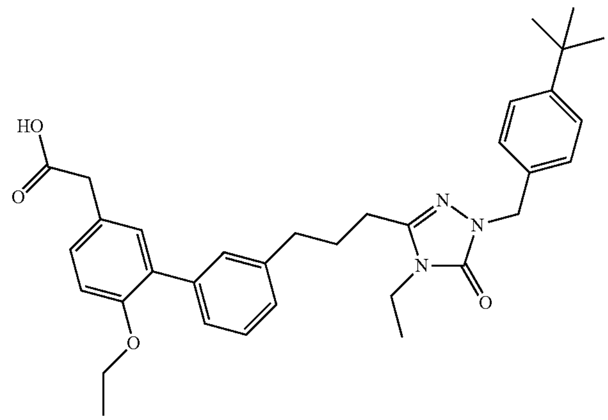 [SMILES: CCOc1ccc(CC(=O)O)cc1-c1cccc(CCCc2nn(Cc3ccc(C(C)(C)C)cc3)c(=O)n2CC)c1] | 750 | 556 (M + H) |
| 19 | 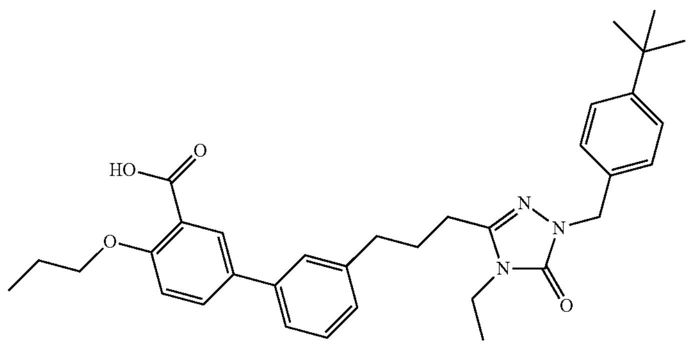 [SMILES: CCCOc1ccc(-c2cccc(CCCc3nn(Cc4ccc(C(C)(C)C)cc4)c(=O)n3CC)c2)cc1C(=O)O] | 119 | 556 (M + H) |
| 20 | 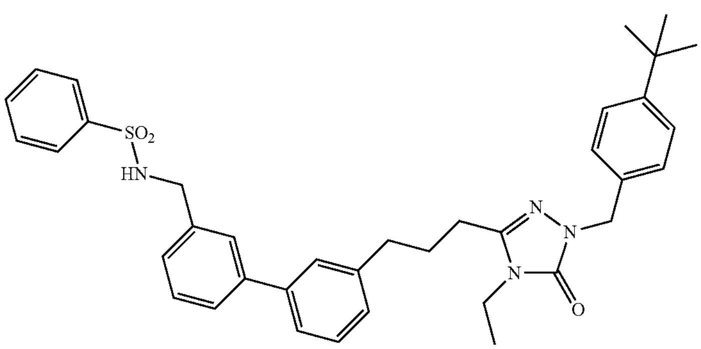 [SMILES: CCn1c(CCCc2cccc(-c3cccc(CNS(=O)(=O)c4ccccc4)c3)c2)nn(Cc2ccc(C(C)(C)C)cc2)c1=O] | 896 | 623 (M + H) |
| 21 | 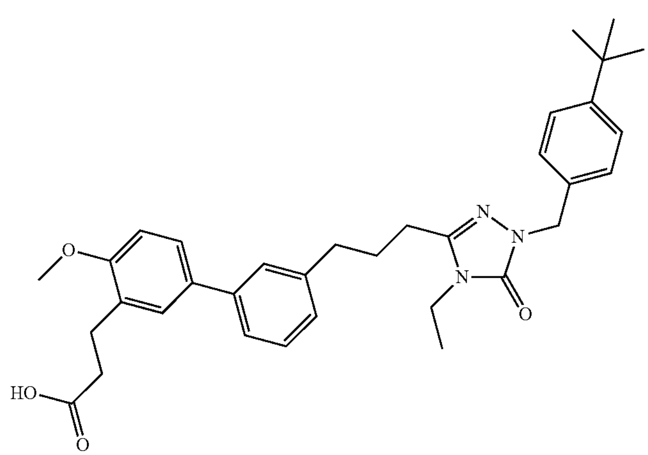 [SMILES: CCn1c(CCCc2cccc(-c3ccc(OC)c(CCC(=O)O)c3)c2)nn(Cc2ccc(C(C)(C)C)cc2)c1=O] | 610 | 556 (M + H) |

-continued

| Example | Structure | Human PPARα Reporter Assay - Luciferase IC$_{50}$ (nM) | MS(ESI) |
|---|---|---|---|
| 22 | 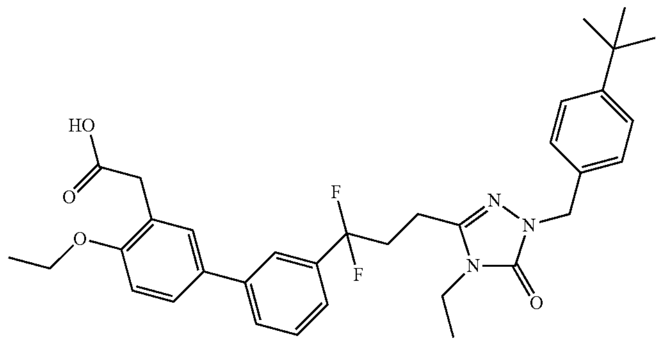 [SMILES: CCOc1ccc(-c2cccc(C(F)(F)CCc3nn(Cc4ccc(C(C)(C)C)cc4)c(=O)n3CC)c2)cc1CC(=O)O] | 64 | 592 (M + H) |
| 23 | 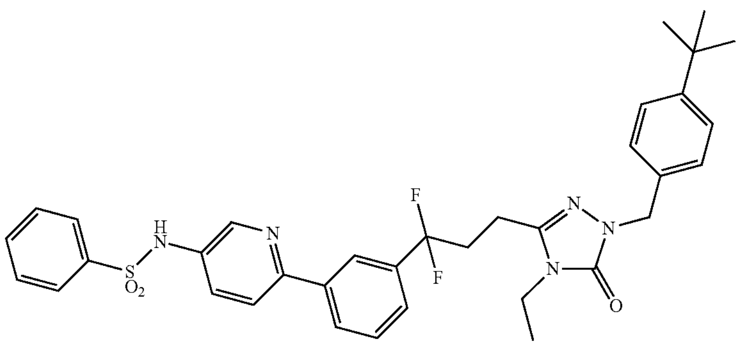 [SMILES: CCn1c(CCC(F)(F)c2cccc(-c3ccc(NS(=O)(=O)c4ccccc4)cn3)c2)nn(Cc2ccc(C(C)(C)C)cc2)c1=O] | 659 | 646 (M + H) |
| 24 | 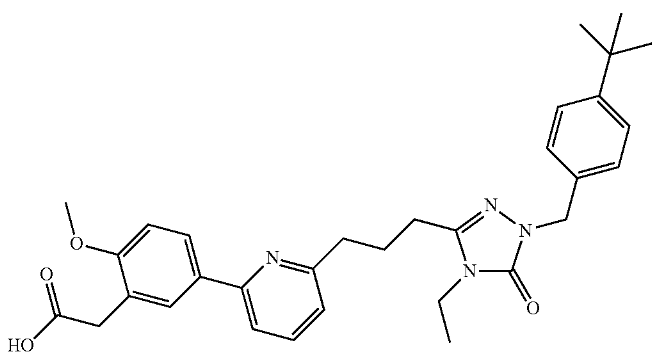 [SMILES: CCn1c(CCCc2cccc(-c3ccc(OC)c(CC(=O)O)c3)n2)nn(Cc2ccc(C(C)(C)C)cc2)c1=O] | 2531 | 543 (M + H) |
| 25 | 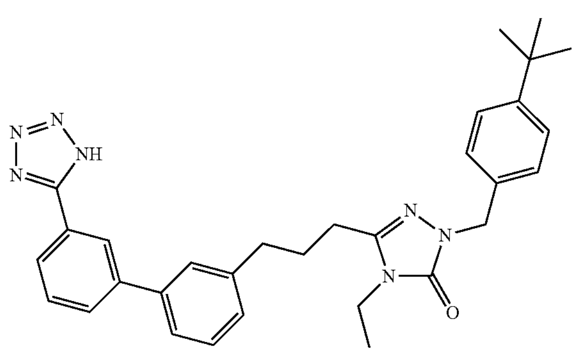 [SMILES: CCn1c(CCCc2cccc(-c3cccc(-c4nnn[nH]4)c3)c2)nn(Cc2ccc(C(C)(C)C)cc2)c1=O] | 2293 | 521 (M + H) |

-continued

| Example | Structure | Human PPARα Reporter Assay - Luciferase IC$_{50}$ (nM) | MS(ESI) |
| --- | --- | --- | --- |
| 26 | 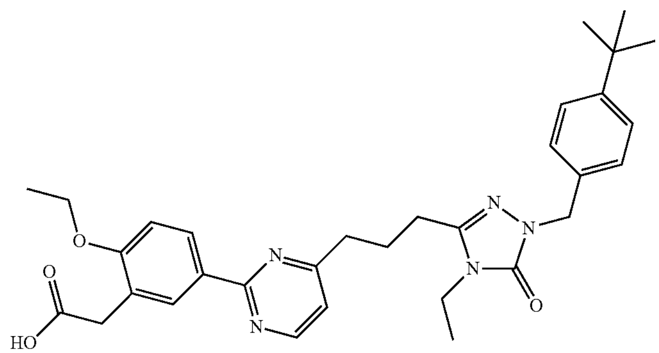 [SMILES: CCOc1ccc(-c2nccc(CCCc3nn(Cc4ccc(C(C)(C)C)cc4)c(=O)n3CC)n2)cc1CC(=O)O] | 1238 | 558 (M + H) |
| 27 | 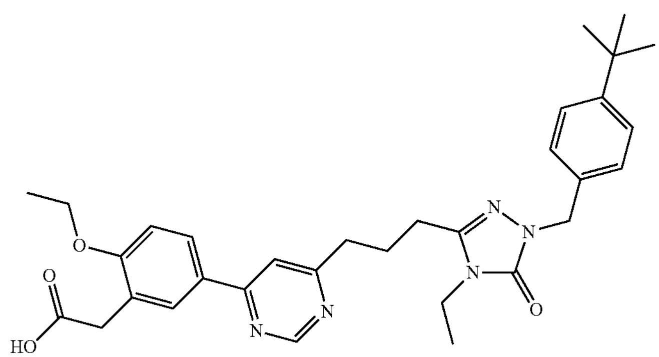 [SMILES: CCOc1ccc(-c2cc(CCCc3nn(Cc4ccc(C(C)(C)C)cc4)c(=O)n3CC)ncn2)cc1CC(=O)O] | 3431 | 558 (M + H) |
| 28 | 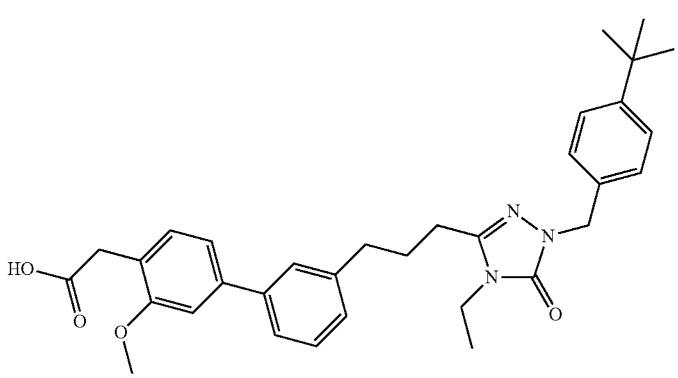 [SMILES: CCn1c(CCCc2cccc(-c3ccc(CC(=O)O)c(OC)c3)c2)nn(Cc2ccc(C(C)(C)C)cc2)c1=O] | 140 | 542 (M + H) |
| 29 | 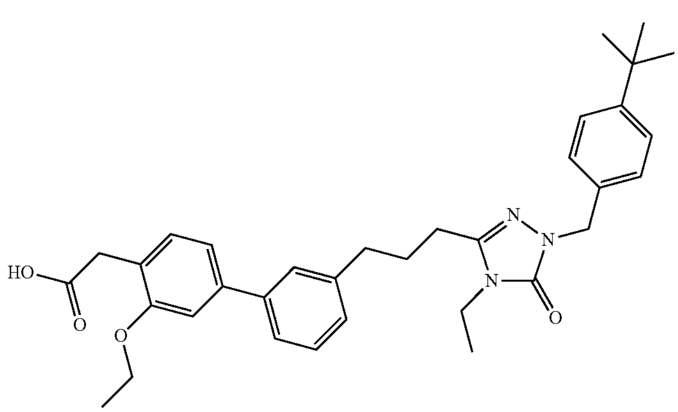 [SMILES: CCOc1cc(-c2cccc(CCCc3nn(Cc4ccc(C(C)(C)C)cc4)c(=O)n3CC)c2)ccc1CC(=O)O] | 59 | 556 (M + H) |

| Example | Structure | Human PPARα Reporter Assay - Luciferase IC$_{50}$ (nM) | MS(ESI) |
|---|---|---|---|
| 30 | 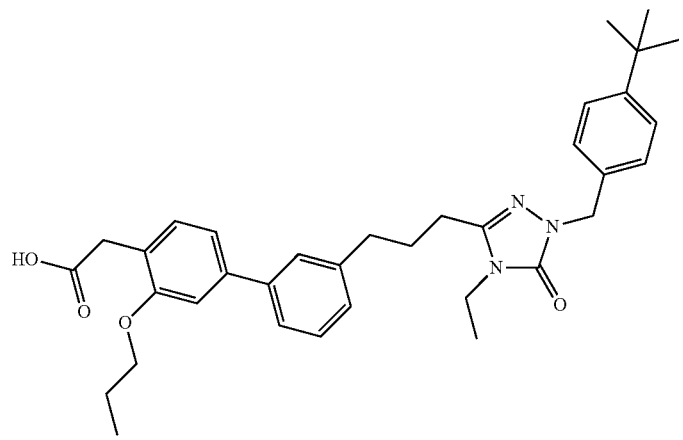 [SMILES: CCCOc1cc(-c2cccc(CCCc3nn(Cc4ccc(C(C)(C)C)cc4)c(=O)n3CC)c2)ccc1CC(=O)O] | 36 | 570 (M + H) |
| 31 | 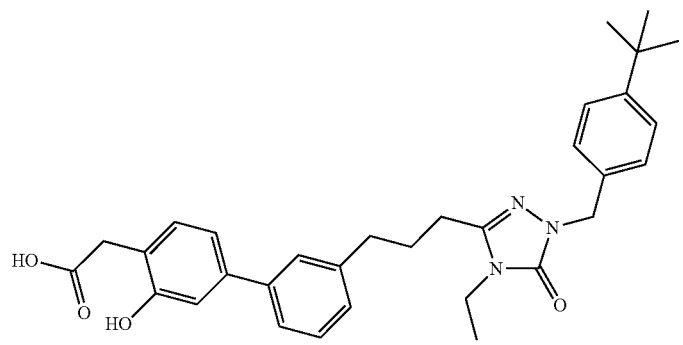 [SMILES: CCn1c(CCCc2cccc(-c3ccc(CC(=O)O)c(O)c3)c2)nn(Cc2ccc(C(C)(C)C)cc2)c1=O] |  | 528 (M + H) |
| 32 | 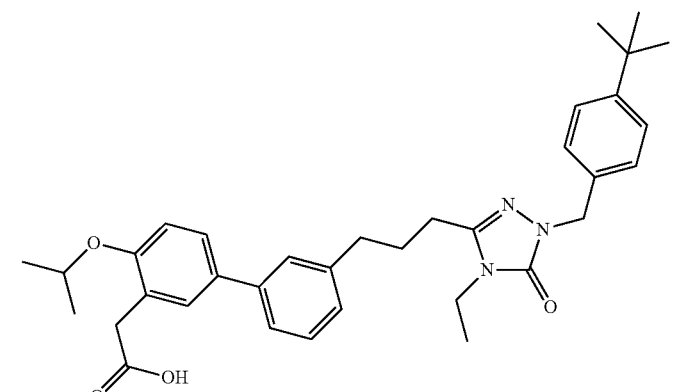 |  | 570 (M + H) |

| Example | Structure | Human PPARα Reporter Assay - Luciferase IC$_{50}$ (nM) | MS(ESI) |
|---|---|---|---|
| 33 | 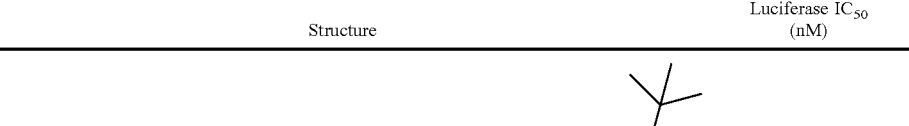 | | 599 (M + H) |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treating cancer comprising administering a therapeutically effective amount of a compound of Formula I, to a mammal in need thereof:

Formula I

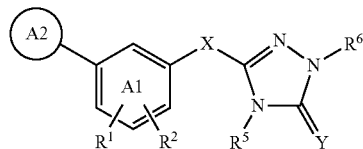

or a pharmaceutically acceptable salt thereof, wherein:
A1 is phenyl, pyrimidinyl, or pyridinyl;
A2 is A2a A2a

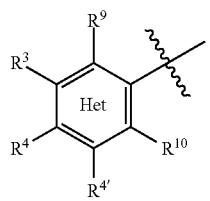

wherein A2a is phenyl or pyridinyl;
X is selected from the group consisting of —(CH$_2$)$_2$—, —(CH$_2$)$_3$—, or —(CH$_2$)$_4$—, each optionally mono- or di-substituted with halogen;

Y is O;
R$^1$ and R$^2$ are each independently selected from the group consisting of:
(a) hydrogen,
(b) halogen,
(c) —O—(R$^7$),
(d) CF$_3$,
(e) —C$_{1-6}$alkyl,
R$^3$ is selected from the group consisting of:
(a) hydrogen,
(b) —C$_{1-6}$alkyl,
(c) —O—(R$^7$), and
(d) —N(R$^7$)S(=O)$_2$(R$^8$),
wherein the alkyl portion of choice (b) is optionally substituted with halogen or hydroxyl;
R$^4$ and R$^{4'}$ are each independently selected from the group consisting of:
(a) hydrogen,
(b) —O—R$^7$,
(c) —C(R$^7$)(R$^8$)OH,
(d) —C$_{1-6}$alkyl-C(=O)OH,
(e) —C$_{3-6}$cycloalkyl-C(=O)OH,
(f) —C(=O)OH,
(g) —NHS(=O)$_2$N(R$^7$)(R$^8$),
(h) —C$_{3-6}$cycloalkyl,
(i) —CF$_3$,
(j) -heterocycle,
(k) —C$_{1-6}$alkyl, and
(l) halogen;
with the proviso that at least one of R$^3$, R$^4$ and R$^{4'}$ is other than hydrogen;
R$^5$ is selected from the group consisting of:
(a) hydrogen,
(b) —C$_{1-6}$alkyl,
(c) —C$_{1-4}$alkyl(R$^7$),
wherein the alkyl portion of choices (b) and (c) is optionally substituted with halogen or C$_{1-4}$alkyl;
R$^6$ is selected from the group consisting of:
(a) —C$_{1-6}$alkylaryl,
(b) —C$_{1-6}$alkylheteroaryl, and
(c) C$_{1-4}$alkyl(R$^7$);
wherein the alkyl portion of choices (a), (b), and (c) is optionally substituted with halogen or C$_{1-4}$alkyl, and wherein the aryl portion of choice (a), and the heteroaryl portion of choice (b) are optionally mono- or di-substituted with substituents selected from the group consisting of halogen, nitro, —$CF_3$, $C_{1-6}$alkyl, $C_{1-6}$alkoxy, halo $C_{1-6}$alkyl, $C_{3-6}$cycloalkyl, $C_{3-6}$cycloalkoxy, aryl, heteroaryl, heterocycle optionally substituted with halogen, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_o$$C_{1-6}$alkyl, S(=O)$_o$$C_{3-6}$cycloalkyl, and CN, wherein each o is independently 0, 1, or 2;

$R^7$ and $R^8$ are each independently selected from the group consisting of:
(a) hydrogen,
(b) —$C_{1-6}$alkyl,
(c) —$C_{3-6}$cycloalkyl,
(d) -aryl,
(e) -heteroaryl, and
(f) $CF_3$; and $R^9$ and $R^{10}$ are each independently selected from the group consisting of:
(a) hydrogen,
(b) —$C_{1-6}$alkyl,
(c) halogen,
(d) $CF_3$, and
(e) $C_{1-6}$alkoxy wherein the alkyl of choice (b) is optionally mono-, di- or tri-substituted with halogen, wherein the cancer is selected from the group consisting of prostate cancer, breast cancer, ovarian cancer, liver cancer, kidney cancer, colon cancer, pancreatic cancer, human chronic lymphocytic leukemia, and melanoma.

2. The method according to claim 1, or a pharmaceutically acceptable salt thereof, wherein X is —$CH_2CH_2CH_2$— or —$CF_2CH_2CH_2$—.

3. The method according to claim 1, or a pharmaceutically acceptable salt thereof, wherein: A1 is phenyl, and $R^1$ and $R^2$ are each hydrogen.

4. The method according to claim 1, or a pharmaceutically acceptable salt thereof, wherein: A2 is A2a and A2a is phenyl.

5. The method according to claim 1, or a pharmaceutically acceptable salt thereof, wherein: $R^3$ is selected from the group consisting of:
(a) hydrogen,
(b) —O—(R),
(c) —N($R^7$)S(=O)$_2$(R), and
(d) —$C_{1-6}$alkyl; and $R^4$ and $R^{4'}$ are each independently selected from the group consisting of:
(a) hydrogen,
(b) —O—(R),
(c) —C($R^7$)($R^8$)OH,
(d) —$C_{1-6}$alkyl-C(=O)OH,
(e) —$C_{3-6}$cycloalkyl-C(=O)OH,
(f) —C(=O)OH,
(g) $C_{3-6}$cycloalkyl,
(h) $CF_3$,
(i) heterocycle,
(j) —$C_{1-6}$alkyl, and
(k) halogen.

6. The method according to claim 1, or a pharmaceutically acceptable salt thereof, wherein:

$R^4$ and $R^{4'}$ are each independently selected from the group consisting of:
(a) —C($R^7$)($R^8$)OH,
(b) —O—(R),
(c) —$C_{1-6}$alkyl-C(=O)OH,
(d) —C(=O)OH,
(e) —$C_{3-6}$cycloalkyl,
(f) $CF_3$,
(g) heterocycle,
(h) —$C_{1-6}$alkyl, and
(i) halogen;

$R^5$ is selected from the group consisting of:
(a) hydrogen,
(b) —$C_{1-6}$alkyl, and
(c) —$C_{1-4}$alkyl(R); and $R^6$ is selected from the group consisting of:
(a) —$C_{1-6}$alkylaryl,
(b) —$C_{1-6}$alkylheteroaryl, and
(c) —$C_{1-6}$alkyl(R); and wherein the aryl portion of choice (a), and the heteroaryl portion of choice (b) are optionally mono- or di-substituted with substituents selected from the group consisting of halogen, nitro, —$CF_3$, $C_{1-6}$alkyl, $C_{1-6}$alkoxy, halo $C_{1-6}$alkyl, $C_{3-6}$cycloalkyl, $C_{3-6}$cycloalkoxy, aryl, heteroaryl, heterocycle optionally substituted with halogen, —NH($C_{1-6}$alkyl), —NH($C_{3-6}$cycloalkyl), —N($C_{1-6}$alkyl)$_2$, —N($C_{3-6}$cycloalkyl)$_2$, and CN.

7. The method according to claim 1, wherein the compound is a compound of Formula 1b:

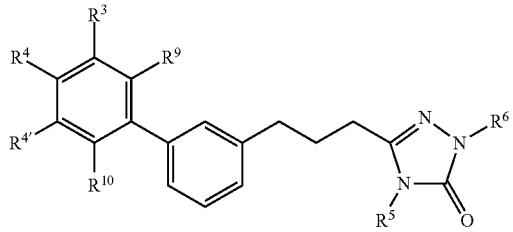

Formula 1b or a pharmaceutically acceptable salt thereof.

8. The method of claim 1, wherein the cancer is selected from the group consisting of prostate cancer, breast cancer, and ovarian cancer.

9. The method of claim 1, wherein the cancer is selected from the group consisting of liver cancer, kidney cancer, and colon cancer.

10. The method of claim 1, wherein the cancer is selected from the group consisting of human chronic lymphocytic leukemia and melanoma.

11. The method of claim 1, wherein the cancer is pancreatic cancer.

12. A method for treating cancer comprising administering a therapeutically effective amount of a compound selected from:

2-(3'-(3-(1-(4-(tert-butyl)benzyl)-4-ethyl-5-oxo-4,5-dihydro-1H-1,2,4-triazol-3-yl)propyl)-[1,1'-biphenyl]-3-yl)acetic acid, 2-(3'-(3-(1-(4-(tert-butyl)benzyl)-4-ethyl-5-oxo-4,5-dihydro-1H-1,2,4-triazol-3-yl)propyl)-[1,1'-biphenyl]-4-yl)acetic acid, 3'-(3-(1-(4-(tert-butyl)benzyl)-4-ethyl-5-oxo-4,5-dihydro-1H-1,2,4-triazol-3-yl)propyl)[1,1'-biphenyl]-3-carboxylic acid, 3'-(3-(1-(4-(tert-butyl)benzyl)-4-ethyl-5-oxo-4,5-dihydro-1H-1,2,4-triazol-3-yl)propyl)[1,1'-biphenyl]-4-carboxylic acid, 1-(3'-(3-(1-(4-(tert-butyl)benzyl)-4-ethyl-5-oxo-4,5-dihydro-1H-1,2,4-triazol-3-yl)propyl)-4-ethoxy-[1,1'-biphenyl]-3-yl)cyclopropanecarboxylic acid,
2-(3'-(3-(1-(4-(tert-butyl)benzyl)-4-ethyl-5-oxo-4,5-dihydro-1H-1,2,4-triazol-3-yl)propyl)-4-ethoxy-[1,1'-biphenyl]-3-yl)acetic acid,
1-(3'-(3-(1-(4-(tert-butyl)benzyl)-4-ethyl-5-oxo-4,5-dihydro-1H-1,2,4-triazol-3-yl)propyl)-[1,1'-biphenyl]-3-yl)cyclopropanecarboxylic acid,
1-(3'-(3-(1-(4-(tert-butyl)benzyl)-4-ethyl-5-oxo-4,5-dihydro-1H-1,2,4-triazol-3-yl)propyl)-[1,1'-biphenyl]-4-yl)cyclopropanecarboxylic acid,
3'-(3-(1-(4-(tert-butyl)benzyl)-4-ethyl-5-oxo-4,5-dihydro-1H-1,2,4-triazol-3-yl)propyl)-4-methoxy-[1,1'-biphenyl]-3-carboxylic acid,
3'-(3-(1-(4-(tert-butyl)benzyl)-4-ethyl-5-oxo-4,5-dihydro-1H-1,2,4-triazol-3-yl)propyl)-4-ethoxy-[1,1'-biphenyl]-3-carboxylic acid,
2-(3'-(3-(1-(4-(tert-butyl)benzyl)-4-ethyl-5-oxo-4,5-dihydro-1H-1,2,4-triazol-3-yl)propyl)-4-propoxy-[1,1'-biphenyl]-3-yl)acetic acid,
N-(6-(3-(3-(1-(4-(tert-butyl)benzyl)-4-ethyl-5-oxo-4,5-dihydro-1H-1,2,4-triazol-3-yl)propyl)phenyl)pyridin-3-yl)benzenesulfonamide,
2-(3'-(3-(1-(4-(tert-butyl)benzyl)-4-ethyl-5-oxo-4,5-dihydro-1H-1,2,4-triazol-3-yl)propyl)-4-methoxy-[1,1'-biphenyl]-3-yl)acetic acid,
1-(3'-(3-(1-(4-(tert-butyl)benzyl)-4-ethyl-5-oxo-4,5-dihydro-1H-1,2,4-triazol-3-yl)propyl)-4-methyl-[1,1'-biphenyl]-3-yl)cyclopropanecarboxylic acid,
2-(4-(benzyloxy)-3'-(3-(1-(4-(tert-butyl)benzyl)-4-ethyl-5-oxo-4,5-dihydro-1H-1,2,4-triazol-3-yl)propyl)-[1,1'-biphenyl]-3-yl)acetic acid,
2-(3'-(3-(1-(4-(tert-butyl)benzyl)-4-ethyl-5-oxo-4,5-dihydro-1H-1,2,4-triazol-3-yl)propyl)-4-(cyclopropylmethoxy)-[1,1'-biphenyl]-3-yl)acetic acid,
2-(3'-(3-(1-(4-(tert-butyl)benzyl)-4-ethyl-5-oxo-4,5-dihydro-1H-1,2,4-triazol-3-yl)propyl)-4-fluoro-[1,1'-biphenyl]-3-yl)acetic acid,
2-(3'-(3-(1-(4-(tert-butyl)benzyl)-4-ethyl-5-oxo-4,5-dihydro-1H-1,2,4-triazol-3-yl)propyl)-6-ethoxy-[1,1'-biphenyl]-3-yl)acetic acid,
3'-(3-(1-(4-(tert-butyl)benzyl)-4-ethyl-5-oxo-4,5-dihydro-1H-1,2,4-triazol-3-yl)propyl)-4-propoxy-[1,1'-biphenyl]-3-carboxylic acid,
N-((3'-(3-(1-(4-(tert-butyl)benzyl)-4-ethyl-5-oxo-4,5-dihydro-1H-1,2,4-triazol-3-yl)propyl)-[1,1'-biphenyl]-3-yl)methyl)benzenesulfonamide,
3-(3'-(3-(1-(4-(tert-butyl)benzyl)-4-ethyl-5-oxo-4,5-dihydro-1H-1,2,4-triazol-3-yl)propyl)-4-methoxy-[1,1'-biphenyl]-3-yl)propanoic acid,
2-(3'-(3-(1-(4-(tert-butyl)benzyl)-4-ethyl-5-oxo-4,5-dihydro-1H-1,2,4-triazol-3-yl)-1,1-difluoropropyl)-4-ethoxy-[1,1'-biphenyl]-3-yl)acetic acid,
N-(6-(3-(3-(1-(4-(tert-butyl)benzyl)-4-ethyl-5-oxo-4,5-dihydro-1H-1,2,4-triazol-3-yl)-1,1-difluoropropyl)phenyl)pyridin-3-yl)benzenesulfonamide,
2-(5-(6-(3-(1-(4-(tert-butyl)benzyl)-4-ethyl-5-oxo-4,5-dihydro-1H-1,2,4-triazol-3-yl)propyl)pyridin-2-yl)-2-methoxyphenyl)acetic acid,
3-(3-(3'-(1H-tetrazol-5-yl)-[1,1'-biphenyl]-3-yl)propyl)-1-(4-(tert-butyl)benzyl)-4-ethyl-1H-1,2,4-triazol-5(4H)-one,
2-(5-(4-(3-(1-(4-(tert-butyl)benzyl)-4-ethyl-5-oxo-4,5-dihydro-1H-1,2,4-triazol-3-yl)propyl)pyrimidin-2-yl)-2-ethoxyphenyl)acetic acid,
2-(5-(6-(3-(1-(4-(tert-butyl)benzyl)-4-ethyl-5-oxo-4,5-dihydro-1H-1,2,4-triazol-3-yl)propyl)pyrimidin-4-yl)-2-ethoxyphenyl)acetic acid,
(3'-(3-(1-(4-(tert-butyl)benzyl)-4-ethyl-5-oxo-4,5-dihydro-1H-1,2,4-triazol-3-yl)propyl)-3-methoxy-[1,1'-biphenyl]-4-yl)acetic acid,
(3'-(3-(1-(4-(tert-butyl)benzyl)-4-ethyl-5-oxo-4,5-dihydro-1H-1,2,4-triazol-3-yl)propyl)-3-ethoxy-[1,1'-biphenyl]-4-yl)acetic acid,
(3'-(3-(1-(4-(tert-butyl)benzyl)-4-ethyl-5-oxo-4,5-dihydro-1H-1,2,4-triazol-3-yl)propyl)-3-propoxy-[1,1'-biphenyl]-4-yl)acetic acid,
2-(3'-(3-(1-(4-(tert-butyl)benzyl)-4-ethyl-5-oxo-4,5-dihydro-1H-1,2,4-triazol-3-yl)propyl)-3-hydroxy-[1,1'-biphenyl]-4-yl)acetic acid,
2-(3'-(3-(1-(4-(tert-butyl)benzyl)-4-ethyl-5-oxo-4,5-dihydro-1H-1,2,4-triazol-3-yl)propyl)-4-isopropoxy-[1,1'-biphenyl]-3-yl)acetic acid, and
2-(3'-(3-(1-(4-(tert-butyl)benzyl)-4-ethyl-5-oxo-4,5-dihydro-1H-1,2,4-triazol-3-yl)propyl)-4-(2-(dimethylamino)ethoxy)-[1,1'-biphenyl]-3-yl)acetic acid,
or a pharmaceutically acceptable salt of any of the foregoing, to a mammal in need thereof,
wherein the cancer is selected from the group consisting of prostate cancer, breast cancer, ovarian cancer, liver cancer, kidney cancer, colon cancer, pancreatic cancer, human chronic lymphocytic leukemia, and melanoma.

13. The method of claim 12, wherein the cancer is selected from the group consisting of prostate cancer, breast cancer, and ovarian cancer.

14. The method of claim 12, wherein the cancer is pancreatic cancer.

15. The method of claim 12, wherein the cancer is selected from the group consisting of liver cancer, colon cancer, and kidney cancer.

16. The method of claim 12, wherein the cancer is human chronic lymphocytic leukemia or melanoma.

17. The method of claim 1, wherein the compound has the structure:

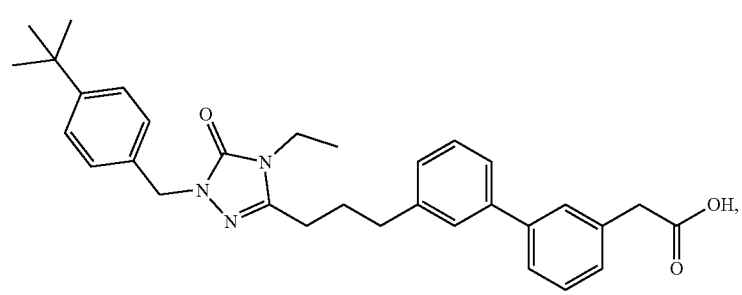

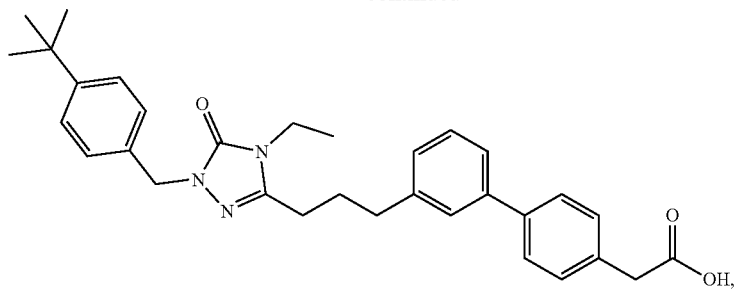
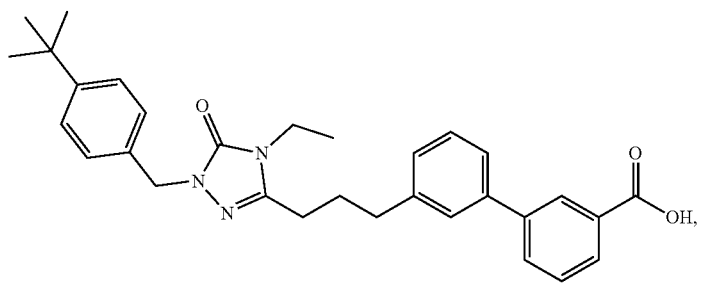
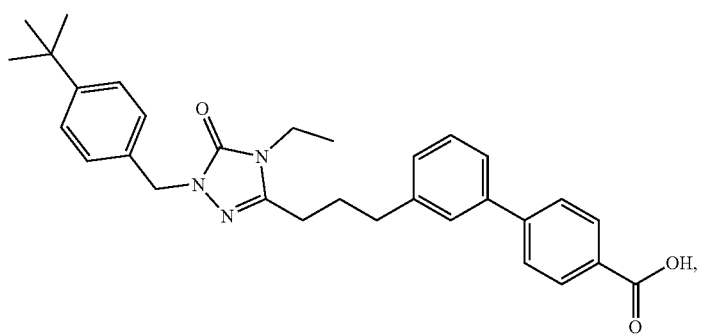
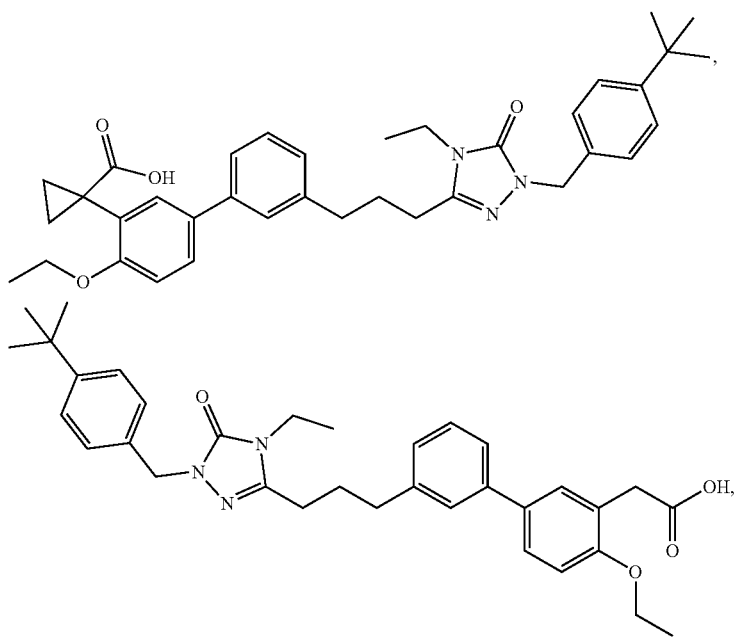

-continued
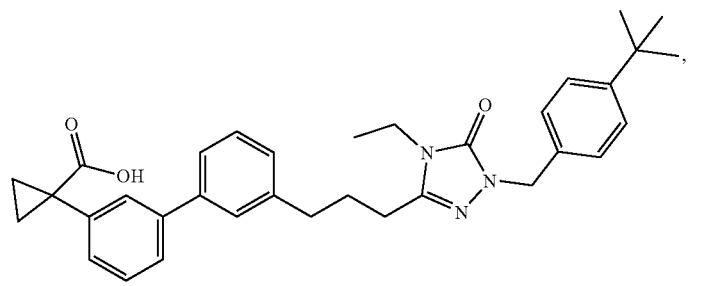
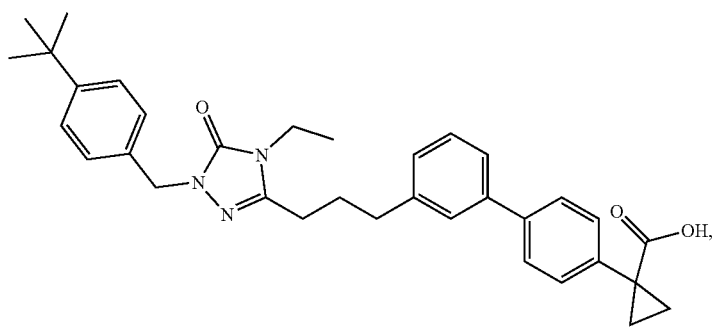
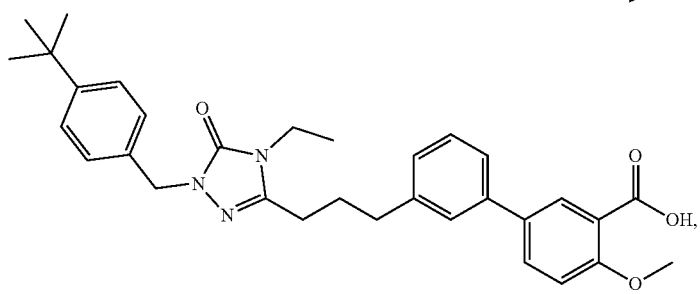
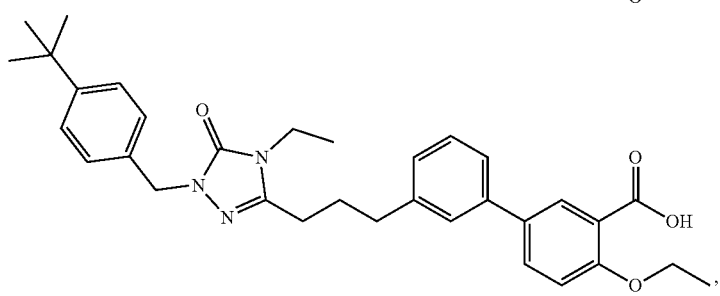
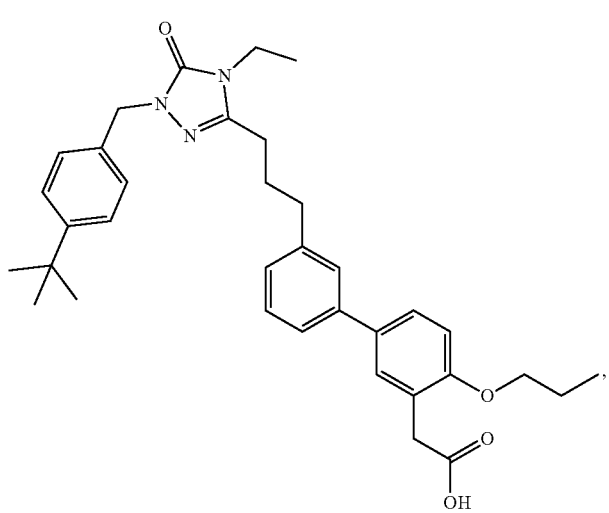

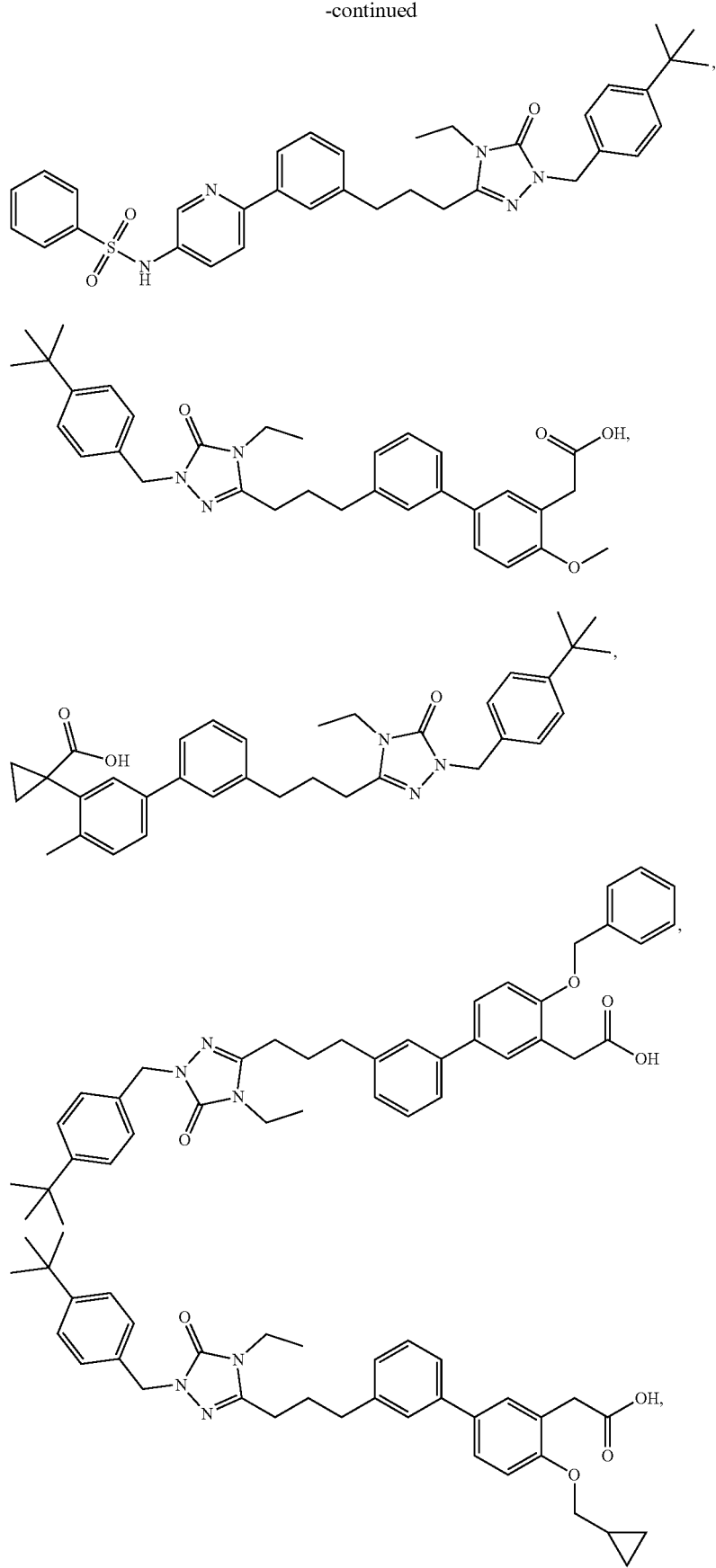

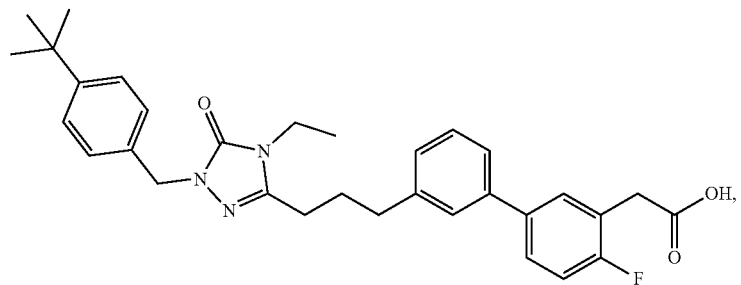
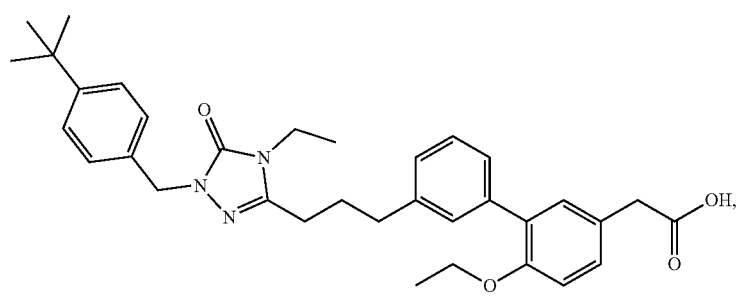
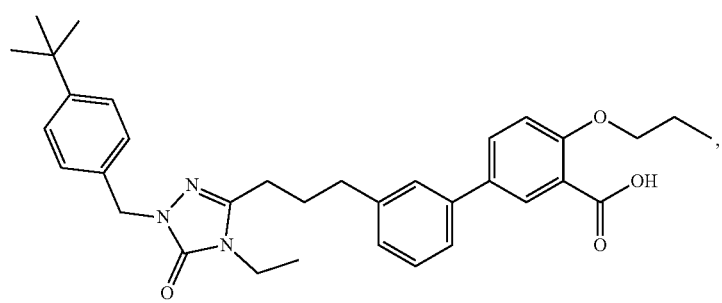
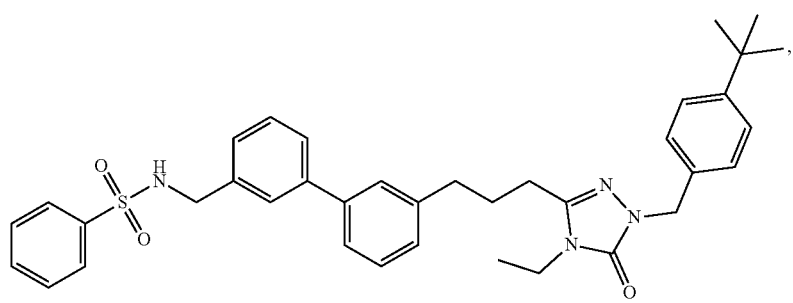
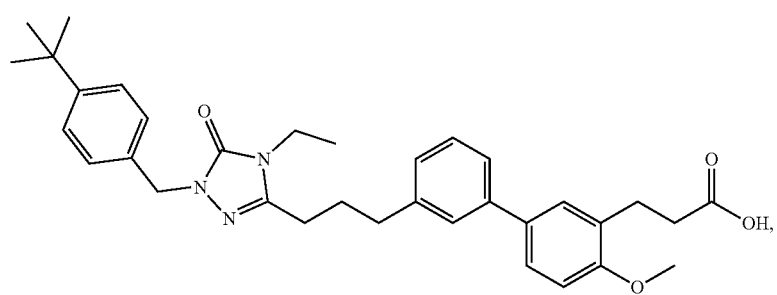

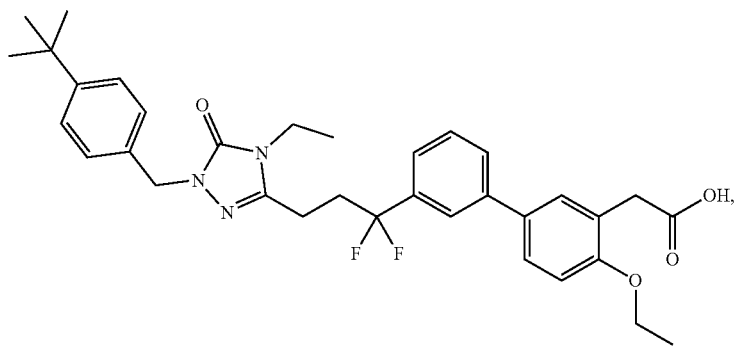
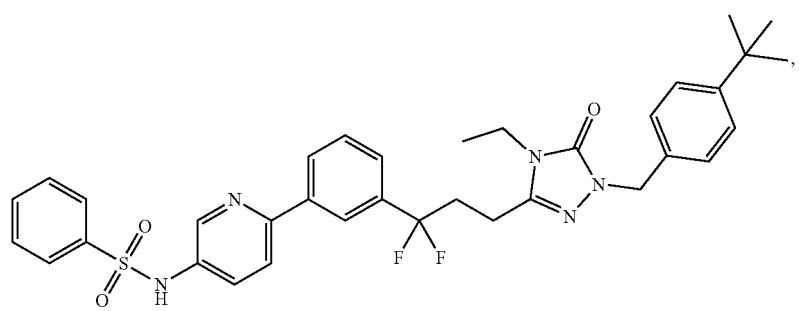
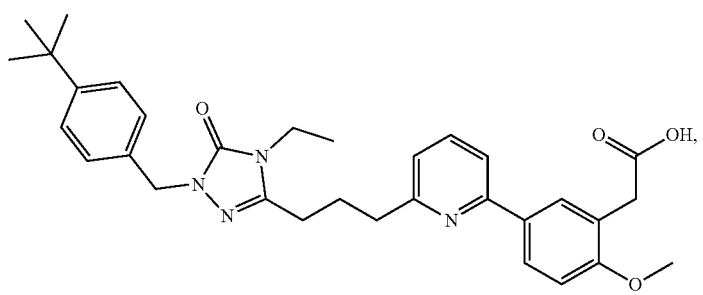
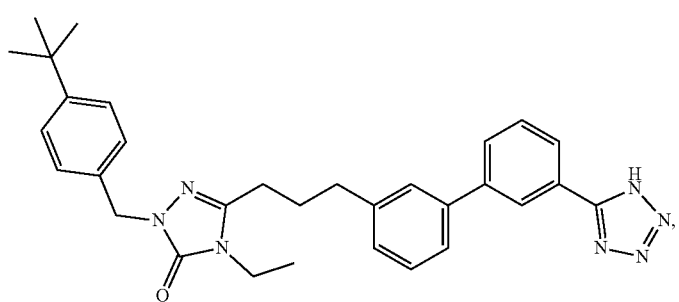
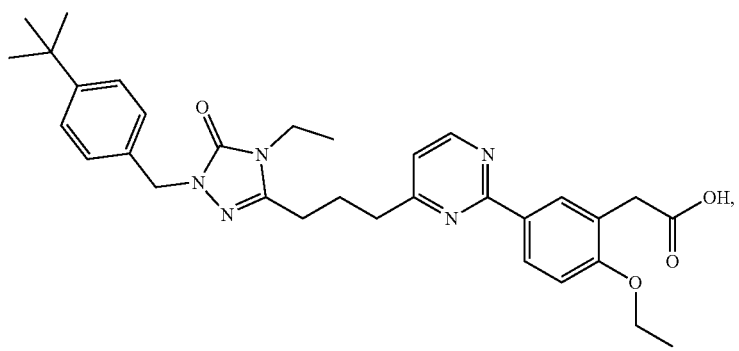

-continued
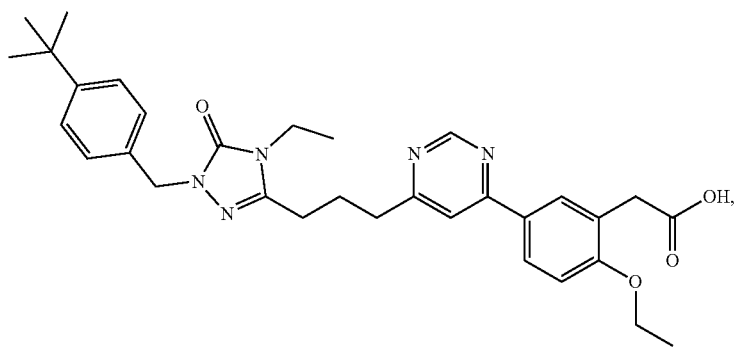
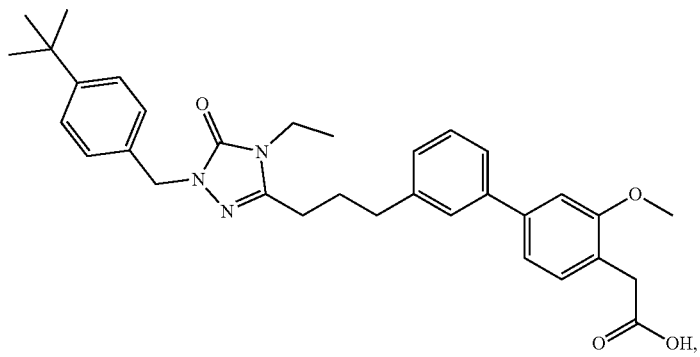
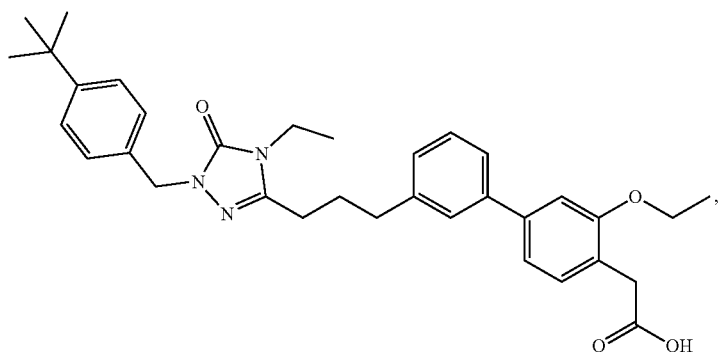
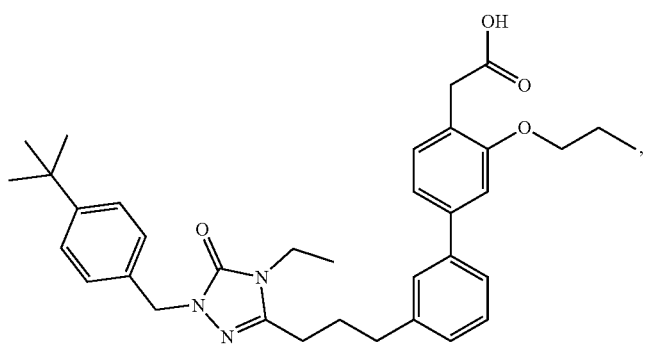
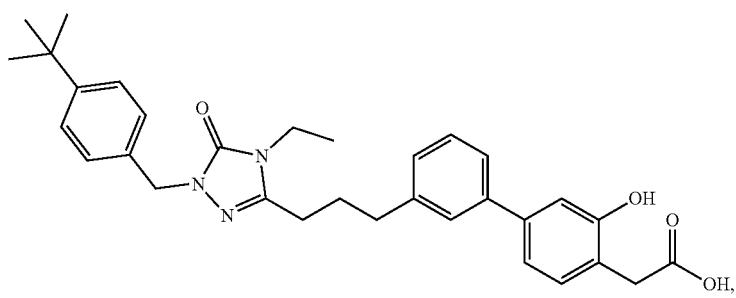

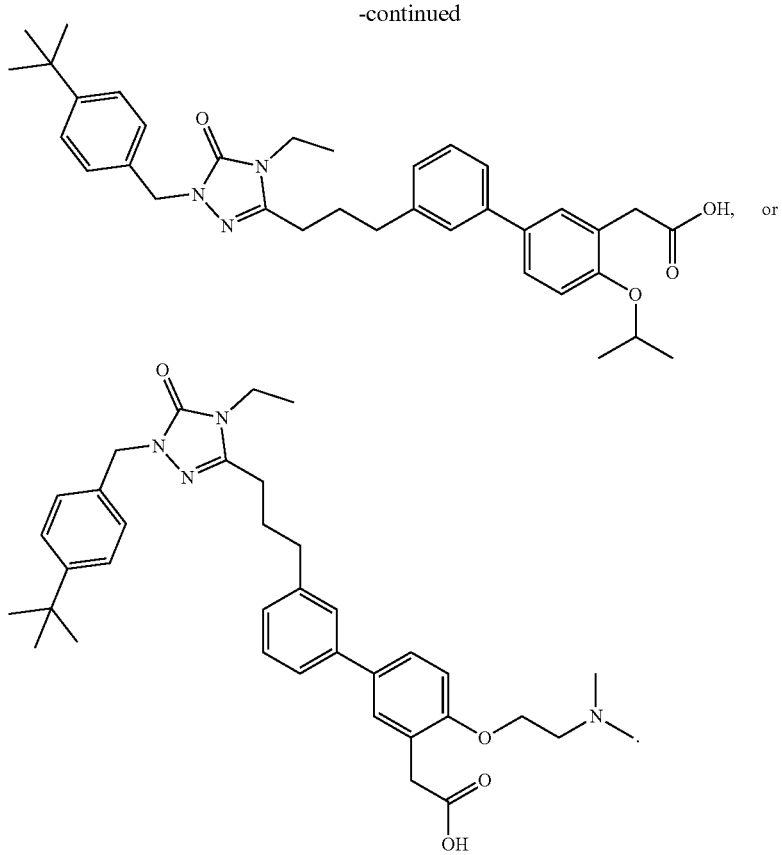
18. The method of claim 7, wherein the compound has the structure:
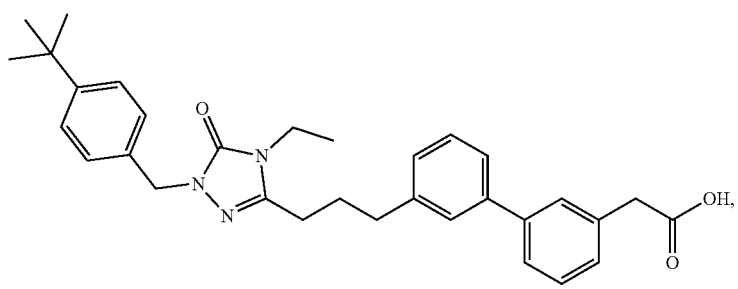
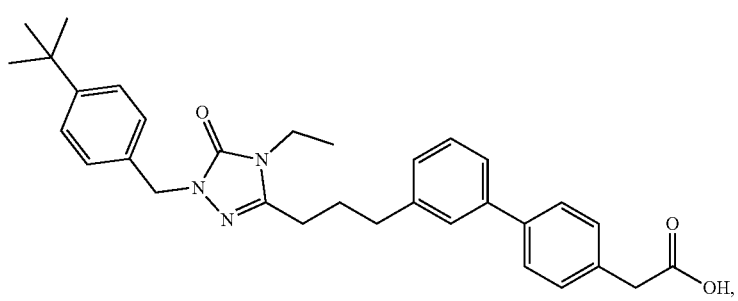

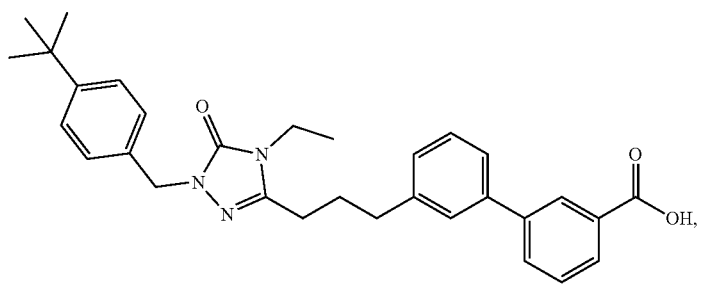
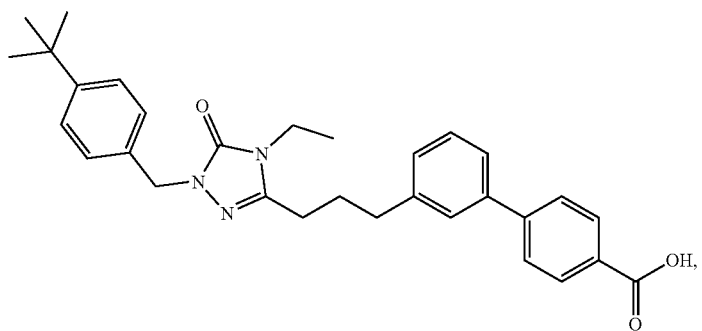
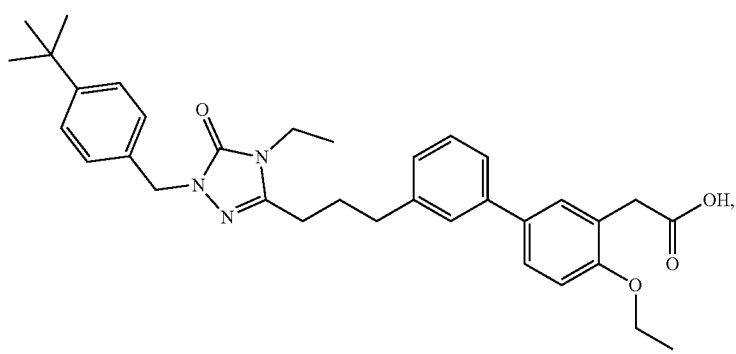
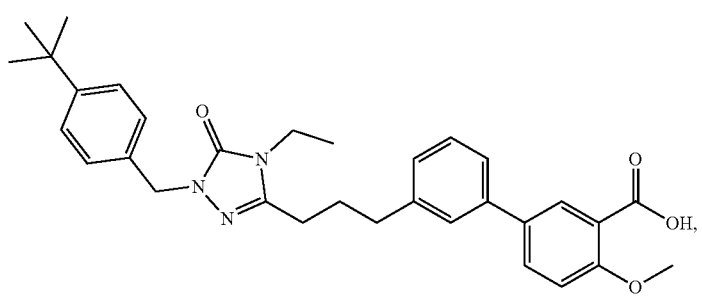
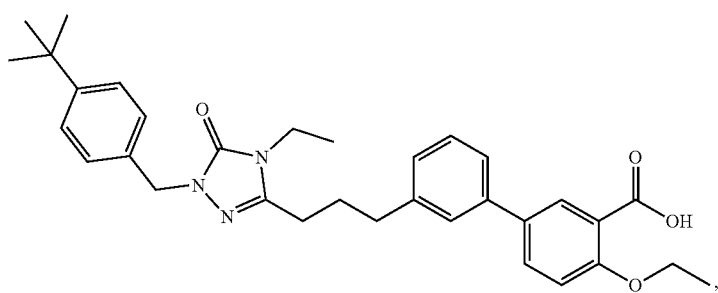

-continued
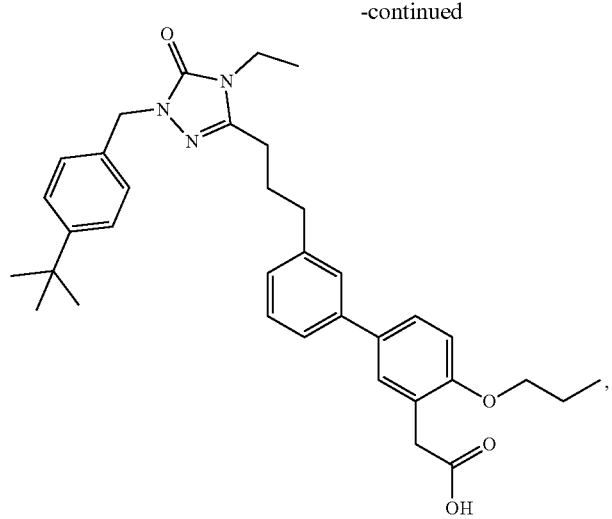
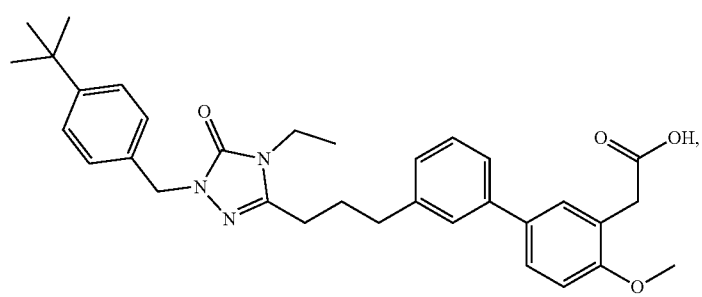
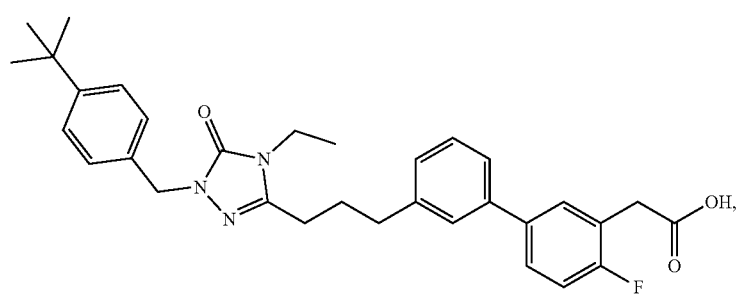
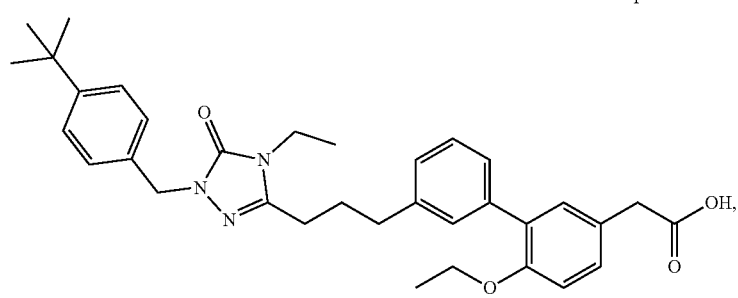
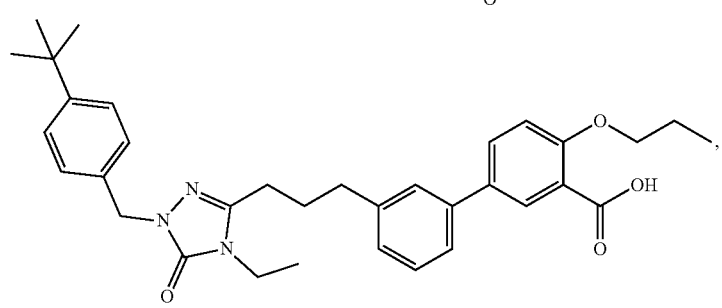

-continued
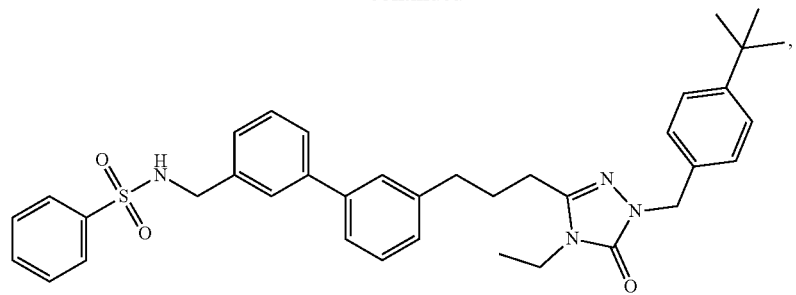
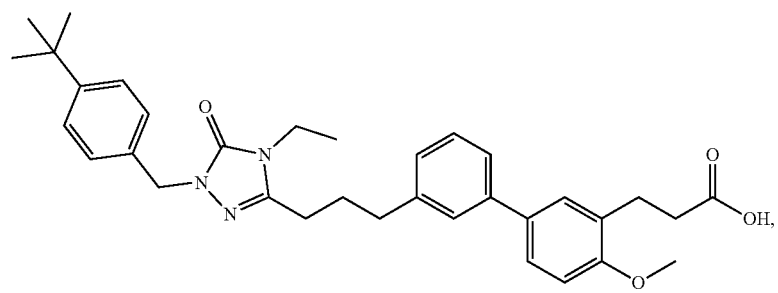
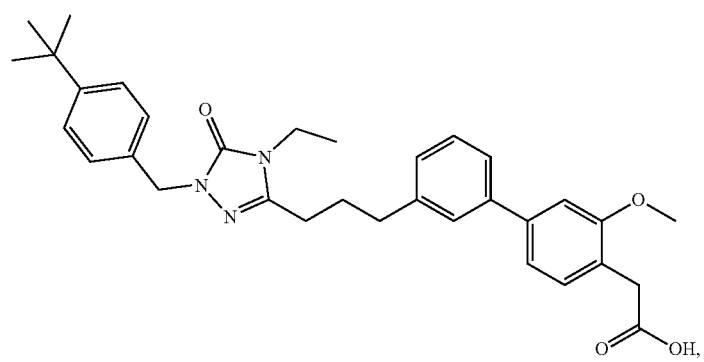
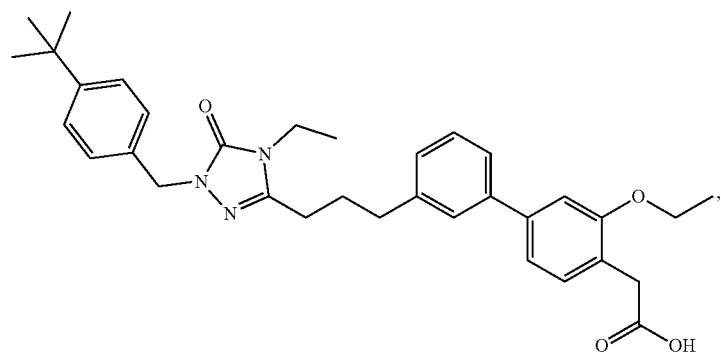
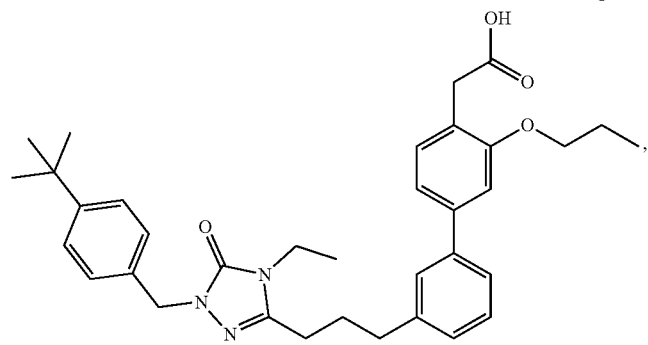

-continued
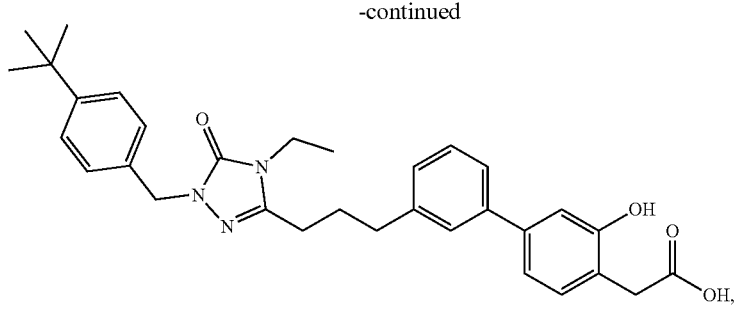
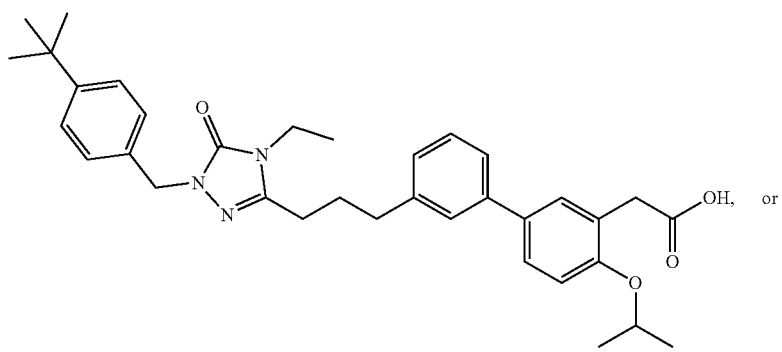
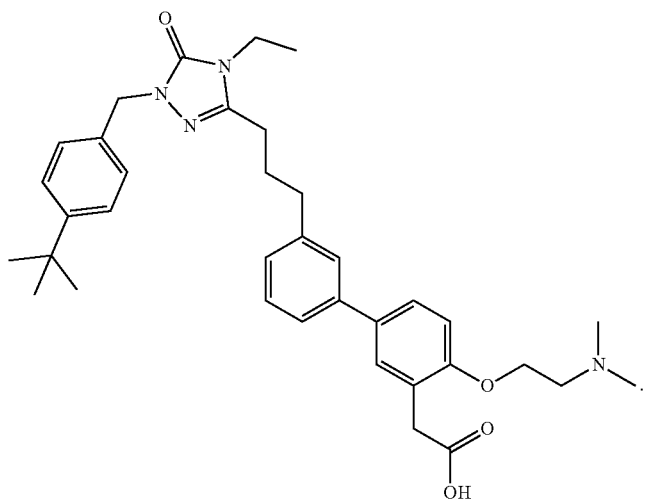 [SMILES: CCn1c(CCCc2cccc(-c3ccc(OCCN(C)C)c(CC(=O)O)c3)c2)nn(Cc2ccc(C(C)(C)C)cc2)c1=O]
19. The method of claim 18, wherein the compound has the structure:
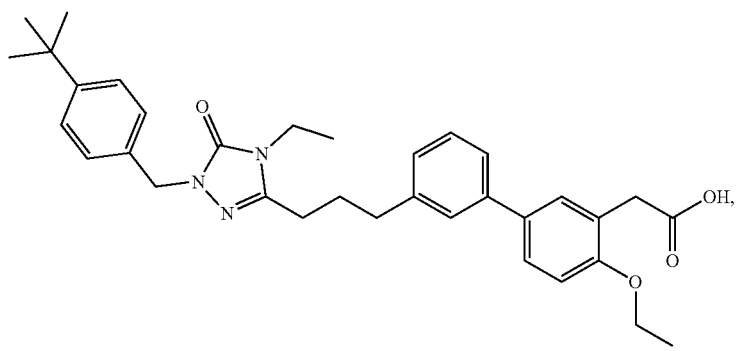

-continued
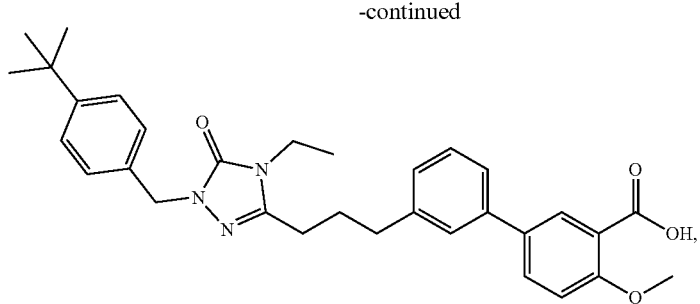
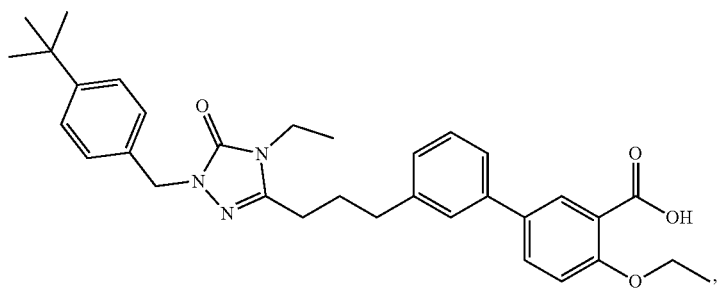
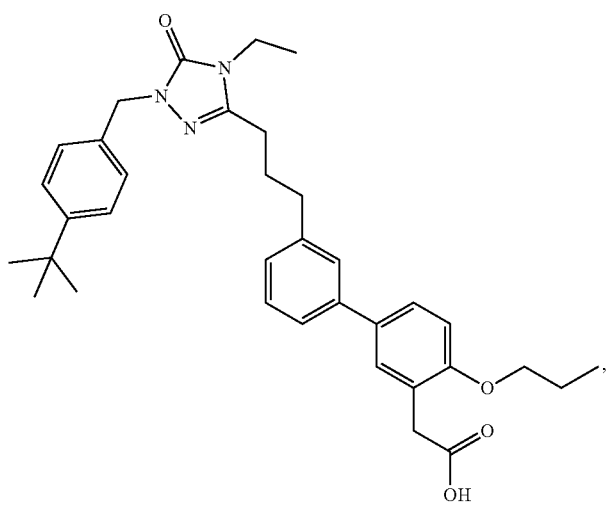
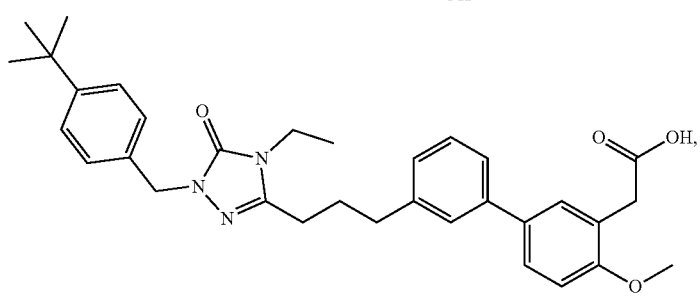
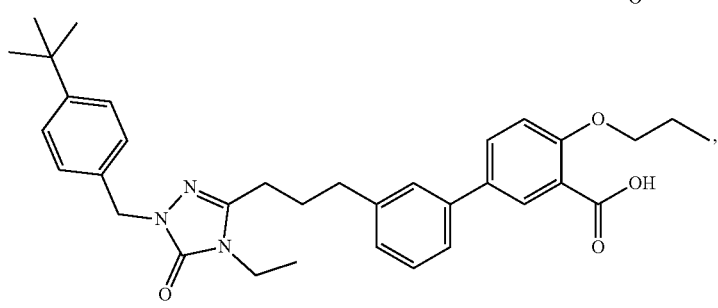

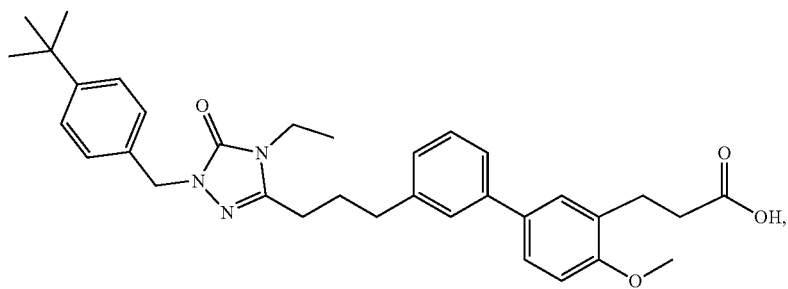
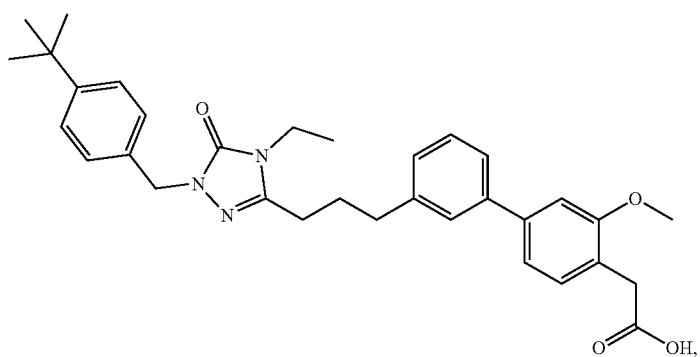
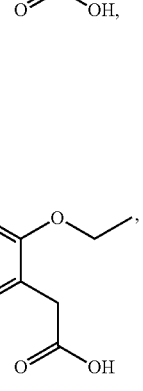
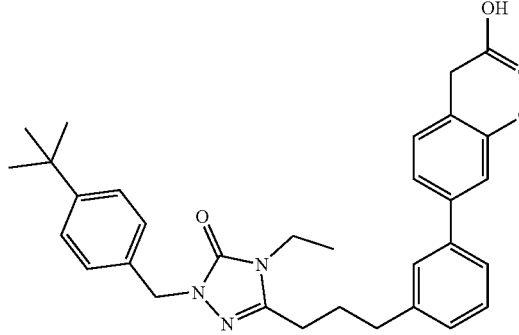
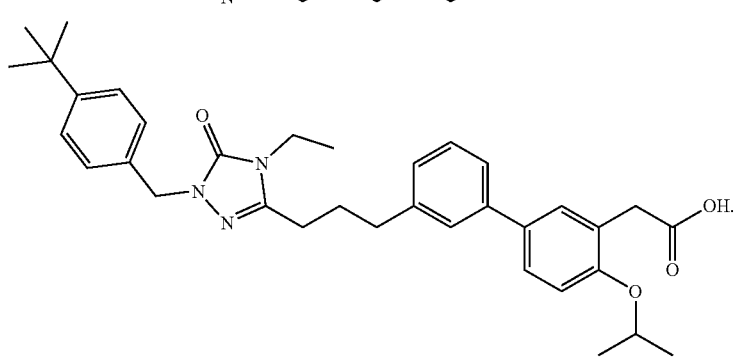

20. The method of claim 18, wherein the compound has the structure:
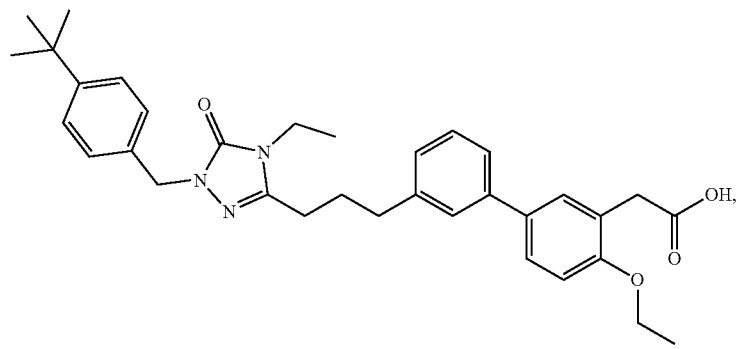
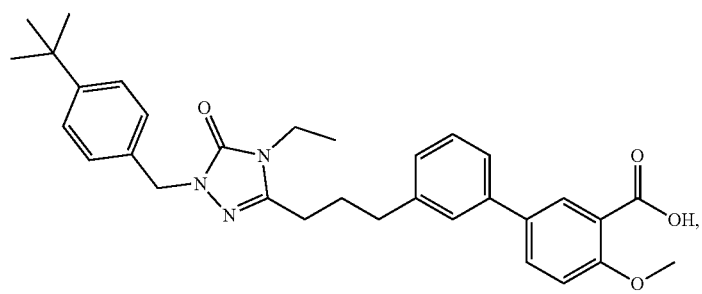
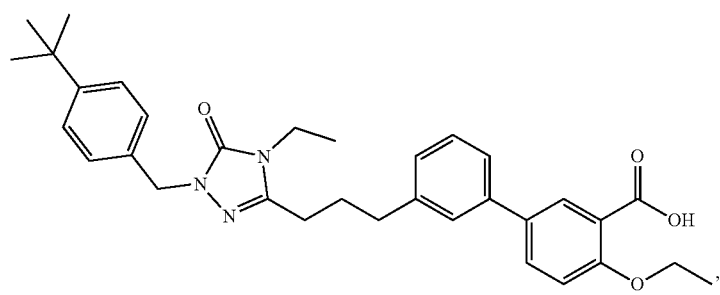
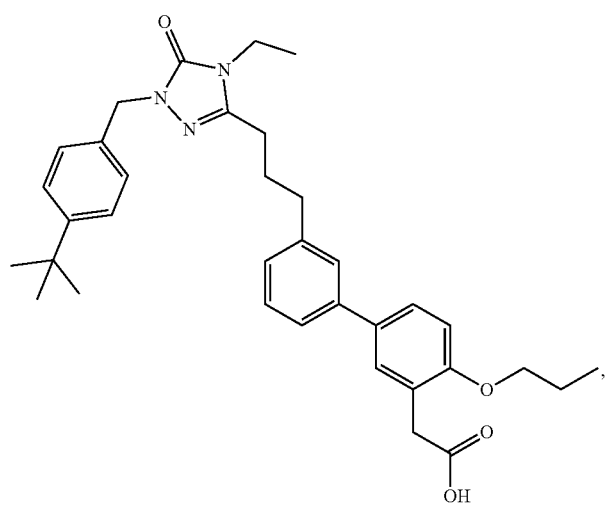

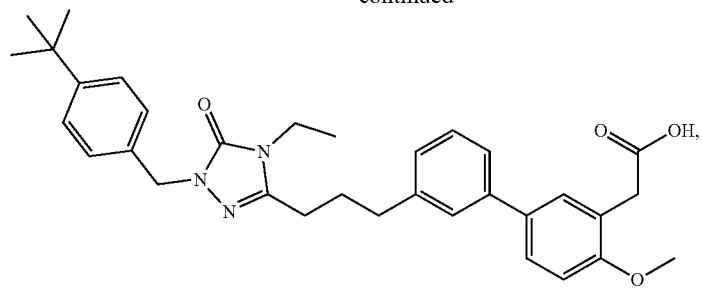
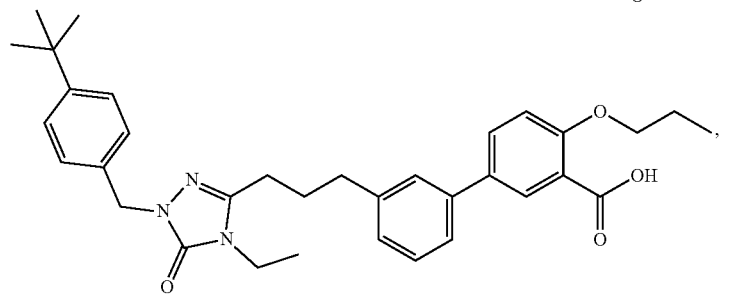, or
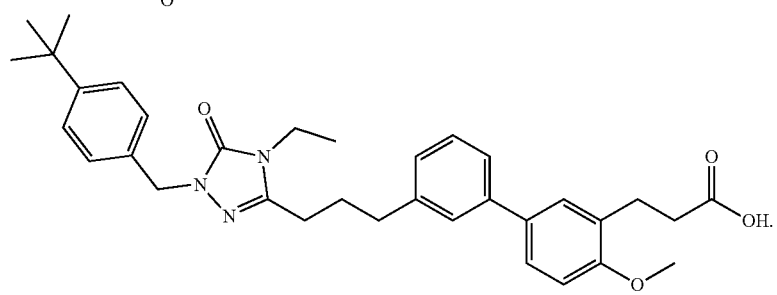
* * * * *

UNITED STATES PATENT AND TRADEMARK OFFICE
CERTIFICATE OF CORRECTION

PATENT NO. : 10,568,871 B2  Page 1 of 1
APPLICATION NO. : 15/590766
DATED : February 25, 2020
INVENTOR(S) : Nicholas Simon Stock et al.

It is certified that error appears in the above-identified patent and that said Letters Patent is hereby corrected as shown below:

In the Claims

Claim 5: Column 75, Line 45: "(b) –O–(R)," should read -- (b) –O–($R^7$), --.

Claim 5: Column 75, Line 46: "(c) –N($R^7$)S(=O)$_2$(R), and" should read -- (c) –N($R^7$)S(=O)$_2$($R^8$), and --.

Claim 5: Column 75, Line 51: "(b) –O–(R)," should read -- (b) –O–($R^7$), --.

Claim 6: Column 75, Line 66: "(b) –O–(R)," should read -- (b) –O–($R^7$), --.

Claim 6: Column 76, Line 10: "(c) –$C_{1-4}$alkyl(R); and" should read -- (c) –$C_{1-4}$alkyl($R^7$); and --.

Claim 6: Column 76, Line 14: "(c) –$C_{1-6}$alkyl(R); and" should read -- (c) –$C_{1-6}$alkyl($R^7$); and --.

Signed and Sealed this
Fifth Day of May, 2020

Andrei Iancu
*Director of the United States Patent and Trademark Office*